US012797333B2

(12) United States Patent
Jeong et al.

(10) Patent No.: US 12,797,333 B2
(45) Date of Patent: Nov. 17, 2026

(54) METHOD FOR PREPARING PROTEIN MICROBEADS FOR IMPROVING STABILITY OF PROTEIN PREPARATION

(71) Applicant: DONGGUK UNIVERSITY INDUSTRY-ACADEMIC COOPERATION FOUNDATION, Seoul (KR)

(72) Inventors: Seong Hoon Jeong, Gyeonggi-do (KR); Nam Ah Kim, Jeollanam-do (KR)

(73) Assignee: DONGGUK UNIVERSITY INDUSTRY-ACADEMIC COOPERATION FOUNDATION, Seoul (KR)

(*) Notice: Subject to any disclaimer, the term of this patent is extended or adjusted under 35 U.S.C. 154(b) by 504 days.

(21) Appl. No.: 18/263,420

(22) PCT Filed: Dec. 30, 2021

(86) PCT No.: PCT/KR2021/020309
§ 371 (c)(1),
(2) Date: Jul. 28, 2023

(87) PCT Pub. No.: WO2022/164061
PCT Pub. Date: Aug. 4, 2022

(65) Prior Publication Data

US 2024/0082159 A1 Mar. 14, 2024

(30) Foreign Application Priority Data

Jan. 29, 2021 (KR) ........................ 10-2021-0013460

(51) Int. Cl.
*A61K 38/00* (2006.01)
*A61K 9/16* (2006.01)

(52) U.S. Cl.
CPC .......... *A61K 9/1682* (2013.01); *A61K 9/1623* (2013.01); *A61K 9/1658* (2013.01)

(58) Field of Classification Search
CPC .. A61K 9/1682; A61K 9/1623; A61K 9/1658; A61K 9/1075; A61K 38/00
See application file for complete search history.

(56) References Cited

U.S. PATENT DOCUMENTS

2014/0288282 A1* 9/2014 Petrel ...................... B01F 33/45 422/224

FOREIGN PATENT DOCUMENTS

CN 105832704 8/2016
KR 100426223 4/2004
(Continued)

OTHER PUBLICATIONS

Kim et al. (International Journal of Biological Macromolecules 2021;185:935-948) (Year: 2021).*
(Continued)

*Primary Examiner* — Ernst V Arnold
(74) *Attorney, Agent, or Firm* — Riverside Law LLP

(57) ABSTRACT

The present invention relates to a method for preparing protein microbeads for improving the stability of a protein preparation. It was confirmed that when protein is mixed with trehalose and protein is dehydrated in n-octanol by using the SPG membrane emulsification technique, microbeads with a narrow particle size distribution and high reversibility are formed, and the microbeads exhibit high stability to external shock or high temperature stress compared to protein solutions. Accordingly, the method for preparing protein microbeads according to the present invention is expected to be utilized as a method for improving storage stability by applying same to the preparation of high-concentration protein pharmaceuticals.

10 Claims, 36 Drawing Sheets

(56) References Cited

FOREIGN PATENT DOCUMENTS

| | | | | |
|---|---|---|---|---|
| WO | WO-9214449 A1 * | 9/1992 | ........... | A61K 9/0019 |
| WO | WO-2017173068 A1 * | 10/2017 | ........... | A61K 9/5026 |

OTHER PUBLICATIONS

Sihan et al. (Scientific Reports 2016;6:26407: 7 pages) (Year: 2016).*
Yedomon et al. (European Journal of Pharmaceutics and Biopharmaceutics 2013;85:398-405) (Year: 2013).*
Joseph et al. (European Journal of Pharmaceutics and Biopharmaceutics 87 (2014) 178-186) (Year: 2014).*
Vladisavljevic et al. (Microfluid Nanofluid (2012) 13:151-178). (Year: 2012).*
Liu et al. (Journal of Controlled Release 2005; 103:31-43). (Year: 2005).*
Aniket, D. A., et al., "MicroglassificationTM: A Novel Technique for Protein Dehydration", Journal of Pharmaceutical Sciences, American Chemical Society and American Pharmaceutical Association, vol. 103, No. 3 (Jan. 10, 2014), pp. 810-820.
Kim N. A., et al., "Protein microbeadification to achieve highly concentrated protein formulation with reversible properties and in vivo pharmacokinetics after reconstitution", International Journal of Biological Macromolecules, vol. 185 (Jul. 5, 2021), pp. 935-948.
Park S.-K., et al., "Lessons Learned in Protein Precipitation Using a Membrane Emulsification Technique to Produce Reversible and Uniform Microbeads", Pharmaceutics, vol. 13, No. 10 (Oct. 19, 2021), Article 1738.
Rickard Deborah Lee, "Multiphase, Multicomponent Systems: Divalent Ionic Surfactant Phases and Single-Particle Engineering of Protein and Polymer Glasses", PhD Thesis, Department of Mechanical Engineering and Materials Science Duke University, (Jan. 1, 2011), PhD Thesis, Department of Mechanical Engineering and Materials Science Duke University, 2001, pp. 1-320.
Vladisavljevic, G.T., et al., "Shirasu Porous Glass membrane emulsification: Characterisation of membrane structure by high-resolution X-ray microtomography and microscopic observation of droplet formation in real time", Journal of Membrane Science, vol. 302, No. 1-2 (Jul. 5, 2007), pp. 243-253.

* cited by examiner

SEM image after drying

Microscopic observation before drying

*SEM images of IgG microbeads after drying*

METHOD FOR PREPARING PROTEIN MICROBEADS FOR IMPROVING STABILITY OF PROTEIN PREPARATION

CROSS-REFERENCE TO RELATED APPLICATIONS

This application is a U.S. national phase application filed under 35 U.S.C. § 371 claiming benefit to International Patent Application No. PCT/KR2021/020309, filed on Dec. 30, 2021, which claims priority to Korean Application No. 10-2021-0013460, filed on Jan. 29, 2021, the disclosures of each of which are incorporated by reference herein in their entirety.

TECHNICAL FIELD

The present invention relates to a method for preparing protein microbeads for improving the stability of a protein preparation.

This application claims priority based on Korean Patent Application No. 10-2021-0013460 filed on Jan. 29, 2021, and all contents disclosed in the specification and drawings of the application are incorporated herein by reference.

BACKGROUND ART

The demand for economical technology has been increasing, working in synergy with large-scale production of high value-added biological products and highly concentrated therapeutic proteins. This demand has significantly improved upstream productivity that increases protein levels to 10 g/L or more. After additional purification stages to remove biomass and impurities, the solution is filled into containers or freeze-dried in vials for long-term storage. Recently, prefilled syringes or cartridges (i.e., easily filled drug solutions) have been preferred in the handling of therapeutic proteins because they are more convenient and less expensive to manufacture than the freeze-drying process. Nonetheless, the long-term storage stability of proteins is higher in freeze-dried vials than in pre-filled syringes, minimizing the rate of change in drug content.

Liquid protein formulations are more susceptible to physical denaturation than dried solids. For example, pump operations, such as delivering protein solutions to containers, can induce proteinaceous particles due to surface stress. Furthermore, mishandling such as bouncing or dropping a plastic syringe loaded with protein may also induce proteinaceous particles due to silicon oil and cavitation. Similarly, proteinaceous particles can substantially occur due to various mechanical stresses during manufacturing or just before administration.

In relation to this, the transition melting temperature (Tm) was higher in highly concentrated etanercept, but higher monomer losses were observed during accelerated storage stability tests. The results suggest that protein aggregation could become a significant issue after manufacturing, particularly in the case of high concentration protein formulations. Thus, liquid formulations generally have a concentration limit of 100 mg/mL to minimize protein aggregation, but the typical injection volume for subcutaneous administration is limited to less than 1.5 mL. This is known to be due to the back pressure of the subcutaneous tissue that can push out the injected drug and the injection pain that occurs when administering larger volumes. Therefore, high concentration protein formulations should ideally be suitable for small volumes of more than 150 mg/mL.

One method of minimizing protein aggregation involves limiting the mobility of the protein to reduce collision frequency, and lyophilization using an appropriate excipient can minimize protein mobility, enhancing protein stability and suppressing protein aggregation. Moreover, the removal of water from a protein solution minimizes hydrolysis reactions, thereby limiting structural flexibility. For these reasons, lyophilization is often used to dehydrate proteins via well-validated processes in terms of protein stability during both freezing and drying processes. However, lyophilized protein must be reconstituted prior to administration, thus lyophilization of protein is not the ultimate solution, which is the point of addressing the problem of protein rehydration at high concentration. Furthermore, lyophilized protein precipitates are not suitable for additional constraint processes due to their low fluidity. As a result, it requires more costs to manufacture them into pre-filled syringes for administration as is. However, it may be more efficient for long-term storage that avoids low temperature preservation.

Meanwhile, the term "microcapsules" is generally defined as spherical particles ranging in size from 50 nm to 2 mm that contain a core material. However, protein precipitates are a single dispersion of protein without additional treatment on the outer layer. In the present invention, these protein precipitates have been named "protein microbeads". They are, in fact, micron-sized spheres of dried solid state that are easy to handle and potentially can be injected as is without reconstitution.

Theoretically, protein dehydration in a non-miscible organic solvent is possible at room temperature, leading to rapid solidification. In previous studies, lysozyme was evaluated to observe various precipitation conditions in the generation of stable and reversible protein precipitates, and the precipitates were reversible when dehydrated in a non-miscible organic solvent. However, the precipitates were mixtures of crystals and protein microbeads, speculated to be due to the slow dehydration speed (i.e., shaking at 30 rpm).

Accordingly, the inventors of the present invention developed a method that can overcome the problems of existing protein precipitation methods that may cause inconsistent release profiles and efficacy due to their wide particle size distribution, and can form more stable and reversible protein microbeads and narrow their size distribution range. It is intended to apply this method to maintain stability during the manufacture of high concentration protein preparations.

DISCLOSURE

Technical Problem

The inventors of the present invention, through the research of methods that can improve the stability of proteins such as suppression of protein aggregation in protein formulations, have discovered that protein microbeads manufactured using an organic solvent for protein dehydration, the addition of an excipient, and the use of SPG membrane emulsion technology, exhibit stability to external shocks, high temperatures, etc., and show a narrow size distribution with high reversibility. In the manufacture of protein microbeads, the inventors have confirmed the optimal conditions by comparing the size and stability of the microbeads depending on the type of organic solvent, the type of excipient, and whether SPG membrane emulsion technology is used. Based on these findings, the present invention was completed.

Therefore, the purpose of the present invention is to provide a method for preparing protein microbeads and protein microbeads manufactured by the preparing method.

However, the technical challenges that the present invention aims to solve are not limited to the challenges mentioned above, and other challenges not mentioned can be clearly understood by those of ordinary skill in the art from the following disclosure.

Technical Solution

To achieve the purpose as mentioned, the present invention provides a method for preparing protein microbeads, comprising the following steps:

(a) stirring an emulsion prepared by mixing protein with a process stabilizer and an organic solvent and dehydrating the protein;
(b) removing the supernatant by centrifuging a precipitate formed by stirring the emulsion and dehydrating the protein; and
(c) drying after removing the supernatant.

In one embodiment of the present invention, the protein may be one or more selected from a group consisting of antibodies, aptamers, fusion proteins, Fc fusion proteins, PEGylated proteins, synthetic polypeptides, protein fragments, lipoproteins, enzymes, hormones, immunogenic proteins, structural peptides, and peptide drugs, but is not limited thereto.

In another embodiment of the present invention, the organic solvent may be a non-aqueous organic solvent that does not mix with water and has a water saturation fraction (f) value of 0.5 or less, but is not limited thereto.

In yet another embodiment of the present invention, the organic solvent may be one or more selected from a group consisting of carbonates, esters, ethers, ketones, alcohols, non-polar solvents, and their isomers, but is not limited thereto.

In yet another embodiment of the present invention, the organic solvent may be n-octanol, but is not limited thereto.

In yet another embodiment of the present invention, the process stabilizer may be one or more selected from a group consisting of diluents and saccharides, but is not limited thereto.

In yet another embodiment of the present invention, the process stabilizer may be one or more selected from a group consisting of trehalose, mannitol, and sucrose, but is not limited thereto.

In yet another embodiment of the present invention, the step (a) may further comprise emulsifying the protein through a Shirasu porous glass (SPG) membrane or a microchip before stirring the emulsion, which may allow for the uniformity of particle shape and size of the protein microbeads, but is not limited thereto.

In yet another embodiment of the present invention, the reversibility of the protein microbeads may be 90% to 100%, but is not limited thereto.

In yet another embodiment of the present invention, the protein microbeads may have stability against physical shocks or high temperature stress of 40° C. to 70° C., but is not limited thereto.

In yet another embodiment of the present invention, the dehydration in the step (a) may be performed for 10 seconds to 20 minutes, but is not limited thereto.

In yet another embodiment of the present invention, the drying in the step (c) may be performed at 25° C. to 40° C. for 24 to 130 hours under a pressure of 50 mTorr to 300 mTorr, but is not limited thereto.

In yet another embodiment of the present invention, the protein microbeads may be formulated into one or more form selected from a group consisting of injectables, inhalants, patches, and topical formulations, but is not limited thereto.

Also, the present invention provides protein microbeads that are prepared by the preparation method above, wherein the protein microbeads have a reversibility of 90% to 100%, and possess stability against physical shocks or high temperature stress of 40° C. to 70° C.

Advantageous Effects

The present invention has confirmed that when protein is dehydrated in n-octanol using SPG membrane emulsification technology after mixing trehalose with protein, microbeads with a narrow particle size distribution and high reversibility are formed, and these show higher stability against external shocks or high-temperature stress compared to the protein solution. Therefore, the method for preparing protein microbeads according to the present invention is expected to be usefully utilized as a method for improving storage stability by applying the same to the preparation of high-concentration protein pharmaceuticals and the like.

BRIEF DESCRIPTION OF THE DRAWINGS

FIG. 1C is a drawing identifying the size distribution of BSA by Dynamic Light Scattering (DLS), FIG. 1D is a drawing identifying the monomer reversibility of BSA by Size Exclusion Chromatography (SEC), and FIG. 1E is a drawing identifying the folding reversibility of BSA by Differential Scanning Calorimetry (DSC).

BEST MODES OF THE INVENTION

Figure 1A:
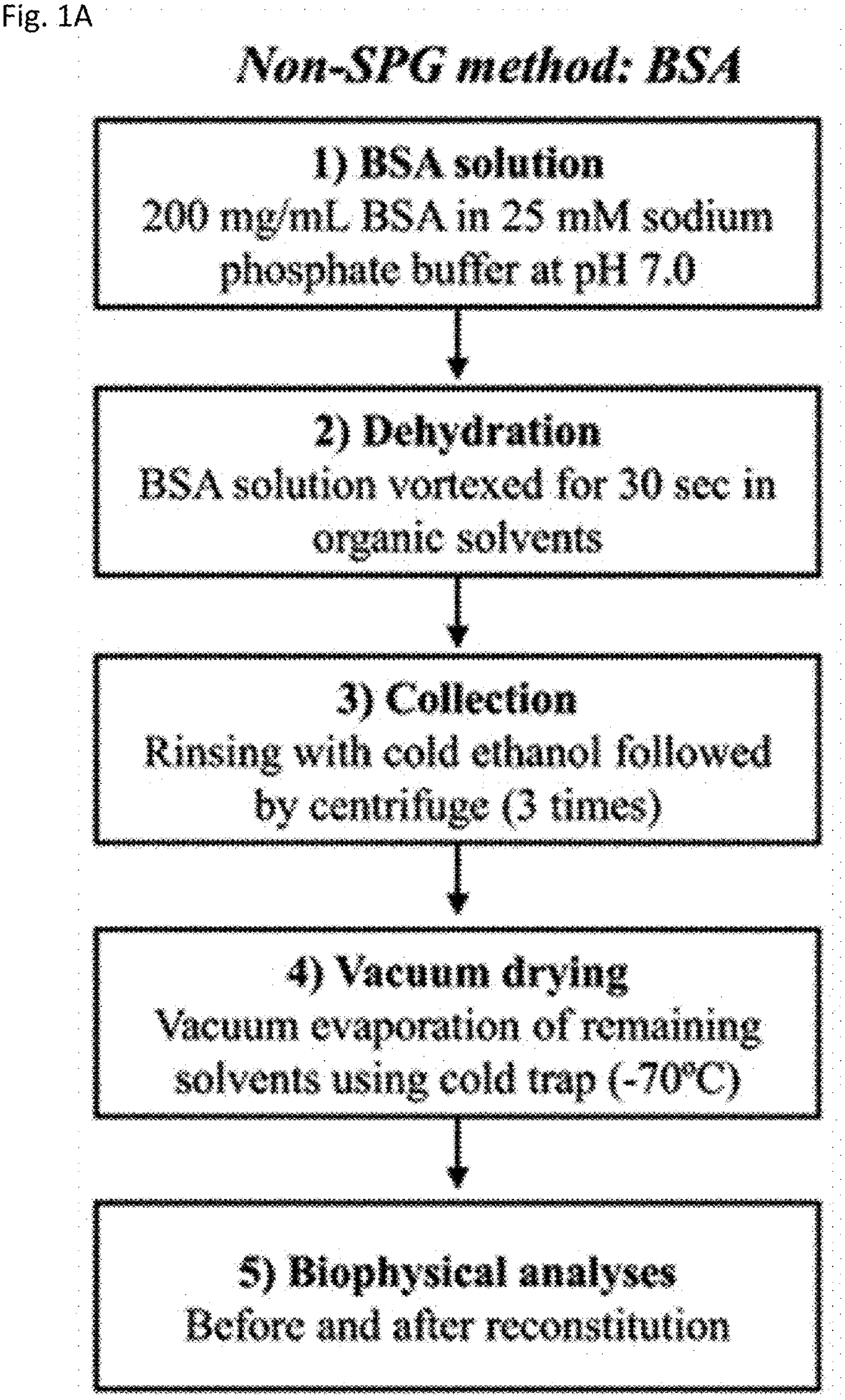
FIG. 1A is a schematic diagram sequentially illustrating a non-SPG method in the manufacturing of BSA microbeads according to an embodiment of the present invention.

In one experimental example of the present invention, it was confirmed that when BSA microbeads were dehydrated using ethanol, isopropyl alcohol (IPA), pentanol, and n-octanol, no crystals or impurities appeared in the BSA microbeads in case of using n-octanol rather than other solvents, they did not form aggregates, and showed high reversibility (Experimental Example 1).

In another experimental example of the present invention, the effect of the SPG membrane on the formation of IgG microbeads was confirmed, and it was found that when the SPG membrane was used during microbead manufacture, the particles were uniform and smaller in size (Experimental Example 2).

In yet another embodiment of the present invention, the effect of dehydration time on the formation of IgG microbeads was confirmed, and it was found that the optimal dehydration time was 30 seconds (Experimental Example 3).

In yet another embodiment of the present invention, the effect of temperature and excipients on the formation of IgG microbeads was confirmed, and it was found that at 4° C., compared to room temperature (RT), when PS80 and trehalose were used as excipients, the particle size was smaller and the particle size distribution was narrower (Experimental Example 4).

In yet another embodiment of the present invention, the reversibility of IgG microbeads by PS80 and trehalose was confirmed, and it was found that using trehalose showed higher reversibility than using PS80 (Experimental Example 5).

In yet another embodiment of the present invention, the effect of drying conditions and initial concentration on the formation of IgG microbeads was confirmed, and it was found that the optimal conditions were drying at 35° C.

under a vacuum pressure of 200 mTorr for 48 hours, and that the reversibility of microbeads was higher when the initial concentration of IgG was 10 mg/mL compared to 50 mg/mL (Experimental Example 6).

In yet another embodiment of the present invention, when falling and thermal stresses were applied to IgG microbeads, it was found that the microbeads using trehalose showed higher reversibility than those using PS80, and that the microbeads using trehalose had higher stability (Experimental Example 7).

In yet another embodiment of the present invention, the PK profile of the reconstituted IgG microbeads in rats was confirmed, and it was found that overall, after reconstitution, the IgG microbeads showed almost the same PK profile as the IgG derived from the marketed product (Experimental Example 8).

Hereinafter, the present invention is described in detail.

The present invention provides a method for preparing protein microbeads comprising the following steps:

(a) stirring an emulsion prepared by mixing protein with a process stabilizer and an organic solvent and dehydrating the protein;

(b) removing the supernatant by centrifuging a precipitate formed by stirring the emulsion and dehydrating the protein; and (c) drying after removing the supernatant.

In addition, the present invention provides protein microbeads prepared by the method described.

In the present invention, the term "protein" typically denotes an amino acid sequence (i.e., a polypeptide) having a molecular weight of about 1-3000 kiloDaltons (kDa). A polypeptide having a molecular weight of about 1 kDa or more is considered to be a protein for the purpose of the present invention. As understood by those skilled in the art, a polypeptide having a sufficient chain length can have a tertiary or quaternary structure, while a shorter polypeptide may lack a tertiary or quaternary structure. A wide range of biopolymers are comprised within the term "protein". For example, the protein may refer to a therapeutic protein or non-therapeutic protein, comprising antibodies, aptamers, fusion proteins, Fc fusion proteins, PEGylated proteins, synthetic polypeptides, protein fragments, lipoproteins, enzymes, hormones, immunogenic proteins (e.g., as used in vaccines), structural peptides, peptide drugs. According to one embodiment of the present invention, the protein may be one or more selected from a group consisting of bovine serum albumin (BSA) and immunoglobulin G (IgG), but is not limited thereto.

In the present invention, the protein microbeads can be provided as the protein microbeads themselves or in the form of a pharmaceutical composition, wherein the protein may be a therapeutic protein.

The pharmaceutical composition according to the present invention may further comprise a suitable carrier, excipient, and diluent which are commonly used in the preparation of pharmaceutical compositions. The excipient may be, for example, one or more selected from the group consisting of a diluent, a binder, a disintegrant, a lubricant, an adsorbent, a humectant, a film-coating material, and a controlled release additive.

As the carrier, the excipient, and the diluent that may be comprised in the pharmaceutical composition according to the present invention, lactose, dextrose, sucrose, oligosaccharides, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil may be used.

The protein microbeads or the pharmaceutical composition comprising the same according to the present invention may be formulated into forms such as non-oral injections, sprays, inhalants, patches, sterile injection solutions, or aerosols, among other topical agents, according to common methods.

The topical agent (mucosa) according to the present invention may have a formulation such as creams, gels, patches, sprays, ointments, plasters, lotions, liniments, pastes, or cataplasmas.

The ointment is manufactured according to a public or commonly used prescription. For example, one or more active ingredients are levigated or melted in a base. The ointment base is selected from a public or commonly used one. For example, it is made by using alone or mixing two or more selected from advanced fatty acids or advanced fatty acid esters (myristic acid, palmitic acid, stearic acid, oleic acid, myristic acid ester, palmitic acid ester, stearic acid ester, oleic acid ester, etc.), waxes (beeswax, hard wax, ceresin, etc.), surfactants (polyoxyethylenealkyletheresters, etc.), advanced alcohols (cetanol, stearyl alcohol, cetostearyl alcohol, etc.), silicone oils (dimethylpolysiloxanes, etc.), hydrocarbons (anhydrous vaseline, white vaseline, refined lanolin, liquid paraffin, etc.), glycols (ethylene glycol, diethylene glycol, propylene glycol, polyethylene glycol, macrogol, etc.), plant oils (castor oil, olive oil, sesame oil, turpentine oil), animal oils (mink oil, egg yolk oil, squalane, squalene, etc.), water, absorption enhancers, and anti-inflammatories. It may also contain additional moisturizers, preservatives, stabilizers, antioxidants, and fragrances.

The gel is manufactured according to a public or commonly used prescription. For example, one or more active ingredients are melted in a base. The gel base is selected from a public or commonly used one. For example, it is made by using alone or mixing two or more selected from low-grade alcohols (ethanol, isopropyl alcohol, etc.), gelling agents (carboxymethylcellulose, hydroxyethylcellulose, hydroxypropylcellulose, ethylcellulose, etc.), neutralizers (triethanolamine, diisopropanolamine, etc.), surfactants (polyethylene glycol monostearate, etc.), gums, water, absorption enhancers, and anti-inflammatories. It may also contain additional preservatives, antioxidants, and fragrances.

The cream is manufactured according to a public or commonly used prescription. For example, one or more active ingredients are melted or emulsified in a base. The cream base is selected from a public or commonly used one. For example, it is made by using alone or mixing two or more selected from advanced fatty acid esters, low-grade alcohols, hydrocarbons, diols (propylene glycol, 1,3-butylene glycol, etc.), advanced alcohols (2-hexyldecanol, cetanol, etc.), emulsifiers (polyoxyethylene alkyl ether series, fatty acid ester series, etc.), water, absorption enhancers, and anti-inflammatories. It may also contain additional preservatives, antioxidants, fragrances, etc.

Liniments are manufactured according to public or commonly used prescriptions. For example, one or more active substances are selected from water, alcohol (ethanol, polyethylene glycol, etc.), higher fatty acids, glycerin, soap, emulsifiers, suspending agents, etc., and they are dissolved, suspended, or emulsified alone or in a combination of two or more. It may also contain preservatives, antioxidants, fragrances, etc.

Injections according to the present invention may include: solvents such as distilled water for injection, a 0.9% sodium chloride solution, Ringer's solution, a dextrose solution, a dextrose+sodium chloride solution, PEG, lactated Ringer's solution, ethanol, propylene glycol, non-volatile oil-sesame oil, cottonseed oil, peanut oil, soybean oil, corn oil, ethyl oleate, isopropyl myristate, and benzene benzoate; cosolvents such as sodium benzoate, sodium salicylate, sodium acetate, urea, urethane, monoethylacetamide, butazolidine, propylene glycol, the Tween series, amide nicotinate, hexamine, and dimethylacetamide; buffers such as weak acids and salts thereof (acetic acid and sodium acetate), weak bases and salts thereof (ammonia and ammonium acetate), organic compounds, proteins, albumin, peptone, and gums; isotonic agents such as sodium chloride; stabilizers such as sodium bisulfite ($NaHSO_3$) carbon dioxide gas, sodium metabisulfite ($Na_2S_2O_5$), sodium sulfite ($Na_2SO_3$), nitrogen gas ($N_2$), and ethylenediamine tetraacetic acid; sulfating agents such as 0.1% sodium bisulfide, sodium formaldehyde sulfoxylate, thiourea, disodium ethylenediaminetetraacetate, and acetone sodium bisulfite; a pain relief agent such as benzyl alcohol, chlorobutanol, procaine hydrochloride, glucose, and calcium gluconate; and suspending agents such as sodium CMC, sodium alginate, Tween 80, and aluminum monostearate.

In the inhalants of the present invention, an aerosol, an inhalable powder, or an inhalable liquid is included, and this inhalable liquid may be in a form that is dissolved or suspended in water or another suitable medium for use. These inhalants are manufactured in accordance with the methods disclosed. For example, in the case of inhalable liquids, preservatives (benzalkonium chloride, parabens, etc.), colorants, buffering agents (sodium phosphate, sodium acetate, etc.), tonicity agents (sodium chloride, concentrated glycerin, etc.), viscosity increasers (carboxyvinyl polymers, etc.), absorption promoters, etc., are appropriately selected as needed and formulated.

In the case of inhalable powders, excipients (stearic acid and its salts, etc.), binders (starch, dextrin, etc.), bulking agents (lactose, cellulose, etc.), colorants, preservatives (benzalkonium chloride, parabens, etc.), absorption promoters, etc., are appropriately selected as needed and formulated.

When administering the inhalable liquid, a common sprayer (atomizer, nebulizer) is used, and when administering the inhalable powder, a common powder drug inhalation device is used.

Aerosols, inhalants, sprays may generally contain stabilizers such as sodium bisulfate other than commonly used diluents, and tonicity-enhancing buffers, for example, sodium chloride, sodium citrate or citric acid, as tonicity agents.

In the deodorant of the present invention, additional components such as absorption promoters, solvents, solubilizing aids, adhesive polymers, etc., can be included.

As the solvent, an alkali metal hydroxide aqueous solution; alkanolamine selected from triethanolamine, diethanolamine, ethanolamine, isopropanolamine, diisopropanolamine; alkylamine selected from isopropylamine, diisopropylamine, triethylamine, diethylamine, and ethylenediamine can be used alone or in a mixture of two or more. The alkali metal hydroxide may be selected from sodium hydroxide, potassium hydroxide, or lithium hydroxide.

As the solubilizing aid, ethanol, isopropyl alcohol, methylpropanol, methylene chloride, methyl ethyl ketone, propylene glycol, polyethylene glycol, dipropylene glycol, diethylene glycol, diethylene glycol monoethyl ether, glycerol, acetylacetone, dimethyl sulfoxide, dimethylacetamide, dimethylformamide, N-alkyl pyrrolidin, and Tween 80 may be used alone or in a mixture of two or more.

As the absorption promoter, lauryl ether including polyoxyethylene lauryl ether; fatty acid alcohol containing oleyl alcohol, stearyl alcohol; fatty acid selected from oleic acid, lauric acid, palmitic acid, stearic acid, caprynic acid, caprylic acid, and myristic acid; fatty acid ester including isopropyl myristate, propylene glycol caprylate, propylene glycol laureate, polyethylene glycol laureate, propylene glycol oleate; and fatty acid alkanoamide including 1-dodecylazacycloheptan-2-one, lauryl dimethanolamide may be used alone or in a mixture of two or more.

As the adhesive polymer, an acrylate copolymer, vinyl acetate-acrylate, acrylate-acrylamide copolymer, or a mixture thereof along with an acrylic resin may be used, and if necessary, a rosin resin, a polyterpene resin, a petroleum resin, a terpene phenol resin, a natural or synthetic rubber, and a silicone polymer may be used alone or in a mixture of two or more.

The protein microbeads or pharmaceutical composition comprising the same according to the present invention is administered in a pharmaceutically effective amount. In the present invention, "the pharmaceutically effective amount" refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields.

The protein microbeads or pharmaceutical composition comprising the same according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

The protein microbeads or pharmaceutical composition comprising the same according to the present invention may be administered to a subject via various routes. All administration methods can be predicted, and the pharmaceutical composition may be administered via, for example, subcutaneous injection, intraperitoneal injection, intravenous injection, intramuscular injection, space around the spinal cord (intrathecal) injection, administration via the mucosa, intrarectal insertion, intravaginal insertion, ocular administration, intra-aural administration, intranasal administration, inhalation, spraying via the mouth or nose, percutaneous administration, or the like.

The protein microbeads or pharmaceutical composition comprising the same according to the present invention is determined depending on the type of a drug, which is an active ingredient, along with various related factors such as a disease to be treated, administration route, the age, gender, and body weight of a patient, and the severity of diseases.

In the present invention, the term "therapeutic protein" refers to a protein having therapeutic effects, and may comprise mammalian proteins such as hormones and prohormones (for example, insulin and proinsulin, synthetic insulin, insulin analogues, glucagon, calcitonin, thyroid hormones (T3 or T4 or thyroid-stimulating hormone), parathyroid hormone, gastrin, cholecystokinin, leptin, luteinizing hormone, oxytocin, vasopressin, atrial natriuretic peptide, luteinizing hormone, growth hormone, growth hormone releasing factor, somatostatin, etc.); coagulation or anticoagulation factors (for example, tissue factor, von Willebrand factor, factor VIIIC, factor VIII, factor IX, protein C, plasminogen activator (urokinase, tissue plasminogen activator, thrombin); cytokines, chemokines, and inflammatory mediators (for example, tumor necrosis factor inhibitors); interferon; colony-stimulating factors; interleukins (for example, IL-1 to IL-10); growth factors (for example, vascular endothelial growth factor, fibroblast growth factor, platelet-derived growth factor, transforming growth factor, nerve growth factor, insulin-like growth factor, etc.); albumin; collagen and elastin; hemopoietic factors (for example, erythropoietin, thrombopoietin, etc.); bone inducing factors (for example, bone morphogenic protein); receptors (for example, integrin, cadherin, etc.); surface membrane proteins; transport proteins; regulatory proteins; antigenic proteins (for example, components of a virus that act as antigens, as in a vaccine). Furthermore, the therapeutic protein can comprise the entire complement of a protein that can be used as a pharmaceutical, for example, etanercept, denileukin diftitox, alefacept, abatacept, rinolacept, romiplostim, corifollitropin-alpha, belatacept, aflibercept, ziv-aflibercept, eftrenonacog-alpha, albiglutide, efraloctocog-alpha, dulaglutide and the like, which are fusion proteins, and it may also comprise monoclonal antibodies (for example, full length antibodies including an immunoglobulin Fc region), single chain molecules, dual-specificity and multi-specificity antibodies, diabodies, antibody-drug conjugates, antibody compositions having polyepitope specificity, and antibody fragments (for example, Fab, Fv, Fc, and F(ab')2), but is not limited thereto.

In the present invention, the term “organic solvent” refers to a material made up of organic material that dissolves other materials, and is characterized as a liquid phase material that does not dissolve well in water, is highly volatile, has high cleaning power, and has a specific odor. The organic solvent can be divided into hydrophilic organic solvents and hydrophobic organic solvents, and in the present invention, the organic solvent may be a hydrophobic organic solvent that does not mix with water, with a water saturation fraction (r) value of 0.5 or less, for example, the hydrophobic organic solvent may be one or more selected from a group consisting of carbonates, esters, ethers, ketones, alcohols, non-polar solvents, and isomers thereof, but is not limited thereto.

The carbonate-based solvent may comprise dimethyl carbonate (DMC), diethyl carbonate (DEC), dipropyl carbonate (DPC), methylpropyl carbonate (MPC), ethylpropyl carbonate (EPC), methylethyl carbonate (MEC), ethylene carbonate (EC), propylene carbonate (PC), butylene carbonate (BC), and the like. The ester-based solvent may comprise methyl acetate, ethyl acetate, n-propyl acetate, dimethyl acetate, methylpropionate, ethylpropionate, γ-butyrolactone, decanolide, valerolactone, mevalonolactone, caprolactone, and the like. The ether-based solvent may comprise dibutyl ether, tetraglyme, diglyme, dimethoxyethane, 2-methyltetrahydrofuran, tetrahydrofuran, and the like. The ketone-based solvent may comprise cyclohexanone and the like. Also, the alcohol-based solvent may comprise methanol, ethanol, propanol, butanol, pentanol, hexanol, heptanol, n-octanol, nonanol, decanol, isopropyl alcohol, and the like. The non-polar solvent may comprise nitriles such as R—CN (where R is a hydrocarbon group with 2 to 20 carbon atoms in a straight, branched, or cyclic structure, which may include double bond direction rings or ether bonds), amides such as dimethylformamide, dioxolanes such as 1,3-dioxolane, sulfolane and the like.

According to previous research (D. G. Lim, J. C. Lee, D. J. Kim, S. J. Kim, H. W. Yu, S. H. Jeong, Effects of precipitation process on the biophysical properties of highly concentrated proteins, Journal of Pharmaceutical Investigation, (2020) 1-11) that confirmed various precipitation conditions for generating stable and highly reversible protein precipitates using lysozyme, it was found that proteins showed high reversibility when dehydrated in non-aqueous organic solvents such as pentanol and n-octanol, but the form of the lysozyme microbeads did not show fine spheres. On the other hand, according to an embodiment of the present invention, when n-octanol was used, the form of the microbeads showed no crystals or impurities, and only microbeads of various sizes were observed, and compared to when pentanol was used, the protein showed higher reversibility, so in the present invention, the organic solvent may be n-octanol, but is not limited thereto.

In the present invention, the term “process stabilizer” refers to a substance used to improve the stability of protein microbeads in the process of preparing protein microbeads according to the present invention, which may be a diluent, a saccharide (sugar), a polyol, a salt, or a surfactant, and may be one or more selected from the group consisting of, for example, trehalose, sucrose, mannose, maltose, lactose, arabinose, xylose, ribose, rhamnose, galactose, glucose, mannitol, xylitol, erythritol, threitol, sorbitol, glycerol, L-gluconate, NaCl, CaCl, polysorbate 80 (PS80), polysorbate 20 (PS20), sorbitan trioleate, and tyloxapol, but is not limited thereto.

Trehalose, a non-reducing sugar, is often used as an osmolyte and protein stabilizer to reduce stress-induced aggregation in bulk solution and increase the stability of native folding (N. K. Jain, I. Roy, Effect of trehalose on protein structure, Protein Sci, 18 (2009) 24-36, N. K. Jain, I. Roy, Trehalose and protein stability, Curr Protoc Protein Sci, Chapter 4 (2010) Unit 4 9, S. Ohtake, Y. J. Wang, Trehalose: current use and future applications, Journal of pharmaceutical sciences, 100 (2011) 2020-2053), however, sugars and polyols like trehalose have been reported to accelerate protein aggregation during mixing (J Pharm Sci. 2012 August; 101(8):2702-19, J Pharm Sci. 2010 March; 99(3):1193-206). On the other hand, according to an embodiment of the present invention, when microbeads are produced using trehalose, the reversibility of the protein microbeads is found to be the highest as compared to using polysorbate 80 or NaCl, therefore, in the present invention, trehalose can be used as a process stabilizer, but is not limited thereto.

According to an embodiment of the present invention, the trehalose may be used at a concentration of 100 mM to 500 mM, 100 mM to 400 mM, 100 mM to 350 mM, 200 mM to 500 mM, 200 mM to 400 mM, 200 mM to 350 mM, or 300 mM, but is not limited thereto.

In the present invention, “microbeads” refer to protein precipitates that are produced when an emulsion prepared by mixing a protein with an organic solvent is dehydrated, where the diameter of the particles may be 0.1 μm to 50 μm, 0.1 μm to 30 μm, 0.1 μm to 20 μm, 0.1 μm to 10 μm, 1 μm to 50 μm, 1 μm to 30 μm, 1 μm to 10 μm, 1 μm to 5 μm, 5 μm to 50 μm, 5 μm to 30 μm, or 5 μm to 10 μm, and the average diameter may be 10 μm or less, but is not limited thereto.

In the present invention, “emulsion” refers to a mixed state where one or more immiscible liquids, oil phase or water phase, are dispersed in a micro-particle state (dispersed phase) in another liquid (dispersant), and depending on the particle size of the dispersed phase, it is typically divided into macro-emulsion, micro-emulsion, and nano-emulsion. If the emulsion is "water in oil" (W/O), oil is the continuous phase, and if it is "oil in water" (O/W), water is the continuous phase.

In the present invention, "dehydration" refers to the removal of water from the protein microbeads.

In the present invention, the step (a) may further comprise the step of emulsifying the protein through a Shirasu porous glass (SPG) membrane or a microchip before stirring the emulsion to make the particle shape and size of the protein microbeads uniform and to narrow the particle size distribution range, but is not limited thereto.

In the present invention, the SPG membrane may be used to overcome the problem that can cause inconsistent release profile and efficacy due to a wide particle size distribution of microbeads in conventional methods, and the pore diameter of the SPG membrane may be 1 μm to 10 μm, 1 μm to 7 μm, 1 μm to 5 μm, 1 μm to 4 μm, 2 μm to 4 μm, 2 μm to 5 μm, 2 μm to 7 μm, or 3 μm, but is not limited thereto.

In the present invention, the dehydration in the step (a) may be performed for seconds to 20 minutes, 10 seconds to 15 minutes, 10 seconds to 10 minutes, 10 seconds to 5 minutes, 10 seconds to 1 minute, 10 seconds to 40 seconds, 20 seconds to 40 seconds, 30 seconds to 20 minutes, 30 seconds to 10 minutes, 1 minute to 15 minutes, 1 minute to 20 minutes, 5 minutes to 15 minutes, 5 minutes to 20 minutes, 30 seconds, or 10 minutes, but is not limited thereto.

In the present invention, the step (a) may be carried out at 1° C. to 25° C., 1° C. to 20° C., 1° C. to 15° C., 1° C. to 10° C., 1° C. to 5° C., 3° C. to 25° C., 3° C. to 15° C., 3° C. to 10° C., 3° C. to 5° C., or 4° C., but is not limited thereto.

In the present invention, the protein in the step (a) may have an initial concentration of 1 mg/mL to 100 mg/mL, 1 mg/mL to 70 mg/mL, 1 mg/mL to 50 mg/mL, 1 mg/mL to 40 mg/mL, 1 mg/mL to 20 mg/mL, 5 mg/mL to 100 mg/mL, 5 mg/mL to 50 mg/mL, 5 mg/mL to 10 mg/mL, 10 mg/mL to 100 mg/mL, 10 mg/mL to 50 mg/mL, 10 mg/mL, or 50 mg/mL, but is not limited thereto.

In an embodiment of the present invention, in the step (a), the protein may be dehydrated by mixing n-octanol as an organic solvent at 30 mL to 60 mL, 30 mL to 55 mL, 30 mL to 50 mL, 35 mL to 60 mL, 35 mL to 55 mL, 35 mL to 50 mL, 40 mL to 60 mL, 40 mL to 55 mL, or 40 mL to 50 mL per 1 mL of the protein, but is not limited thereto.

In the present invention, the centrifugation in the step (b) may be performed at 5,000 rpm to 15,000 rpm, 7,000 rpm to 15,000 rpm, 9,000 rpm to 15,000 rpm, 5,000 rpm to 12,000 rpm, 7,000 rpm to 12,000 rpm, 9,000 rpm to 12,000 rpm, or 10,000 rpm for 10 seconds to 10 minutes, 10 seconds to 7 minutes, 10 seconds to 5 minutes, 10 seconds to 3 minutes, 30 seconds to 10 minutes, 30 seconds to 5 minutes, 30 seconds to 3 minutes, 1 minute to 5 minutes, 1 minute to 3 minutes, or 2 minutes, but is not limited thereto.

In the present invention, drying in the step (c) can be performed at a pressure of 50 mTorr to 300 mTorr, 50 mTorr to 250 mTorr, 50 mTorr to 220 mTorr, 50 mTorr to 150 mTorr, 50 mTorr to 100 mTorr, 100 mTorr to 300 mTorr, 100 mTorr to 250 mTorr, 100 mTorr to 220 mTorr, 150 mTorr to 300 mTorr, 150 mTorr to 250 mTorr, 150 mTorr to 220 mTorr, or 200 mTorr for 24 to 130 hours, 24 to 120 hours, 24 to 100 hours, 24 to 70 hours, 24 to 50 hours, 36 to 120 hours, 36 to 70 hours, 36 to 50 hours, or 48 hours at 25° C. to 40° C., 25° C. to 38° C., 25° C. to 36° C., 30° C. to 40° C., 30° C. to 38° C., 30° C. to 36° C., 32° C. to 40° C., 32° C. to 38° C., 32° C. to 36° C., or 35° C., but is not limited thereto.

In the present invention, "reversibility" means the property that if the motion of an object changes over time, it can return to the initial state of the object if time is reversed. According to the preparation method of the present invention, the reversibility of the protein microbeads may be 90% to 100%, for example, 90% or more, 91% or more, 92% or more, 93% or more, 94% or more, 95% or more, 96% or more, 97% or more, 98% or more, 99% or more, or 100%, but is not limited thereto.

In the present invention, "stability of protein microbeads" refers to the degree to which protein microbeads retain their structure, function, and/or biological activity when stored for a predetermined period. According to an embodiment of the present invention, the stability of the protein microbeads may be maintained under physical shock or high temperature stress, for example, the protein microbeads of the present invention may have stability at a temperature of 40° C. to 70° C., 40° C. to 65° C., 40° C. to 60° C., 40° C. to 57° C., 45° C. to 70° C., 45° C. to 65° C., 45° C. to 60° C., 45° C. to 57° C., 50° C. to 70° C., 50° C. to 65° C., 50° C. to 60° C., 50° C. to 57° C., or 55° C., but is not limited thereto.

In the present invention, "maintenance" refers to the state in which the stability of the protein microbeads is preserved or continues to exist.

In the present invention, "aggregation" refers to phase separation to non-dispersive form in the solution due to the attractive forces of colloidal particles dispersed in the solution, which is distinct from the concept of 'viscosity', which refers to the internal frictional force against the flow of a fluid, and 'precipitation', which refers to the formation of solid sediment by a solute dissolved in the solution. This includes the phenomenon where at least two proteins abnormally contact each other from a partially folded intermediate that exists in the folding and unfolding process of the protein, which may include the loss of the protein's intrinsic functional activity. In the case of protein aggregation, the induction of folding intermediates results in the exposure of the protein's hydrophobic regions, and the selective intermolecular interactions by these regions act as the main cause of protein precipitation. Factors affecting protein aggregation include protein (intermediate) concentration, protein amino acid sequence, pH, temperature, ionic strength of the solution, co-solutes (protein ligands, protein modifiers), molecular chaperones, etc.

In the present invention, "protein aggregation inhibition" includes reducing the amount of protein aggregation, slowing the rate of aggregation, or completely preventing aggregation.

Hereinafter, preferable examples and experimental examples will be provided to assist in understanding the present invention. However, the following examples and experimental examples are provided only to facilitate understanding of the present invention, and the content of the present invention is not limited thereto.

EXAMPLE

Example 1. Preparation of Materials

Gamma-globulin Inj was purchased from Green Cross (Gyeonggi, South Korea). It comprises 22.5 mg glycine, 5 mg sodium chloride (NaCl), and 165 mg human immunoglobulin G (IgG) per mL (total 2 mL) and two lots (lot numbers: 020A18001 and 020A19001) were used throughout the present invention. Before use, IgG was desalted in a 25 mM sodium acetate buffer at pH 4 using a Slide-A-Lyzer dilution cassette with a 10,000 molecular weight cutoff (Thermo Fisher Scientific, Rockford, IL, USA). Then, the final pH was measured using a digital pH meter (827 pH Lab, Metrohm, Switzerland). The dilution buffer was replaced three times at intervals of 8 hours, and the dilution was completed in a refrigerated state (i.e., at about 4° C. for 24 hours). After dilution, all samples were filtered through a sterile Spin-X 0.22 μm cellulose acetate centrifugal filter (Costar, Corning Incorp, Salt Lake, UT, USA) at 8,000 rpm for 2 minutes.

Bovine serum albumin (BSA) was purchased from Sigma-Aldrich (St. Louis, MO, USA), and before use, it was dissolved in a 25 mM sodium phosphate buffer at pH 7 and filtered through a 0.45 μm membrane composed of polytetrafluoroethylene (SH13P045NL, Hyundai Micro Co., Seoul, South Korea). Trehalose dihydrate, sodium chloride (NaCl), sodium acetate trihydrate, acetic acid, and pentanol were purchased from Sigma-Aldrich (St. Louis, MO, USA), and ethanol, isopropyl alcohol (IPA), and polysorbate 80 (PS80) were purchased from Daejung Chemicals (Gyeonggi, South Korea). n-Octanol was purchased from Junsei Chemical (Tokyo, Japan).

Example 2. SPG Membrane Emulsification

For emulsification, an internal pressure micro kit (IMK-20; MCtech, Siheung, South Korea) was used, featuring a dispersion emulsification system with a tubular Shirasu porous glass (SPG; pore diameter 3 μm, 20 mm×10 mm) membrane. Prior to the emulsification process, the SPG membrane was ignited at 500° C. for 10 hours in a muffle furnace (DF-2; Dae Heung Science, Ansan, South Korea) and treated with ultrasound for 4 hours in 1.75% (v/v) organosilicon resin (KP-18C; Shin-Etsu Chemical Co., Tokyo, Japan) to convert it into a hydrophobic membrane. This was dried in an oven at 60° C. for 90 minutes, and then re-treated with ultrasound in n-octanol for 10 minutes to degas it. The hydrophobized SPG membrane was then secured with an O-ring (AN-008; MCtech, Siheung, South Korea) and screwed onto the membrane module. The dispersion tank inside the SPG membrane was filled with the protein solution, and the continuous phase outside the SPG membrane was filled with n-octanol. The external pressure type micro kit was connected, and the $N_2$ gas was removed at a pressure of 50 kPa and the protein solution was discharged for 10 seconds.

Example 3. Protein Dehydration and Vacuum Drying Process in Organic Solvent

Protein dehydration was performed by vortexing (VM-10, Daihan Scientific Co., Seoul, Republic of Korea) a water-in-oil (W/O) emulsion consisting of a protein solution in four alcohols (ethanol, IPA, pentanol, and n-octanol). In the case of the non-SPG method, the protein solution was simply pipetted into the alcohol. 4.5 mL ethanol, 4.5 mL IPA, 10.71 mL pentanol, and 23.4 mL n-octanol were used to dehydrate 0.5 mL of the protein solution. As ethanol and IPA can be mixed with water, the protein solution was simply mixed at a 1:9 ratio, but for rapid dehydration, pentanol and n-octanol were calculated based on a fixed water saturation fraction (I) of 0.5. The volume V. of the protein solution was calculated according to the following Mathematical Equation 1.

$$V_w = f \times V_s \times C_s \times \rho \quad \text{[Mathematical Equation 1]}$$

Where f is the desired water saturation part, $V_s$ is the volume of the organic solvent, $C_s$ is the water solubility in the organic solvent (g of water/solvent), and ρ is the density of the organic solvent. To collect the precipitate, the emulsion was centrifuged for 2 minutes at 10,000 rpm, the sample was filled with ethanol after the supernatant was removed, and this process was repeated twice. To remove the existing solvent, the final extract was dried in a freeze dryer equipped with a cold trap (LP-20; Ilshin Biobase, Yangju, Republic of Korea) set to −80° C. The initial vacuum pressure was set to 57 mTorr at 25° C. for 48 hours, and then adjusted to 200 mTorr at 35° C. for 48 hours.

Example 4. Fluid Imaging (FI) Analysis

The particle concentration and images of protein microbeads were obtained using a Flowcam 8100 device equipped with a 10× zoom camera (Fluid-imaging Technologies, ME, USA). For sample preparation, 3 mg of IgG microbeads were dispersed in 1 mL of ethanol as a stock and diluted 50 times. Prior to each measurement, the deionized water was evaluated, followed by ethanol to verify the cleanliness of the fluid path and flow cell. Values less than 100 particles/mL were considered acceptable background values. For each measurement, 1 mL of diluted solution was loaded, and 0.2 mL was used for system priming. Then, data for the subsequent 0.2 mL were acquired at a flow rate of 0.1 mL/min. The smallest measured particle size was 1 μm, and particle sizes were presented as equivalent spherical diameters (ESD).

The averages and standard deviations were obtained from three individual measurements for each sample. Analysis was performed using the Visual Spreadsheet software (version 4.17.14) provided with the device.

Example 5. Size Exclusion Chromatography (SEC)

Size exclusion chromatography was performed using an Agilent HPLC 1260 (Agilent, Santa Clara, CA, USA) equipped with a diode array detector at a UV 745 wavelength of 280 nm. The used column was a TSKgel G3000SWXL SEC column (TOSOH Bioscience, King of Prussia, PA, USA) of 300 mm length and a pre-filter (Trident™ high-pressure inline filter, Restek, Bellefonte, PA, USA). The mobile phase for IgG was a thrice-concentrated phosphate-buffered saline (PBS) at a flow rate of 0.5 mL/min, and 20 μL was injected. Further, a 50 mM sodium phosphate buffer solution at pH 7 containing 300 mM NaCl at a flow rate of 1 mL/min was used as the mobile phase for BSA, and 10 μL was injected. All samples were filtered through a 0.22 μm cellulose acetate Spin-X centrifugal filter (Costar, Corning Incorporated, Corning, NY, USA) prior to analysis, and the reversibility of the protein was calculated using the following Mathematical Equation 2.

$$\text{Remaining monomer } \% = (A_s \div A_0) \times 100 \quad \text{[Mathematical Equation 2]}$$

where '$A_s$' is the area of the monomer peak in the given sample and '$A_0$' is the area of the monomer peak of the control group before microbeadization. All protein concentrations were adjusted to 5 mg/mL prior to measurement.

Example 6. Gas Chromatography (GC)

n-octanol and ethanol were quantified from the IgG microbeads prepared by an Agilent 7890A (Agilent, Santa Clara, CA, USA) equipped with a DB-624 ultra-inert (UI) column (inner diameter 60 m×0.25 mm×film thickness 1.4 μm) and a flame ionization detector (FID). Helium (130 mL/min split flow) was used as a carrier gas at a constant flow of 1.3 mL/min. The oven temperature program was set to start at 40° C. for 5 minutes, then increase to a maximum of 240° C. (with a 2-minute hold time) at a rate of 18° C./min. Before the sample measurement, the standard curve of ethanol was plotted at 6.35 μg/mL, 25.40 μg/mL, and 50.80 μg/mL, displaying $R^2$ linearity and a limit of quantification (LOQ) of 0.9999 and 2 μg/mL, respectively. Similarly, the standard curve of n-octanol was plotted at 69.69 μg/mL, 139.38 μg/mL, 278.75 μg/mL, and 1115.00 μg/mL, exhibiting $R^2$ linearity and a LOQ of 0.9998 and 14 μg/mL, respectively. 50 mg of IgG microbeads were quantified, and before each measurement, they were dissolved in 10 mL of deionized water.

Example 7. Dynamic Light Scattering (DLS)

The hydrodynamic size of the reconstituted BSA microbeads was measured using a Zetasizer Nano ZS90 (Malvern Instruments, Worcestershire, UK), and the BSA microbeads were reconstituted in the initial buffer solution at a concentration of 5 mg/mL. Each 1 mL sample was analyzed in a disposable cuvette (Kartell Labware, Milan, Italy) at a fixed angle of 90°, and the Zetasizer software version 7.11 was used to obtain parameters from the automatic correlation function.

Example 8. Differential Scanning Calorimetry (DSC)

The thermodynamic characteristics of the microbeads were evaluated using a Nano DSC (TA Instruments, New Castle, USA).

The IgG and BSA microbeads were reconstituted in the initial buffer at a concentration of 2 mg/mL, and the initial buffer was used as a reference for baseline subtraction. All samples were degassed prior to measurement and loaded into the sample capillary cell. The measurements were carried out from 25° C. to 95° C. at a heating rate of 1° C./min. The final thermogram was processed by subtracting the buffer baseline, and the transition melting temperature ($T_m$) was calculated using the Nanoanalyze software version 3.7 (TA Instruments, USA) provided with the equipment.

Example 9. Scanning Electronic Microscopy (SEM)

The shape of the IgG and BSA microbeads was observed by scanning a Scanning Electron Microscope (SEM) using an EM-30 SEM (COXEM, Daejeon, Korea) at an acceleration voltage of 20.0 kV. Prior to observation, the samples were coated with gold using an SPT-20 Ion Coater (COXEM, Daejeon, Korea).

Example 10. Optical Microscopy

The shapes of IgG and BSA in W/O emulsion were observed using an Olympus BX53 optical microscope (Olympus Corporation, Tokyo, Japan). The magnification was set at 20×, and for image analysis, an Olympus DP26 digital camera equipped with cellSens imaging software (Olympus Corporation, Tokyo, Japan) was used.

Example 11. Pharmacokinetic (PK) Analysis

Twenty male Sprague-Dawley rats, weighing between 210-230 g and aged 8 weeks, were divided into four groups (5 rats per group). The four groups represent IgG injection at low and high IgG concentration (i.e. 25 mg/kg and 50 mg/kg), as well as before and after microbeadification. The IgG microbeads were dissolved in a pH 4.0 acetate buffer to achieve 50 mg/mL and 100 mg/mL of IgG, and the IgG solution was diluted to the same concentration using injection water. The prepared samples were loaded in sterilized Injekt-F 1 mL syringe latex-free plastic syringe without silicone oil (Injekt) (B. Braun Medical Inc, Melsungen, Germany) with a 26-gauge needle, and each preparation was administered in the biceps femoris at 25 and 50 mg/kg doses. The volume of a single injection was approximately 100 μL per rat. Blood samples of 200 μL were collected from the subclavian vein using a syringe at 4, 8, and 24 hours, and at 2, 3, 5, 7, 9, 12, 14, 21, and 28 days after intramuscular administration. All samples were centrifugated at 17,000 rpm for 10 min to obtain serum and stored at −70° C. until analysis of a receptor-binding direct Enzyme-Linked Immunosorbent Assay (ELISA).

The present invention was approved by Institutional Animal Care and Use Committee of Chung-Ang University (No. 202000118). The serum IgG profiles were plotted using Origin Pro V. 2016 software (Originlab Corp., Northampton, MA, USA), and its PK parameters (i.e., $AUC_{0-28}$; area under the time-concentration curve from 0 to the last quantifiable time point, $C_{max}$; maximum observed peak concentration, Tmax; time to reach $C_{max}$, T112; terminal half-life) were calculated using non-compartmental analysis (Model 200, WinNonlin Pro, version 5.0.1; Pharsight Corporation; Mountain View, CA, USA). Based on previous experience with IgG, the $AUC_{0-28}$ was selected as the endpoint of the present invention. Comparison of PK parameters was performed using the paired t-test, and p-value<0.05 was considered statistically significant.

Example 12. ELISA

Diluted serum samples were analyzed for antibody concentration using a human IgG ELISA kit (MyBioSource, CA, USA, #MBS2511279). In this analysis, a recombinant antigen receptor specific to human IgG molecules was used as the capture reagent, and human IgG Fc conjugated to avidin-HRP (horseradish peroxidase) was used as the detection reagent. The detectable minimum concentration was 1.65 ng/mL.

Specifically, the microplates provided with the kit were pre-coated with antibodies specific to human IgG. Initially, 100 μL of the standard provided with the kit or diluted serum was loaded into each microplate well and then incubated at 37° C. for 90 minutes. Sequentially, 100 μL of biotinylated detection antibody specific to human IgG and HRP conjugate was added to each microplate well, followed by incubation at 37° C. for 60 minutes and 30 minutes, respectively, and free components were washed out 3 times with washing solution. Next, 90 μL of substrate solution was added, incubated at 37° C. for 15 minutes, and then 50 μL of stop solution was added to terminate the enzyme-substrate reaction. The optical density (OD) was measured at 450 nm using a SpectraMax M3 spectrophotometer (Molecular Devices, Sunnyvale, USA).

Example 13: Box-Plot Plotting and Calculation of Mean and Span Values

Box-chart plotting and calculation of mean values of the IgG microbeads were performed using Origin Pro V. 2016 software (Originlab Corp., Northampton, MA, USA). The accumulated information of the collected micron-size particles, including $D_{10}$, $D_{50}$, and $D_{90}$ values, was obtained from FI analysis, and the span value was calculated using the following Mathematical Equation 3.

$$\text{Span Value}=(D_{90}-D_{10})/D_{50} \quad \text{[Mathematical Equation 3]}$$

EXPERIMENTAL EXAMPLE

Experimental Example 1. The Effect of Organic Solvents on Protein Dehydration In the present invention, the initial key to success was to find a suitable solvent that could immediately dehydrate and precipitate the protein without an instability mechanism. The solvent should not mix with water and should not be the source of physical-chemical reactions to protein molecules. The method for preparing protein microbeads is divided into the following four steps: emulsification, dehydration (precipitation), collection, and drying. The method of simply dispersing the protein solution in the solvent without using SPG emulsification technique is called the 'non-SPG method', and it was utilized to find a suitable solvent for dehydration using BSA.

Figure 1B:
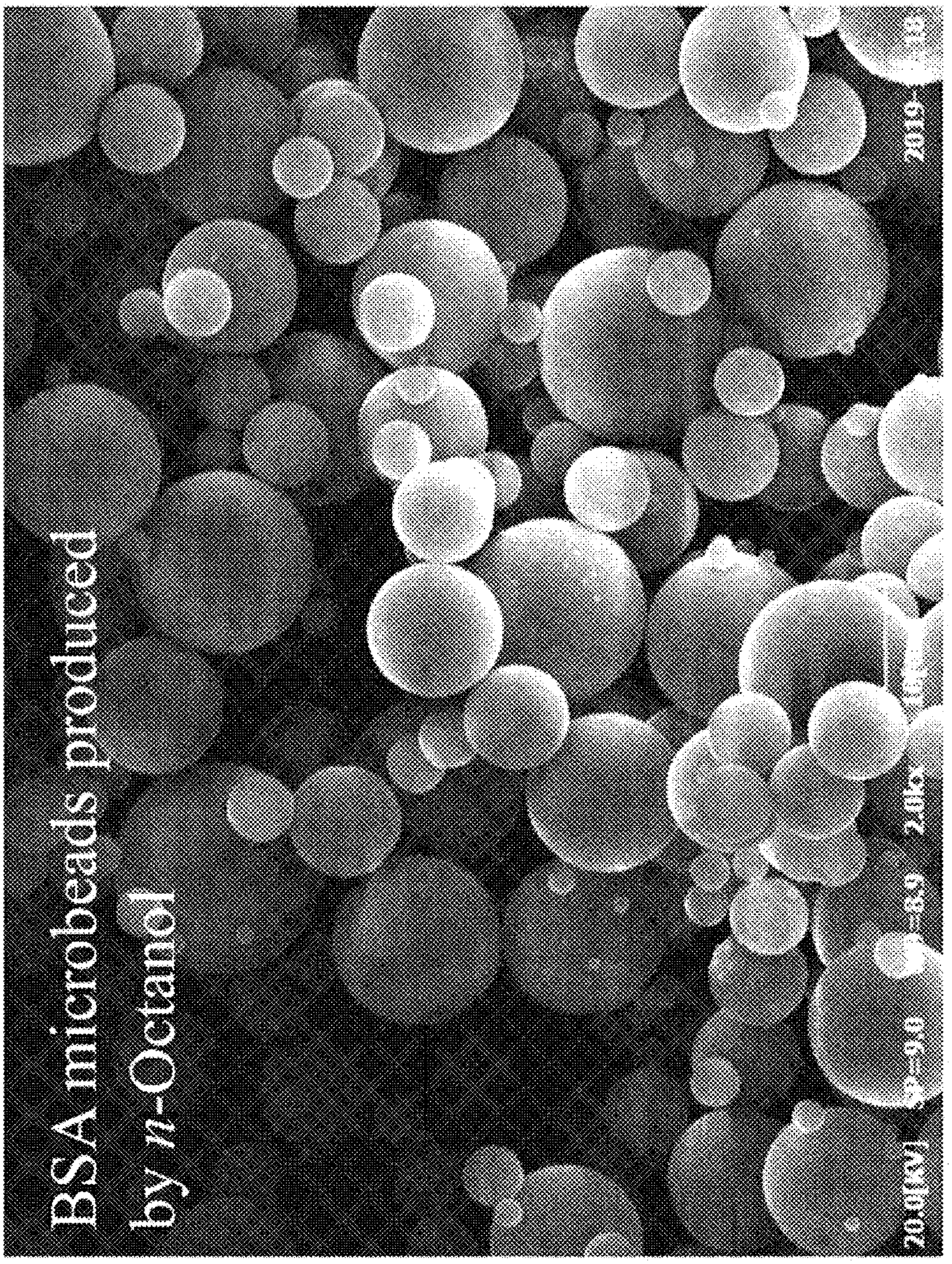
FIG. 1B is a drawing depicting a SEM image of BSA microbeads generated from n-octanol according to an embodiment of the present invention.
Figure 1C:
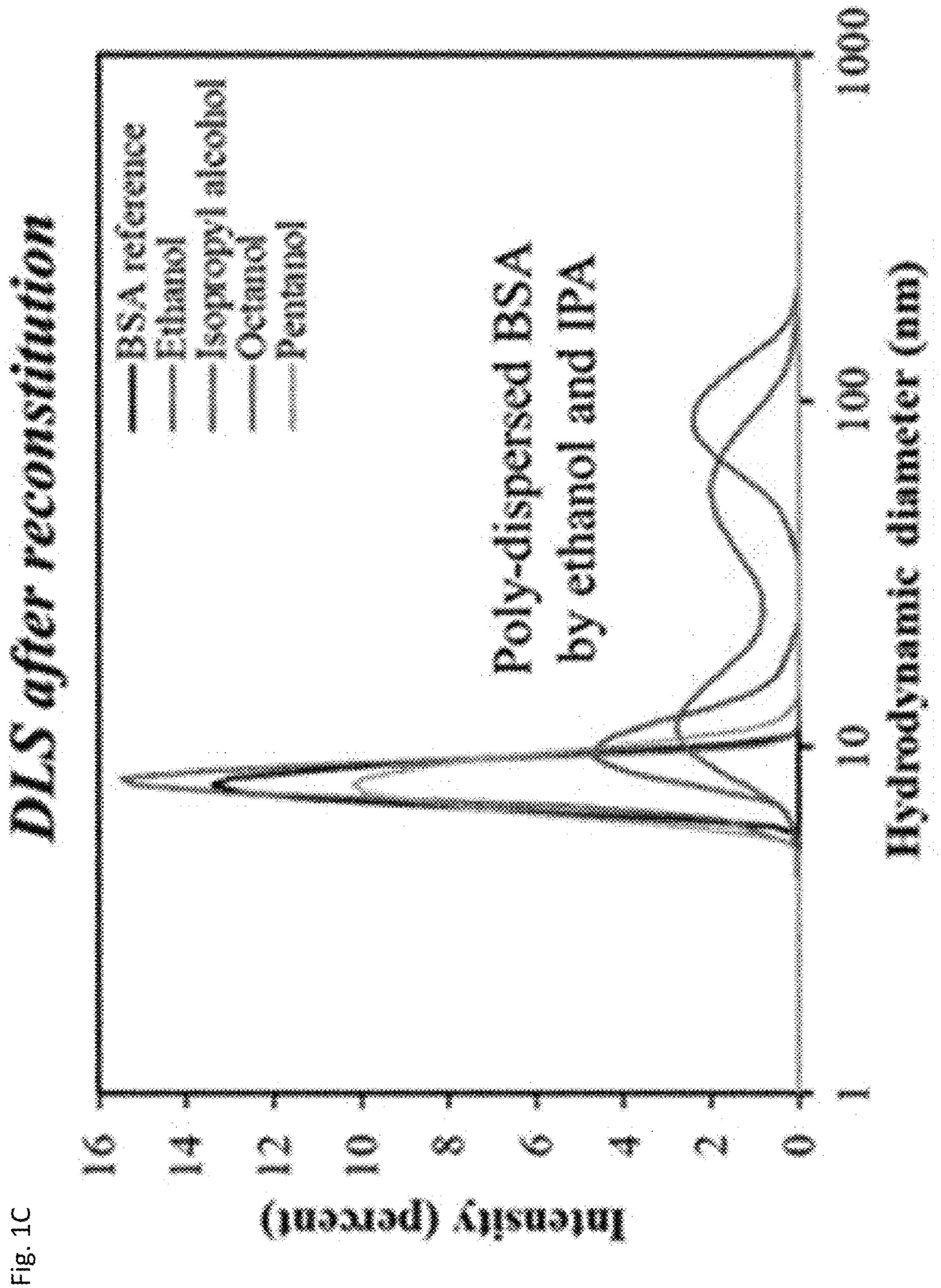
FIG. 1C to 1E illustrate the biophysical characteristics of BSA after reconstitution of BSA microbeads according to an embodiment of the present invention, where
Figure 1D:
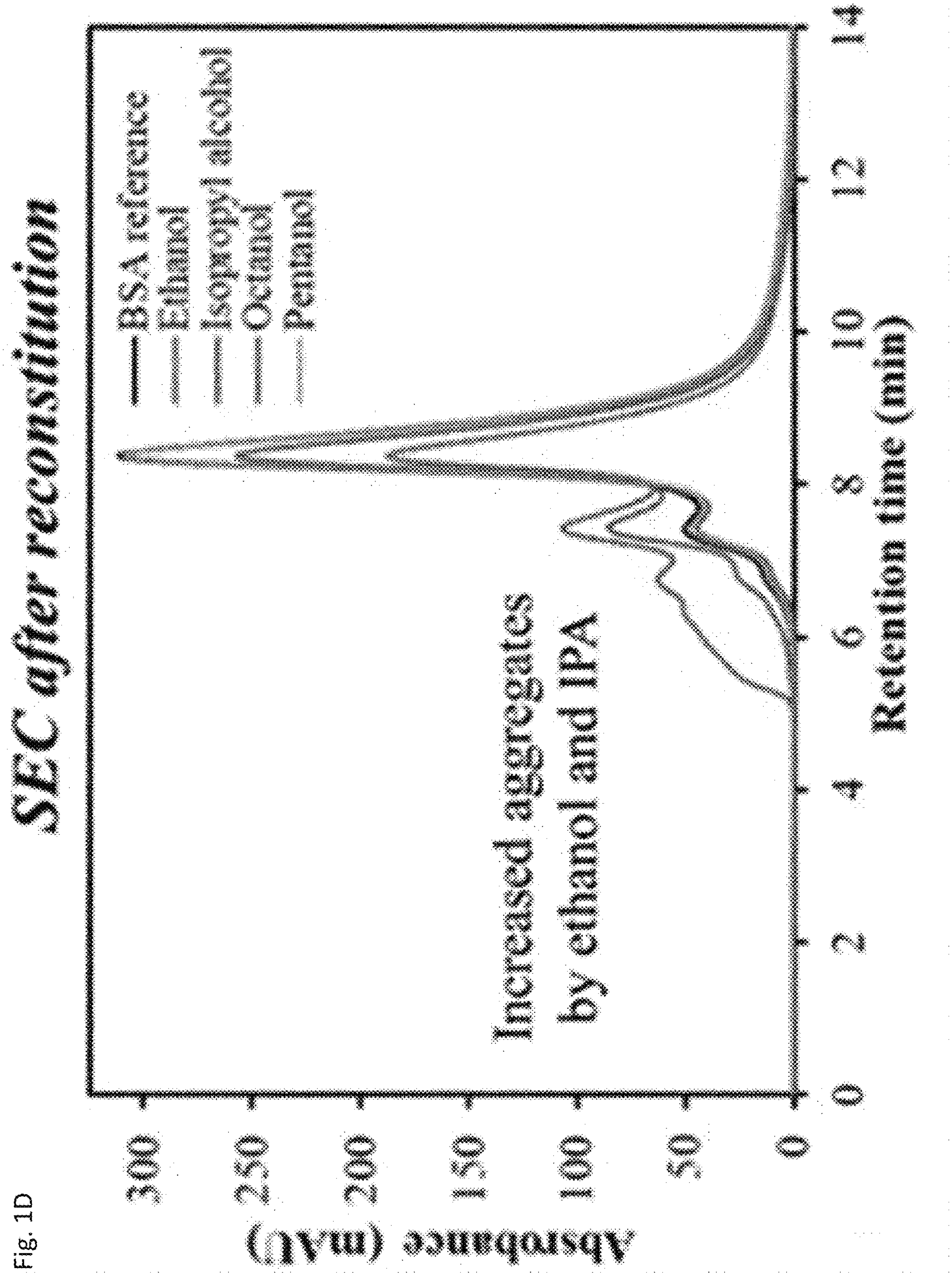
Figure 1E:
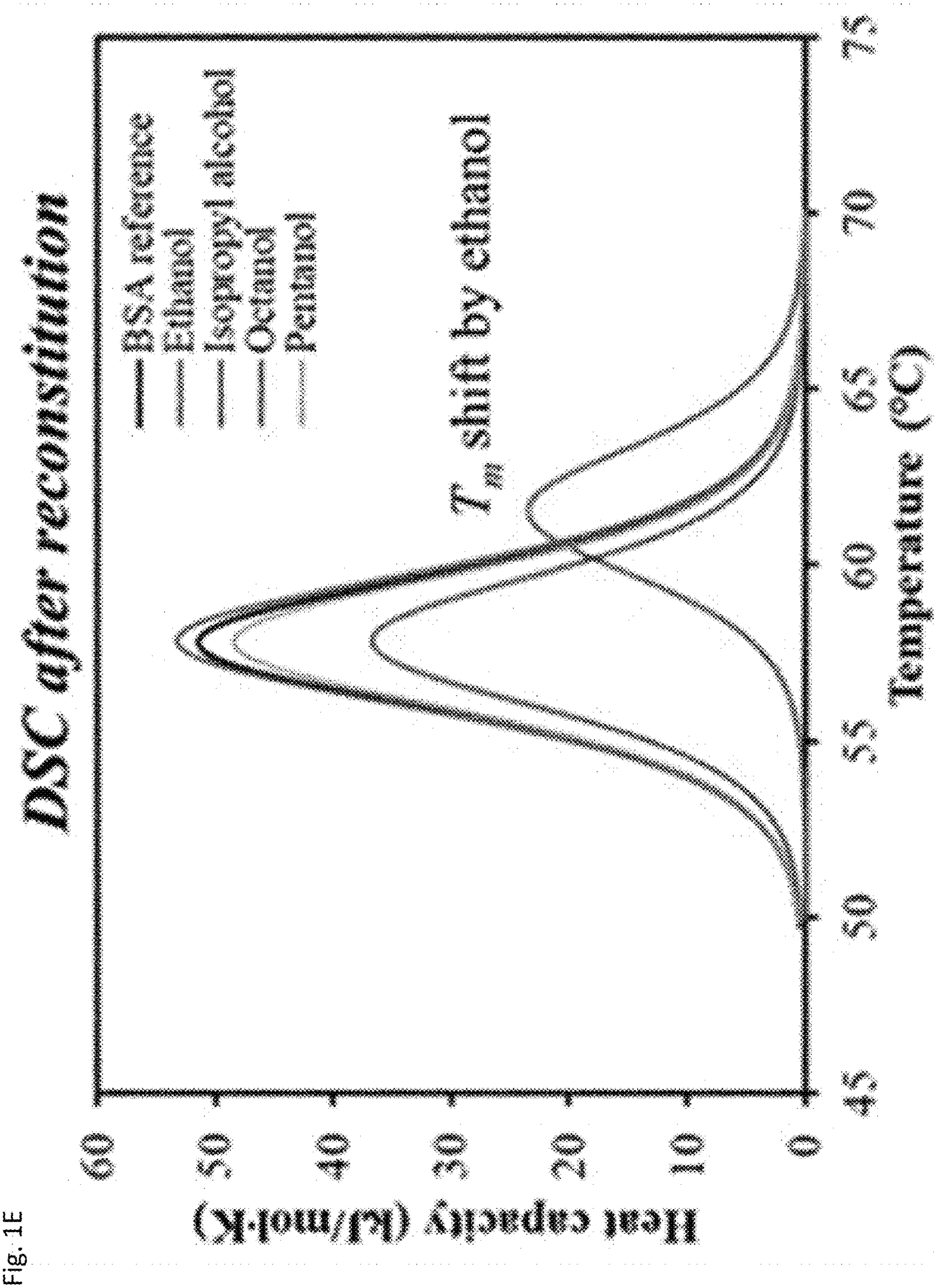

FIG. 1A is a schematic illustration of the non-SPG method in the preparation of BSA microbeads in order, and FIG. 1B represents a SEM image of BSA microbeads generated from n-octanol, while FIG. 1C to 1E represent the biophysical characteristics of BSA after the reconstruction of BSA microbeads.

Dehydrating 200 mg/mL BSA with simple vortexing for 30 seconds using ethanol, isopropyl alcohol (IPA), pentanol, and n-octanol as oil phase, resulted in highly monodispersed BSA observed after reconstruction when pentanol and n-octanol, known as non-miscible water solvents, were applied as dehydration solvents, as shown in FIG. 1C, confirmed through DLS results. However, when dehydrated in ethanol and IPA, polydispersed BSA was observed, and as a result, the formation of BSA aggregates (>20 nm) that could have formed during vortexing appeared.

Furthermore, when the SEC after the reconstruction of BSA microbeads was checked, as shown in FIG. 1D, ethanol induced the most amount of soluble aggregates, and checking the DSC thermogram, as shown in FIG. 1E, ethanol moved the $T_m$ to a higher temperature. The results indicated the formation of thermodynamically more favorable oligomers during dehydration in ethanol.

On the other hand, as shown in FIG. 1D, pentanol and n-octanol did not increase soluble aggregates but showed a higher reversible monomer, and the reversibility reached about 92% and 97%, respectively. Also, as shown in FIG. 1E, $T_m$ did not move, suggesting the same folding dynamics of BSA before and after dehydration.

In addition, as shown in FIG. 1B, the morphology of the BSA microbeads prepared from n-octanol did not show any crystals or impurities and showed only microbeads of various sizes. In previous studies, the morphology of lysozyme microbeads did not show fine spheres. Such difference was demonstrated by changing the shaker to vortex in the preparation method where the speed was increased from 30 rpm to 3,000 rpm and the duration was shortened from 30 minutes to 30 seconds, where the speed increased and the duration shortened, resulting in increased formation of microbeads.

Therefore, a vortexing protein solution in n-octanol was selected as a suitable dehydration process in the present invention and continued further in optimizing the process. On the other hand, ethanol was applied during microbeads collection and to decrease the level of n-octanol before drying process.

Experimental Example 2. Effect of SPG Membrane on IgG Microbead Formation

The SPG membrane emulsification technique was utilized to generate a smaller and narrower distribution of protein microbeads. The technique has been used for decades to precisely control the emulsification process when producing monodispersed emulsions of both O/W and W/O. The advantages of this technique include uniformity, scalability, and continuity of using pores of uniform size (0.1-50 μm). This technique has been used to manufacture microcapsules formed by chitosan or polymer to achieve controlled drug release profiles for biological preparations.

FIG. 2A to 2E illustrate a schematic setup of the SPG emulsification system to obtain fine IgG microbeads by dehydration, collection, and drying after the formation of IgG W/O droplets.

Figure 2A:
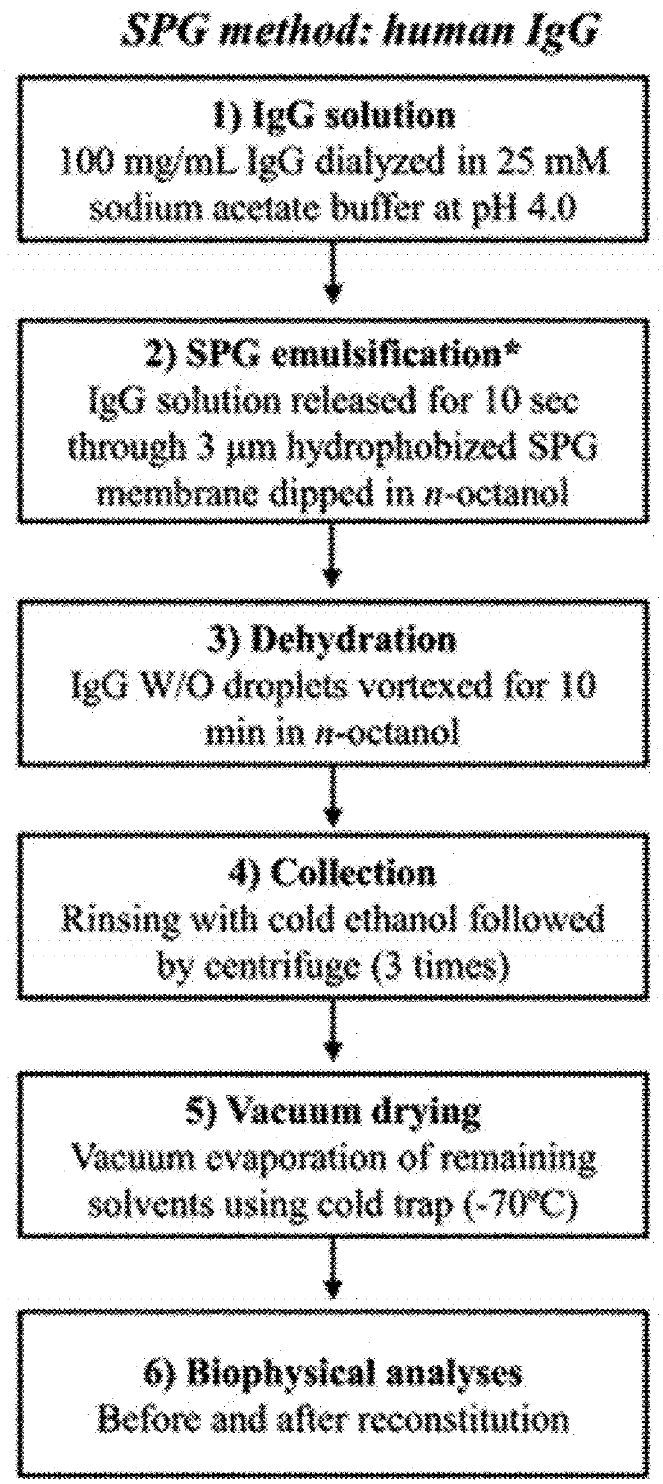
FIG. 2A is a schematic diagram sequentially illustrating an SPG method in the manufacturing of IgG microbeads according to an embodiment of the present invention.
Figure 2B:
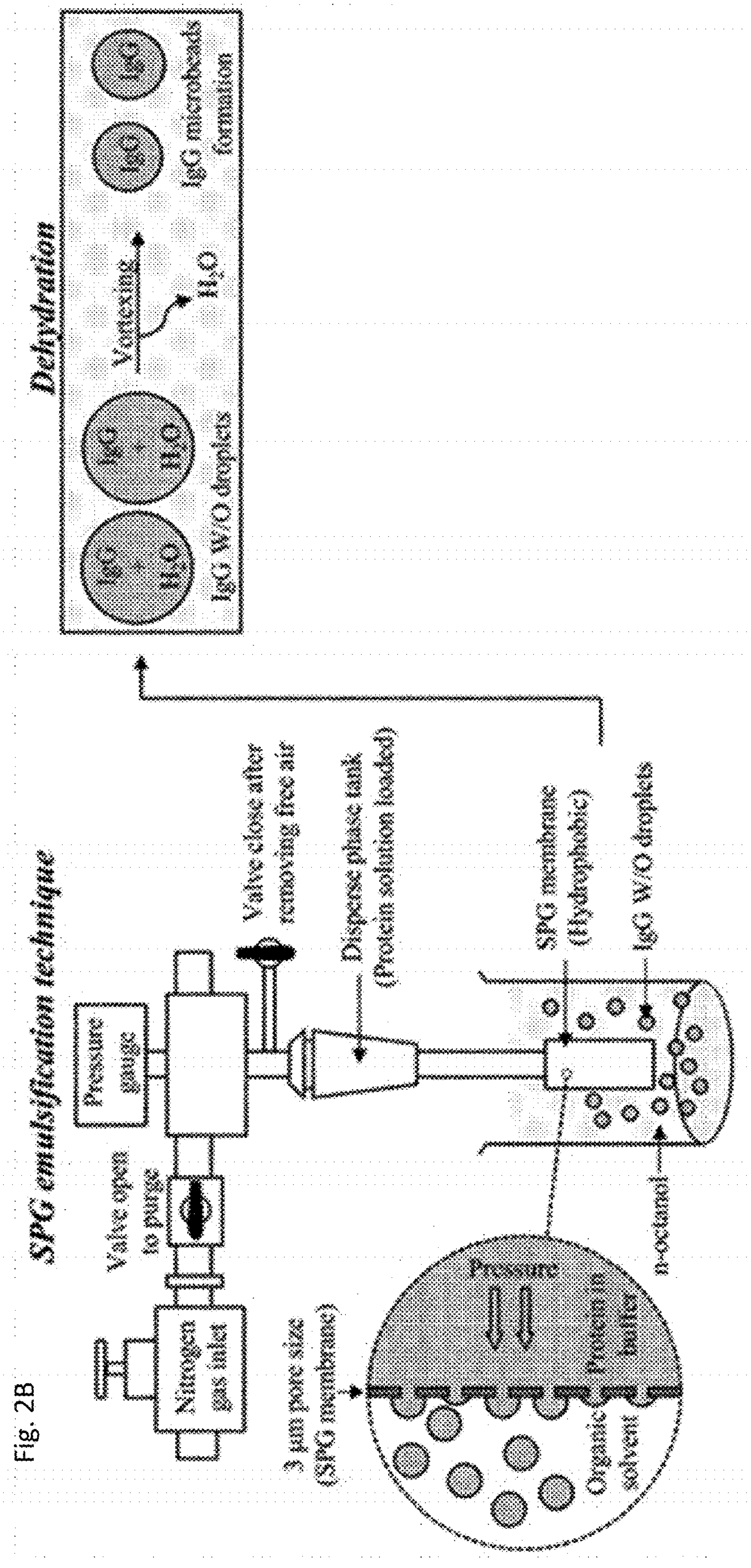
FIG. 2B is a drawing illustrating a schematic of a small-scale device for an SPG membrane emulsion system and the protein dehydration process using vortexing according to an embodiment of the present invention.
Figure 2C:
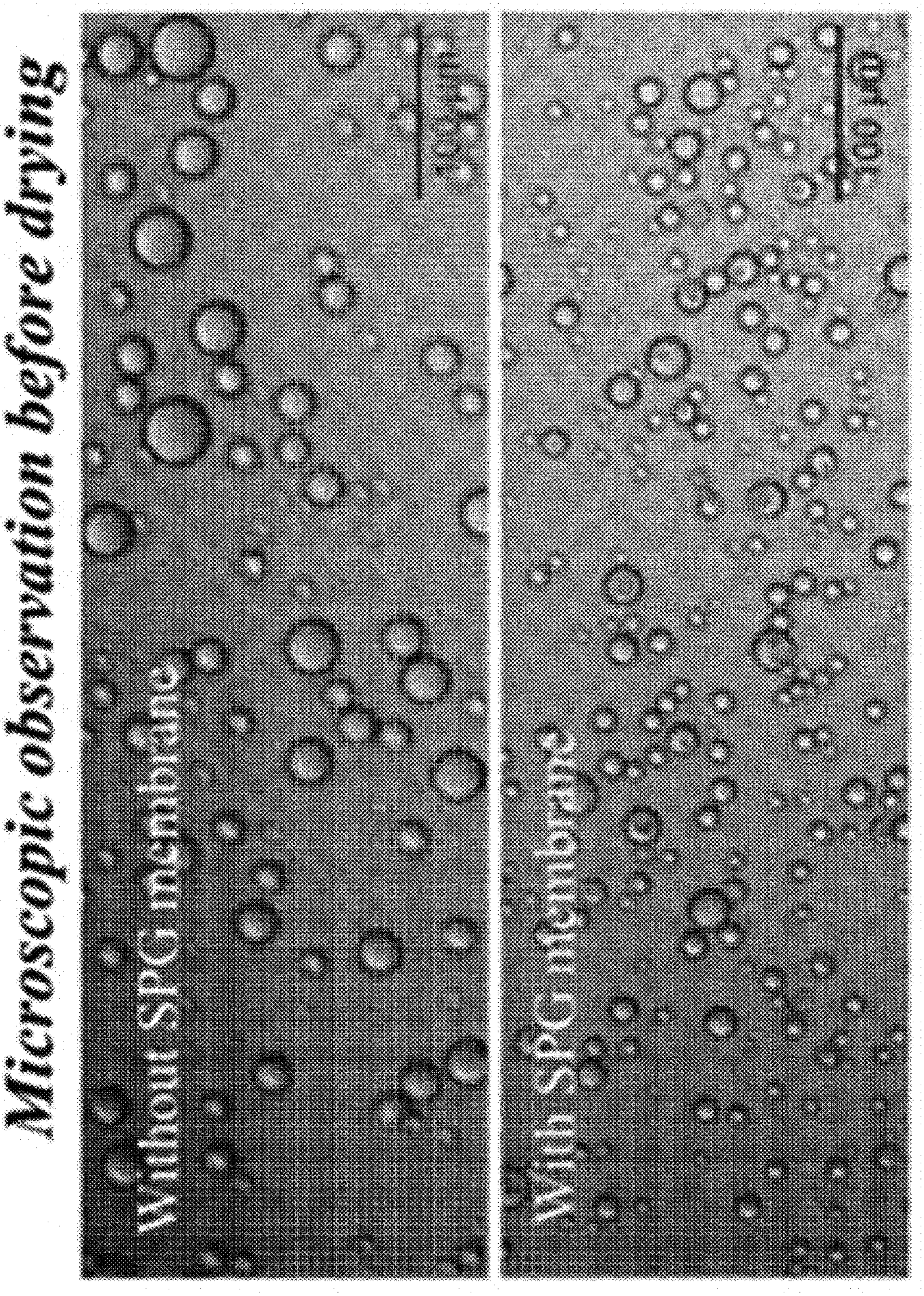
FIG. 2C is a drawing comparing the results of observing microbeads when non-SPG and SPG methods were used before vacuum drying according to an embodiment of the present invention.

FIG. 2A schematically illustrates in sequence a method of using the SPG membrane in the manufacturing of IgG microbeads, FIG. 2B illustrates a schematic of small-scale equipment for the SPG emulsification system and the subsequent protein 925 dehydration process using vortexing to remove water. FIG. 2C compares the microscopic observation results after 10 minutes of vortexing before drying in n-octanol with the non-SPG method and the SPG method, and FIG. 2D illustrates the observation results of the microbeads after vacuum drying using the non-SPG method and the SPG method.

A hydrophobic SPG membrane with a pore size of 3 μm was placed in n-octanol without stirring to prevent collapse or fusion of the water droplets during their discharge from the membrane. After the IgG W/O droplets were released from the SPG membrane, vortexing was performed for 10 minutes for dehydration to create IgG microbeads.

Figure 2D:
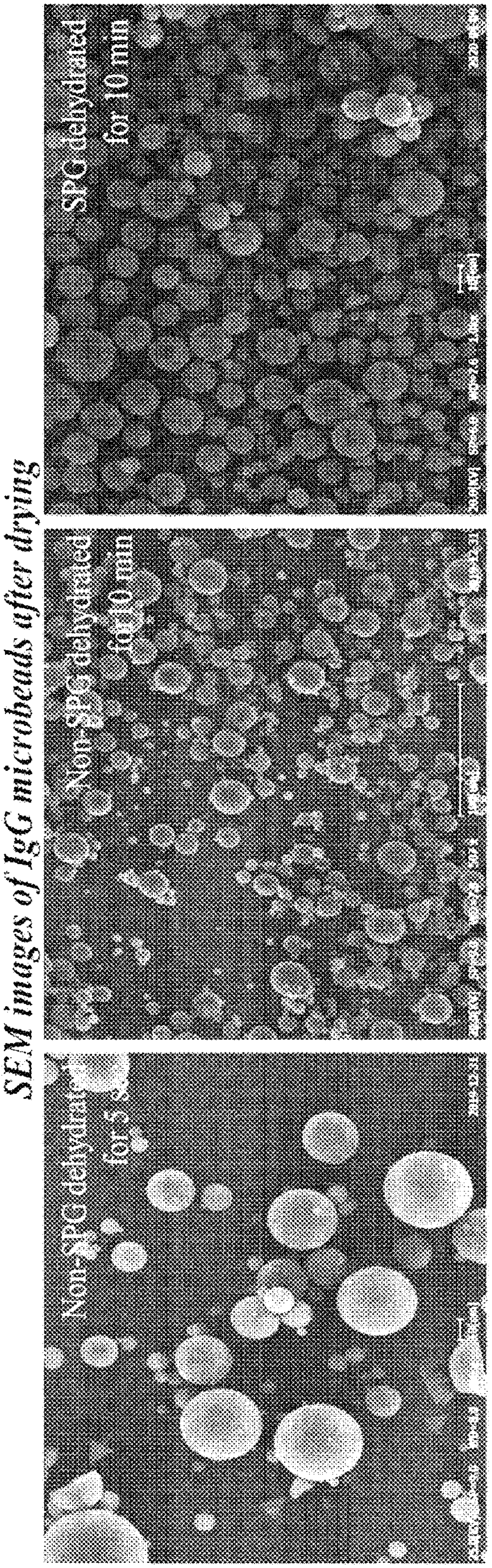
FIG. 2D is a drawing comparing the results of observing microbeads when non-SPG and SPG methods were used after vacuum drying according to an embodiment of the present invention.

The optical microscope observation results of the IgG W/O droplets discharged from the SPG membrane showed relatively smaller sizes than those without using the membrane, as shown in FIG. 2C, and such difference was consistent with the results in the IgG microbeads after the drying process in a vacuum chamber at 25° C. for 48 hours under a vacuum pressure of 57 mTorr, as shown in FIG. 2D.

Meanwhile, as shown in FIG. 2D, the IgG microbeads from the non-SPG method not only showed a few non-spherical microbeads, but also increased in size when vortexed for 5 seconds, suggesting a correlation of quality with dehydration time. Additional studies were conducted to evaluate process changes such as dehydration time, n-octanol temperature, pharmaceutical excipients, and drying conditions in relation to the quality and size distribution of IgG microbeads.

Experimental Example 3. Effect of Dehydration Time on IgG Microbead Formation The dehydration time ranged from 5 seconds to 45 minutes using a vortex, and the FI analysis was used to evaluate the size distribution of IgG microbeads. FI analysis allows real-time visualization of the morphology and quantification of subvisible particles larger than 1 μm without additional coating of the particles. The equivalent spherical diameter (ESD) is used when evaluating the size of the microbeads defined by the diameter of the sphere. Furthermore, it has been proven that the sensitivity and accuracy of particle quantification are more reliable than conventional light blocking methods. The analysis approach was used throughout the study to allow the use of FI in quality by design or process optimization related to product development.

After drying in a vacuum chamber, 3 mg of prepared IgG microbeads were dispersed in 1 mL of ethanol, and the microbeads were quantified without dissolution. To ensure higher sensitivity from particle numbers, it was diluted 50 times for FI analysis (i.e., <1,000,000 P/mL). The initial concentration of the IgG solution was set to 100 mg/mL.

Figure 3A:
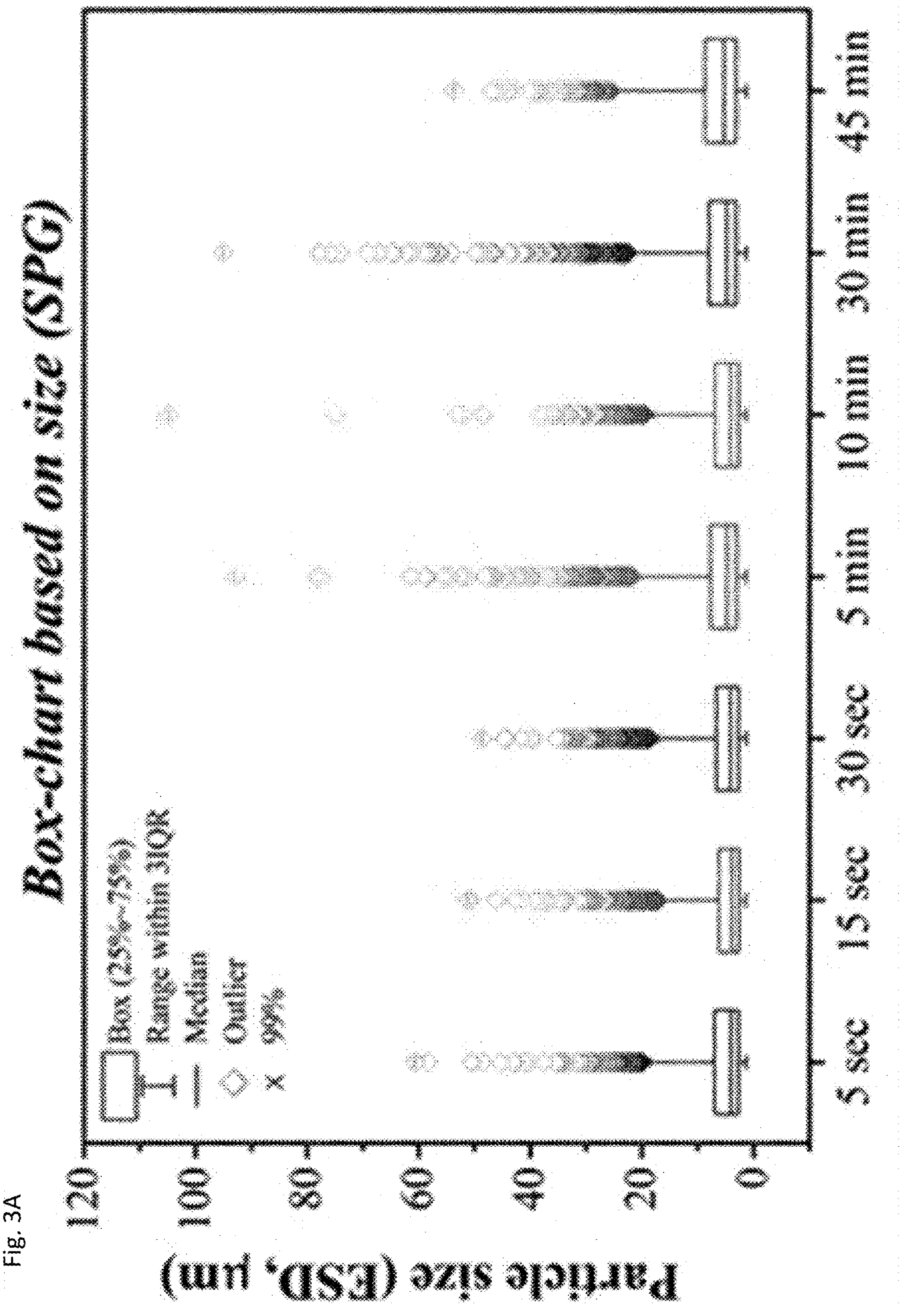
FIG. 3A is a drawing illustrating the particle size distribution based on a box-chart depending on the dehydration time of IgG microbeads manufactured by the SPG method according to an embodiment of the present invention.
Figure 3B:
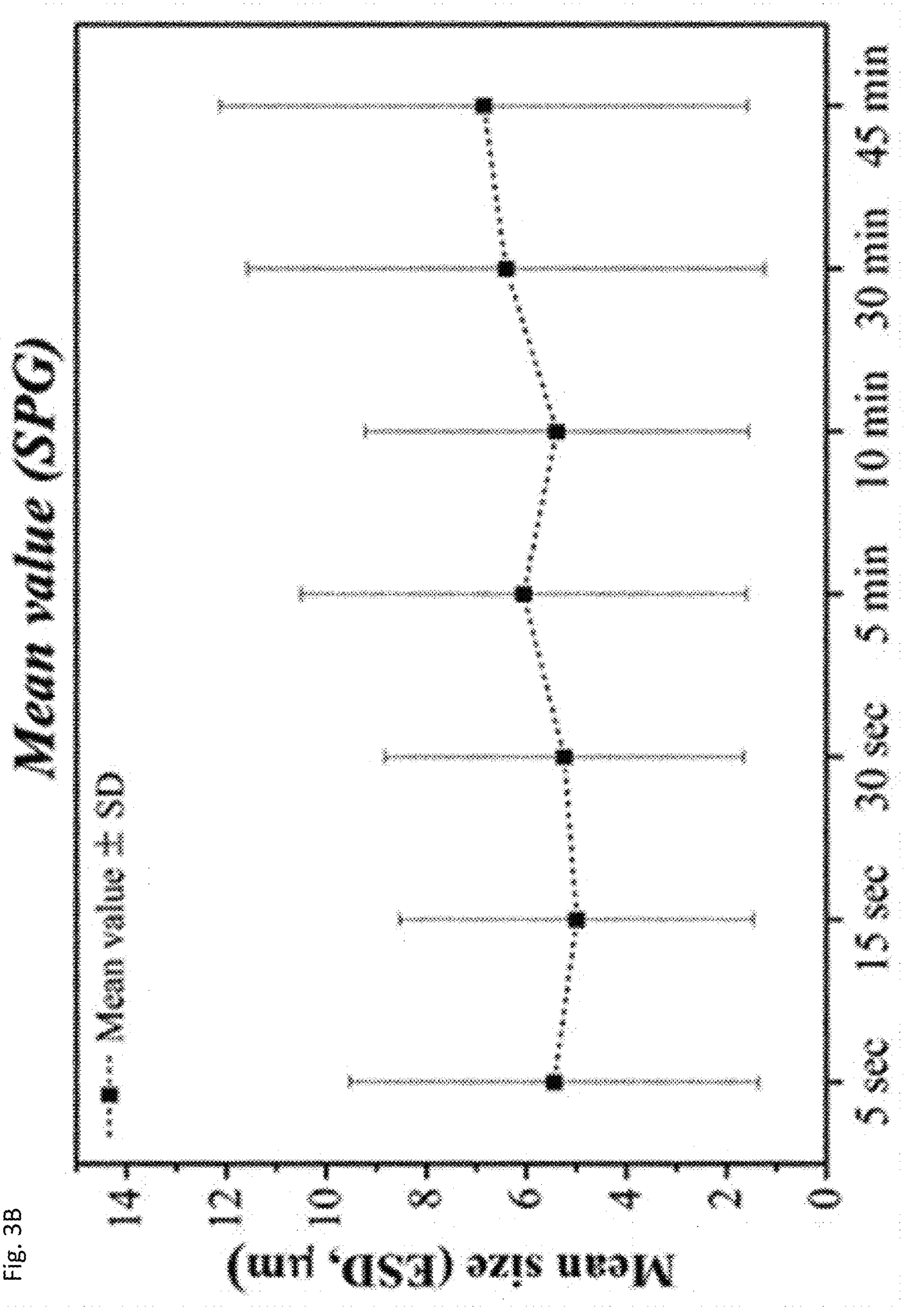
FIG. 3B is a drawing illustrating the average particle size depending on the dehydration time of IgG microbeads manufactured by the SPG method according to an embodiment of the present invention.
Figure 3C:
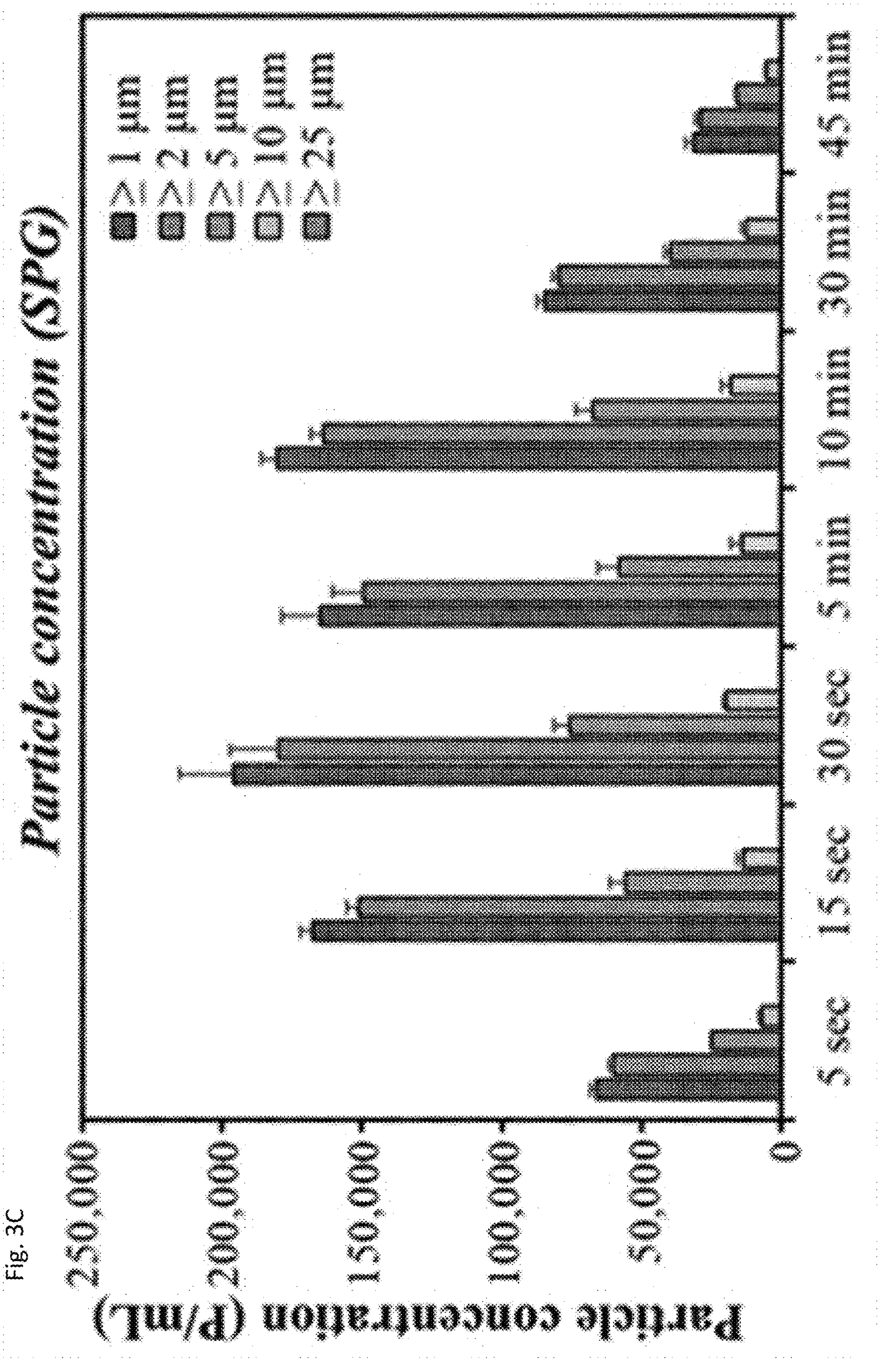
FIG. 3C is a drawing illustrating the particle concentration according to the dehydration time of IgG microbeads manufactured by the SPG method according to an embodiment of the present invention.

FIG. 3A to FIG. 3C represent the size distribution of IgG microbeads prepared by SPG methods with different dehydration times, shown respectively as particle size based on a box-chart (FIG. 3A), mean value (FIG. 3B), and particle concentration (FIG. 3C).

As a result, 75% of the IgG microbeads were confirmed to be less than 10 μm, and 99% were less than 20 μm in all prepared samples. The mean values of IgG microbeads with dehydration times of 5 seconds, 15 seconds, and 30 seconds were 5.45 μm, 4.99 μm, and 5.24 μm, respectively. Also, the mean values for extended times such as 5 minutes, 10 minutes, 30 minutes, and 45 minutes were 6.06 μm, 5.39 μm, 6.40 μm, and 6.86 μm, respectively. Excluding 10 minutes, the mean value increased as outliers of approximately 20 μm or more.

Figure 3D:
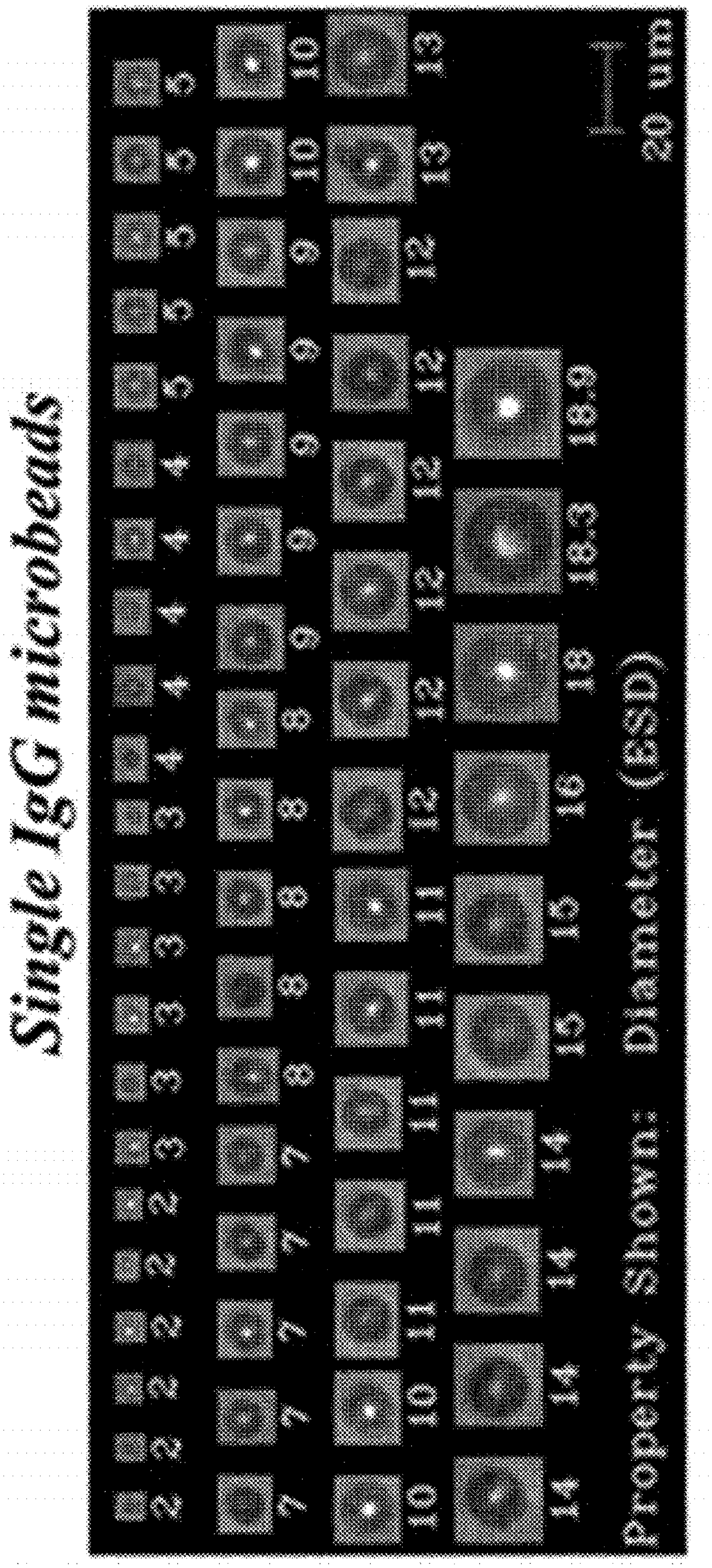
FIG. 3D is a drawing illustrating the results of identifying the FI image of a single IgG microbead according to an embodiment of the present invention.
Figure 3E:
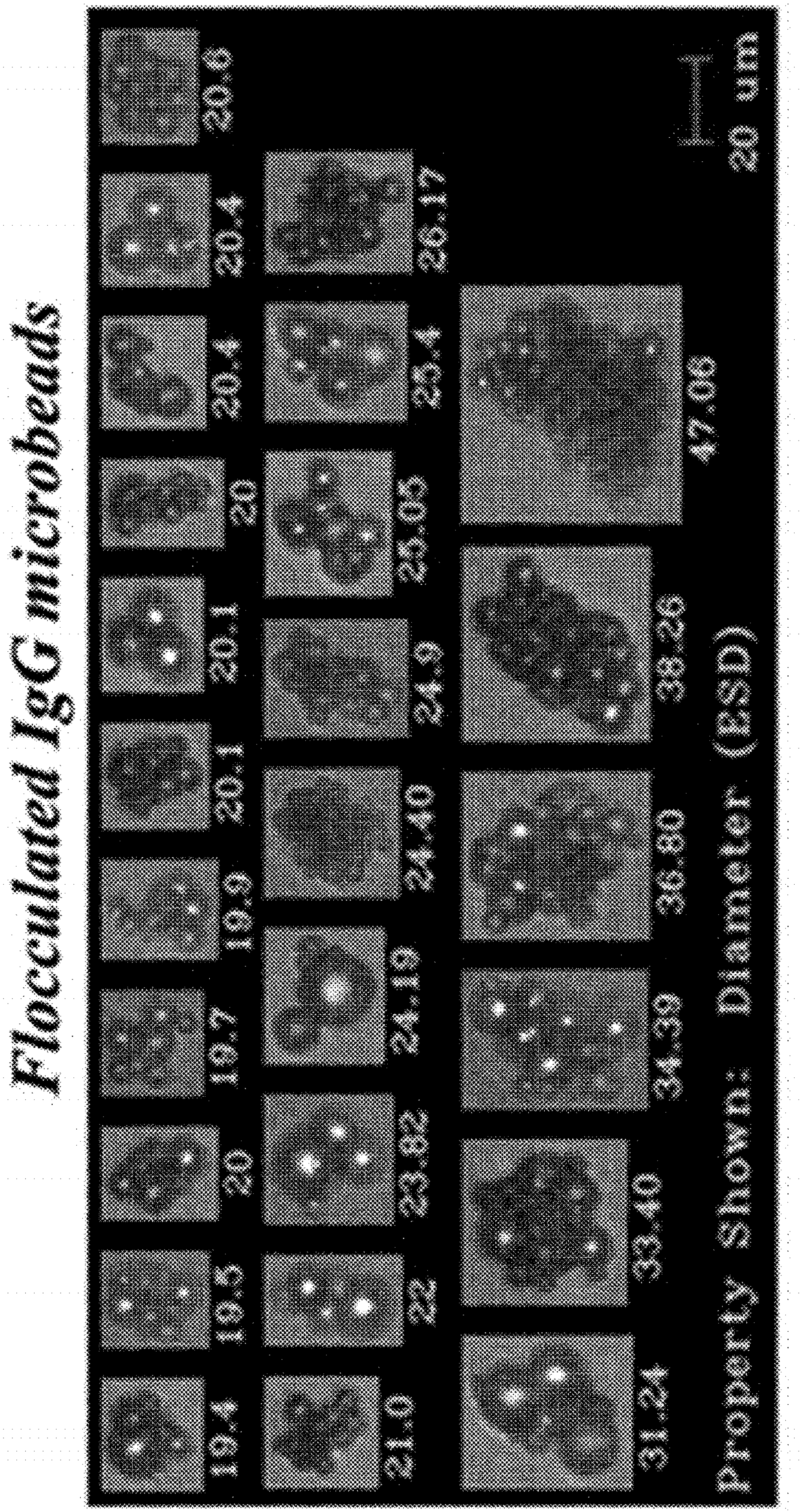
FIG. 3E is a drawing illustrating the results of identifying the FI image of aggregated IgG microbeads according to an embodiment of the present invention.

FIG. 3D and FIG. 3E confirm the outliers as aggregated microbeads. Not limited thereto, the size of a single IgG microbead, as shown in FIG. 3D, seemed to range from 1 to about 19 μm, and the aggregated microbeads, as shown in FIG. 3E, varied in size at 19 μm or more. Also, as shown in FIG. 3C, the smallest and least numerous aggregated microbeads were detected at 30 seconds, and the concentration of particles larger than 1 μm was the highest. This indicates a correlation between aggregation and extended dehydration times, and induced more aggregation during vortexing. Theoretically, as one 100 μm cube can contain one million 1 μm cubes, multiple aggregation can greatly reduce particle concentration.

Figure 3F:
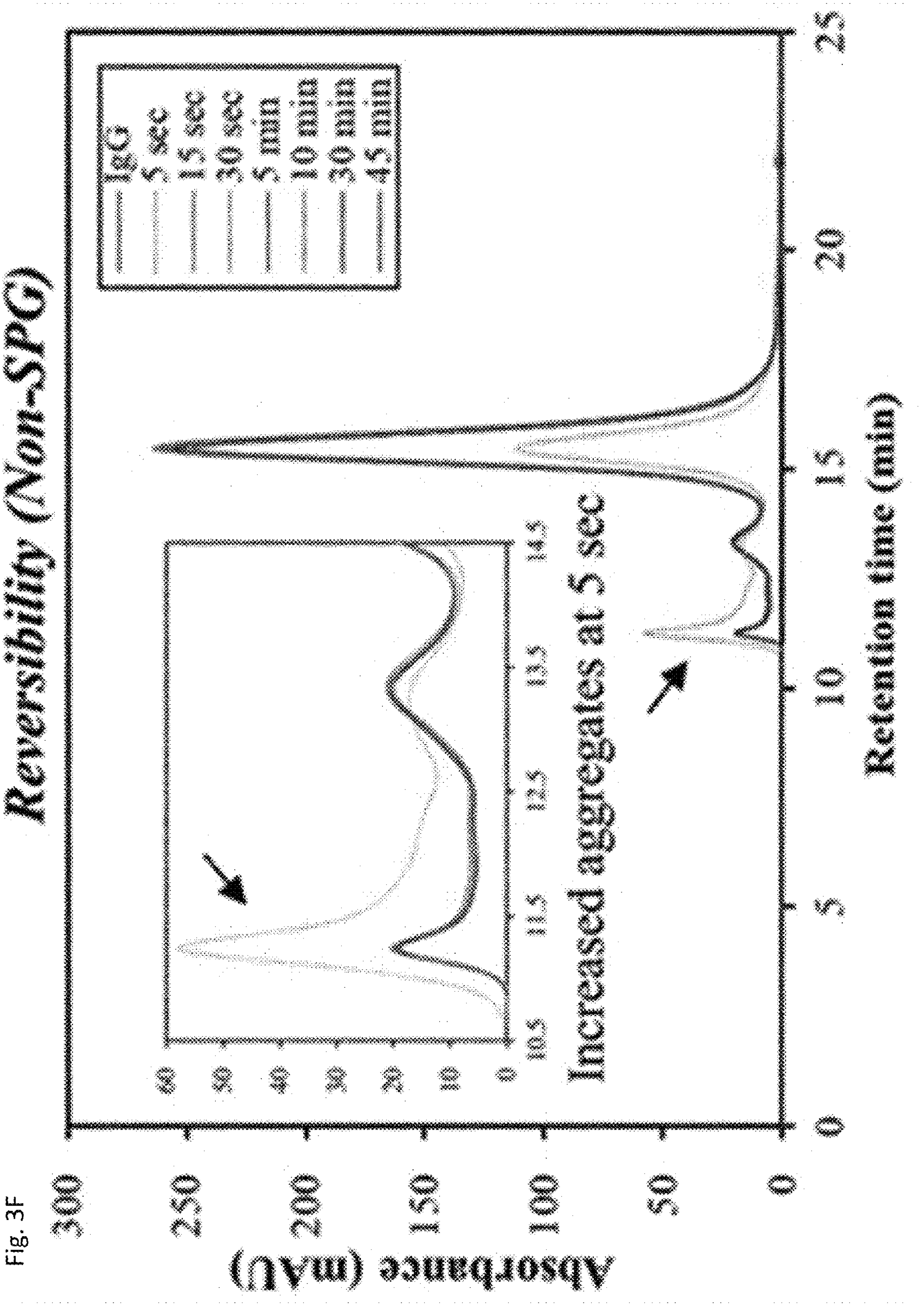
FIG. 3F is a drawing identifying the reversibility of IgG microbeads in the non-SPG method according to an embodiment of the present invention.

FIG. 3F represents the reversibility of IgG microbeads in non-SPG methods. The manufactured IgG microbeads were reversible when reconstituted according to dehydration time. For example, the majority of the reconstituted 5 mg/mL IgG microbeads using non-SPG methods reached reversibility of 93% or more. However, as shown in FIG. 3F, IgG microbeads manufactured with 5-second vortexing had only 45% reversibility. The results suggest that excessive moisture remaining during reconstitution or in the manufacturing process due to insufficient dehydration could induce protein aggregation, which may be associated with a decrease in quality. Nevertheless, such phenomena were not observed in IgG microbeads produced from the SPG membrane, but there was an increase in protein aggregation. While 30 seconds seemed to be an appropriate dehydration time based on particle concentration, 10 minutes was chosen for further studies to evaluate whether the effect of a pharmaceutical excipient and the temperature of n-octanol could reduce aggregation over extended times.

Experimental Example 4. Effects of Temperature and Excipients on the Formation of IgG Microbeads Upon encountering n-octanol, which forms spherical droplets, the protein in the solution is immediately reduced to a minimum surface area. This is due to higher surface tension of water than n-octanol having cohesive force on the surface of W/O droplet inducing the droplet to contract. Generally, the surface tension of water increases with decreasing temperature and addition of salt. In contrast, polysaccharides such as dextran and its monomer glucose are known to decrease the surface tension of water. Surfactants also reduce the surface tension of water and are often used as stabilizers in various emulsions due to micelle formation, suppressing the assembles of W/O or O/W droplets. No studies have been reported on antibody-related W/O emulsions using an SPG membrane, nor on the influence of temperature and pharmaceutical excipients on size distribution and reversibility. Therefore, additional experiments were conducted by pre-mixing the IgG solution independently with 300 mM NaCl, polysorbate 80 (PS80) at 10 times CMC (Critical Micelle Concentration), and 300 mM trehalose, to verify different effects. Furthermore, the premixed IgG solution was discharged into n-octanol at room temperature (RT) and refrigeration temperature (about 4° C.) for testing. In this case, the initial protein concentration of the pre-mixed IgG was reduced from 100 mg/mL to 50 mg/mL, and the same post-processing was followed after vortexing for 10 minutes.

Figure 4A:
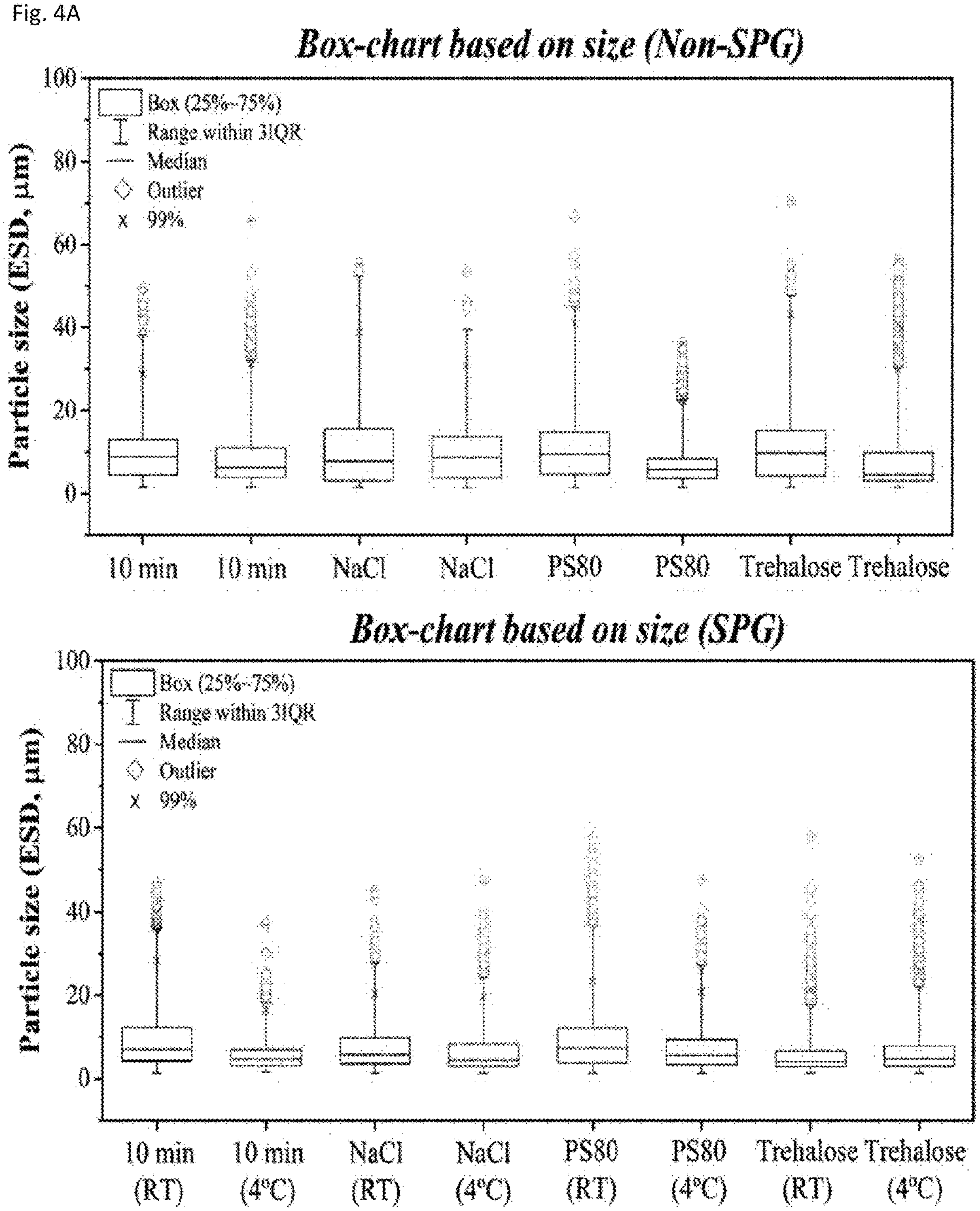
FIG. 4A is a drawing illustrating the box-chart based particle size distribution depending on the use of an excipient and temperature for IgG microbeads manufactured by non-SPG and SPG methods according to an embodiment of the present invention.
Figure 4B:
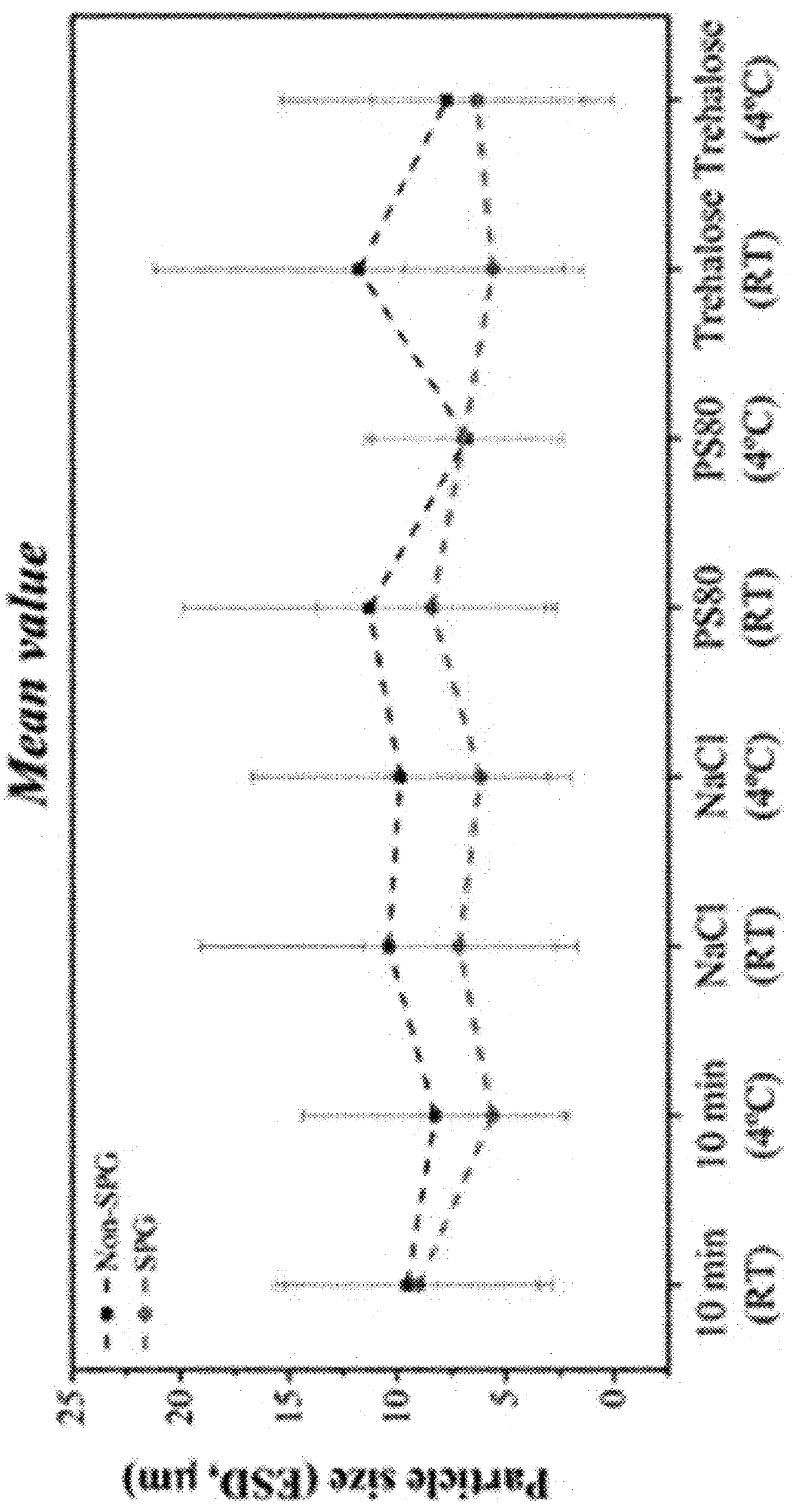
FIG. 4B is a drawing illustrating the average particle size depending on the use of an excipient and temperature for IgG microbeads manufactured by non-SPG and SPG methods according to an embodiment of the present invention.
Figure 4C:
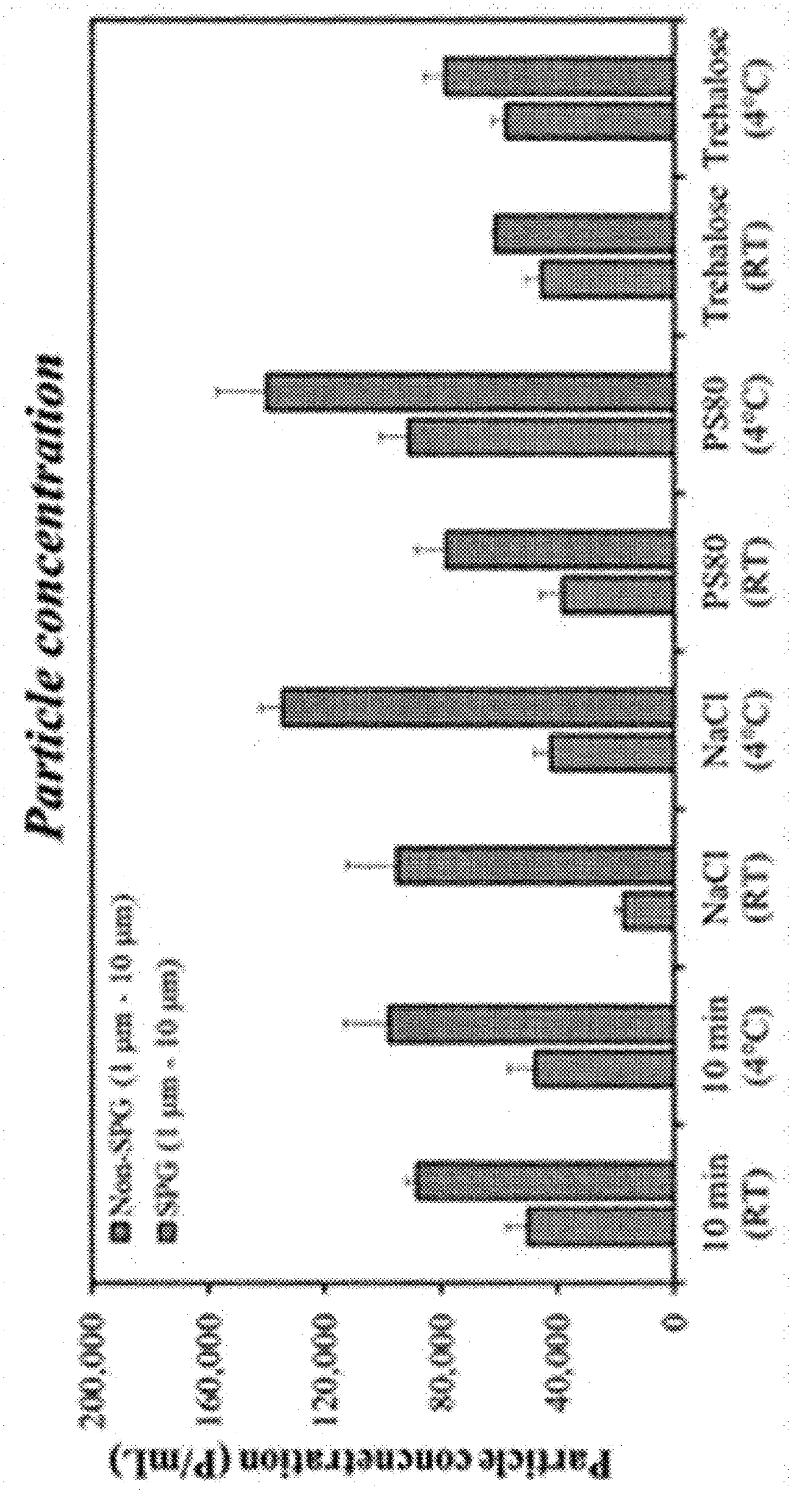
FIG. 4C is a drawing illustrating the particle concentration depending on the use of an excipient and temperature for IgG microbeads manufactured by non-SPG and SPG methods according to an embodiment of the present invention.

FIG. 4A represents the size distribution of IgG microbeads prepared in various conditions, with or without the SPG membrane, as shown in a box chart, FIG. 4B represents the mean value of IgG microbeads depending on the use of the SPG membrane, and FIG. 4C represents the particle concentration.

As shown in FIG. 4A, the size distribution of all manufactured IgG microbeads was narrowed at the lower temperature of n-octanol, and the size distribution was further narrowed when using the SPG membrane. Also, as shown in FIG. 4B, the mean value of the IgG microbeads (i.e., without excipients) decreased from 9.01±6.16 μm to 5.60±3.23 μm by simply lowering the temperature. These results suggest that as the temperature of n-octanol decreases, the surface tension of the droplets increases, thus reducing droplet fusion. The particle concentration, as shown in FIG. 4C, was almost doubled when the SPG membrane was applied.

As confirmed in FIG. 4A through 4C, the addition of NaCl, PS80, and trehalose to the IgG solution revealed different size distributions and aggregation tendencies during the formation of IgG microbeads. Although all details cannot be fully explained due to the complexity based on fluid dynamics affecting protein stability and size distribution of IgG microbeads, interestingly, PS80 and trehalose reduced the mean particle size of IgG microbeads produced in 4° C. n-octanol, even without using the SPG membrane (FIG. 4B). This phenomenon may be due to micelle formation and preferentially excluded water by PS80 and trehalose, respectively, rather than simply reducing the surface tension of water. Such results suggest that excipients are beneficial for microbead formation, even without using the SPG membrane. Nevertheless, the particle concentration of IgG microbeads was found to be highest, reaching approximately 150,000 P/mL, when discharged from 4° C. n-octanol through the SPG membrane after pre-mixing with PS80 (FIG. 4C).

PS80 is a nonionic surfactant, often used as a protein aggregation inhibitor by micelle formation, used as premicelles suppressing interfacial stress on the air-liquid or liquid-solid surface, and can also function as an emulsifier.

The present invention demonstrated usefulness in forming protein microbeads by inhibiting the fusion and aggregation of the droplets of the microbeads forming a large number of microbeads. Compared to this, trehalose, a non-reducing sugar, is often used as an osmotic and protein stabilizer, increasing the inherent folding stability that reduces stress-induced aggregation in bulk solution. However, sugars and polyols such as sucrose, trehalose, mannitol, and sorbitol have been reported to accelerate protein aggregation while stirring.

Figure 4D:
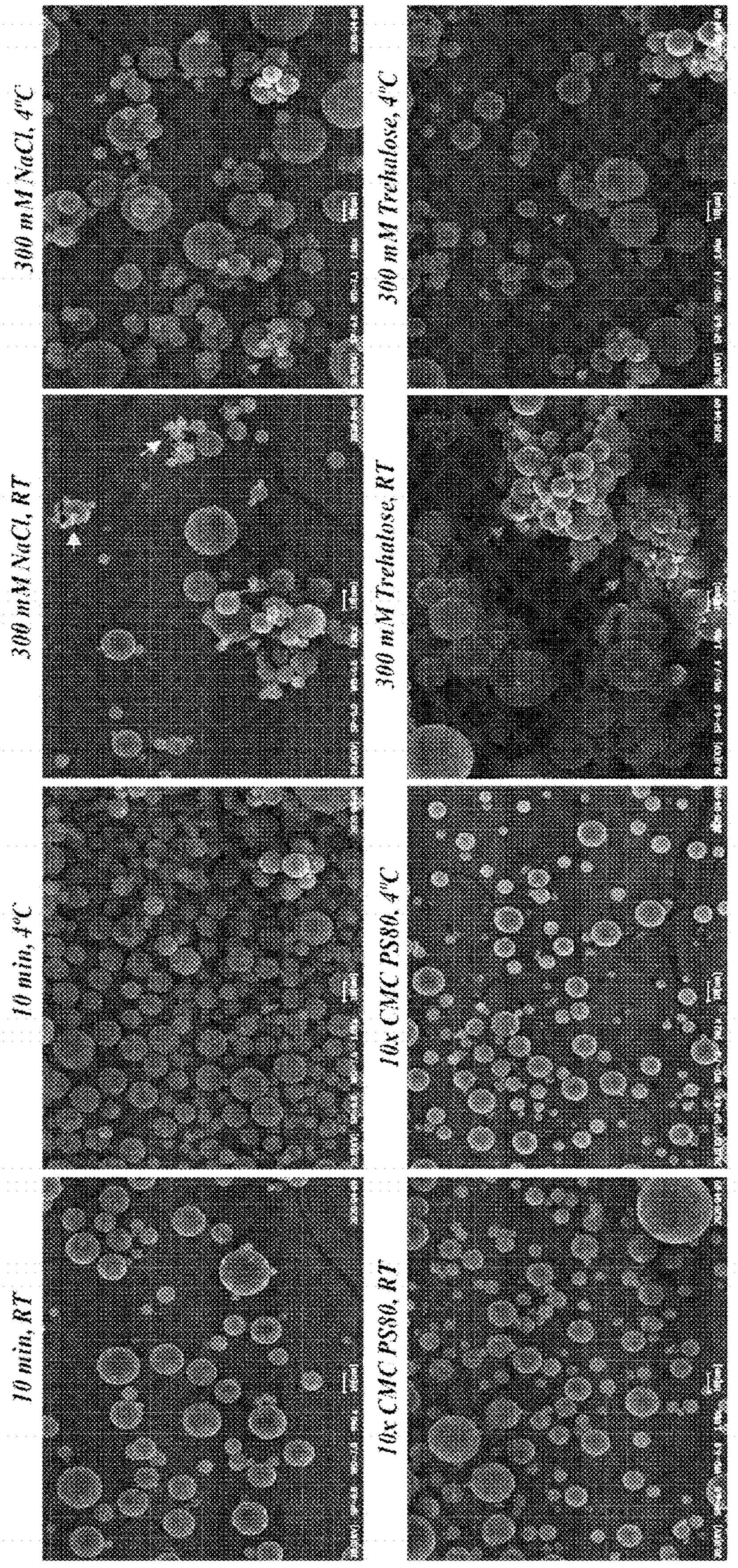
FIG. 4D is a drawing identifying the SEM image results depending on the use of an excipient and temperature for IgG microbeads manufactured by the SPG method according to an embodiment of the present invention.

FIG. 4D shows an SEM image of IgG microbeads using FI, where the red arrows indicate aggregation when treated with NaCl and trehalose respectively at room temperature (RT) and 4° C., and the yellow arrow indicates NaCl-like crystals when treated with NaCl at RT.

Referring to the Experimental Example 5 below, the reversibility of the IgG microbeads using trehalose after reconstruction did not indicate significant monomer loss or increase in aggregation, and was relatively higher than the IgG microbeads using PS80.

Consequently, as shown in FIG. 4D, the phenomenon of lower particle concentration due to trehalose than PS80 may be due to the increase in viscosity/adhesiveness of the microbead surface, not aggregation due to protein instability.

On the other hand, the aggregation of the glass IgG microbeads shown to be adsorbed on each other's surface (i.e., no excipients) showed a dependence on the initial IgG concentration loaded on the SPG membrane. When the initial IgG concentration decreased from 100 mg/mL (FIG. 3A) to 50 mg/mL (FIG. 4A), the number and size of outliers in the IgG microbeads gradually decreased by almost 2 times. That is, surface adsorption is related to the hydrophobic interactions between IgG microbeads due to an increase in IgG density. Hydrophobic interactions of proteins are known to be the dominant force inducing self-binding of proteins. Such interpretation can also support the reason why NaCl reduced the particle concentration in non-SPG methods. Previously, the ionic strength of the protein solution increased, increasing the protein aggregation rate of the monoclonal antibody and other proteins. This is because the electrical repulsion of the protein molecules decreased and protein-protein interactions increased. The results suggested that an increase in ionic strength can induce more aggregation of microbeads or fusion of W/O droplets during vortexing due to increased protein-protein interactions.

Nevertheless, the particle concentration of the IgG microbeads gradually increased to nearly the same number as PS80 by adding NaCl to the SPG membrane. This phenomenon can be explained by the false-positive reading caused by the presence of NaCl-like crystals observed in the SEM image at RT (i.e., the yellow arrow 1085 in FIG. 4D). Salts dissolved in water during the dehydration process are extracted along with the water and crystallized due to low solubility in n-octanol. The current FI image was not set to distinguish foreign substances from the IgG microbeads because the size of the material is relatively small (<2 pin). Therefore, further studies were conducted using only PS80 and trehalose.

Experimental Example 5. Reversibility of IgG Microbeads by PS80 and Trehalose The purpose of the present invention is to develop a new formulation that can be applied to highly concentrated proteins, which are very beneficial compared to the freeze-drying process and can be sufficiently biophysically stable as freeze-drying products. So far, the results suggest that protein microbeadization could be a potential alternative as it dehydrates the protein within one minute, and the product itself is spherical and has excellent fluidity for the process after filling due to its fine powder form. However, protein products may still have issues with rehydration at high protein concentrations.

Thus, its reversibility was evaluated at two different concentrations of IgG microbeads, 5 mg/mL and 100 mg/mL. The microbeads were prepared using the latest process conditions; initial IgG concentration of 50 mg/mL, 4° C. n-octanol, hydrophobic SPG membrane, vortexing for 10 minutes, rinsing three times with ethanol, and then vacuum drying at a vacuum pressure of 57 mTorr for 48 hours at 25° C.

Figure 5A:
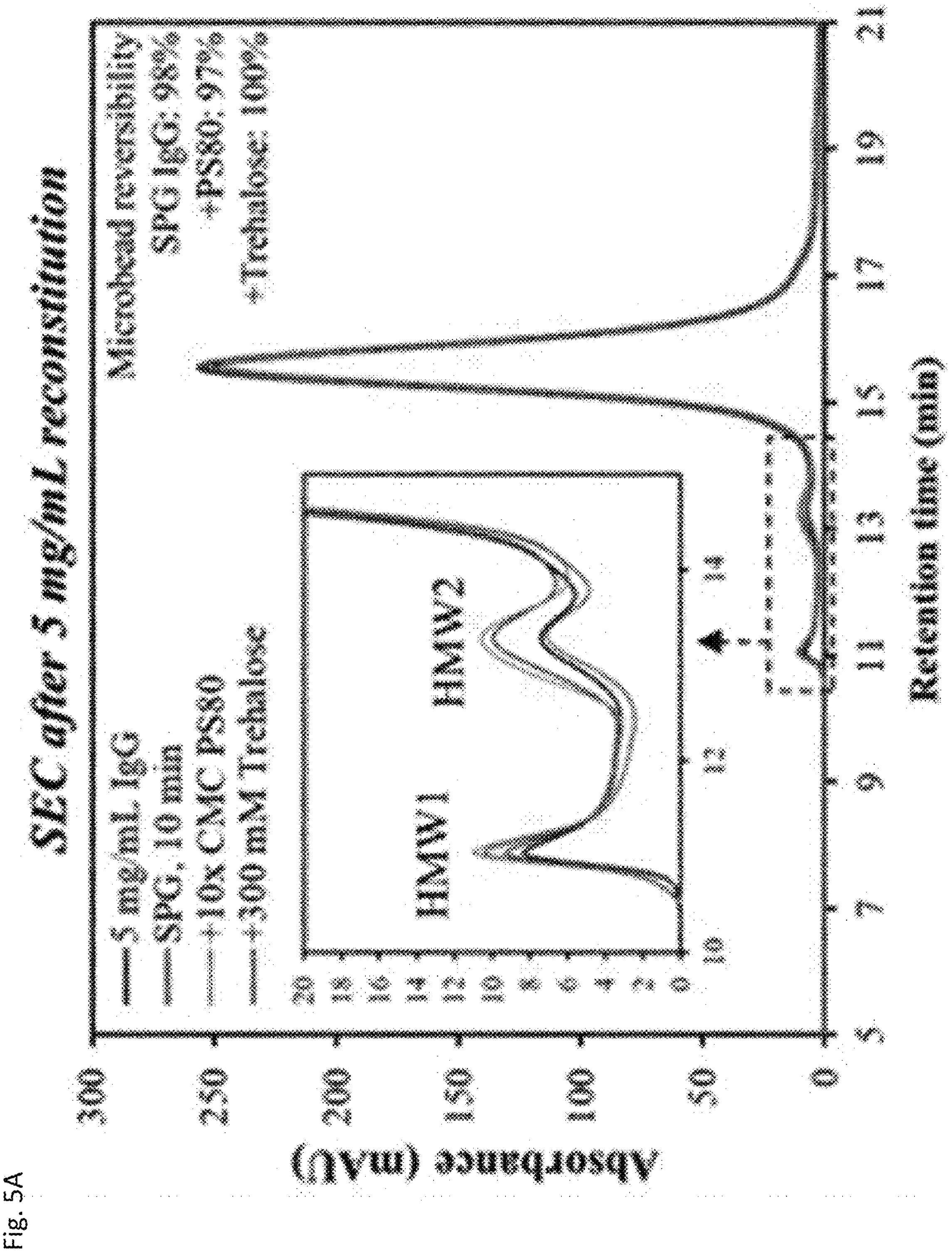
FIG. 5A is a drawing identifying the reversibility of 5 mg/mL IgG microbeads manufactured using PS80 and trehalose according to an embodiment of the present invention.

As a result, as shown in FIG. 5A, the monomer reversibility of 5 mg/mL IgG microbeads was 98% compared to before the manufacturing process, and it further decreased to 97% when PS80 was added. Although the loss may seem insignificant, it indicates that the formation of soluble aggregates during manufacturing is related to monomer loss, as all microbeads, whether or not PS80 is used, showed an increase in high molecular weight species (i.e., HMW1 and HMW2). Because the IgG microbeads from the non-SPG method did not show an increase in HMWs, it could have been induced to aggregate when passing through the SPG membrane (FIG. 3E).

Figure 5B:
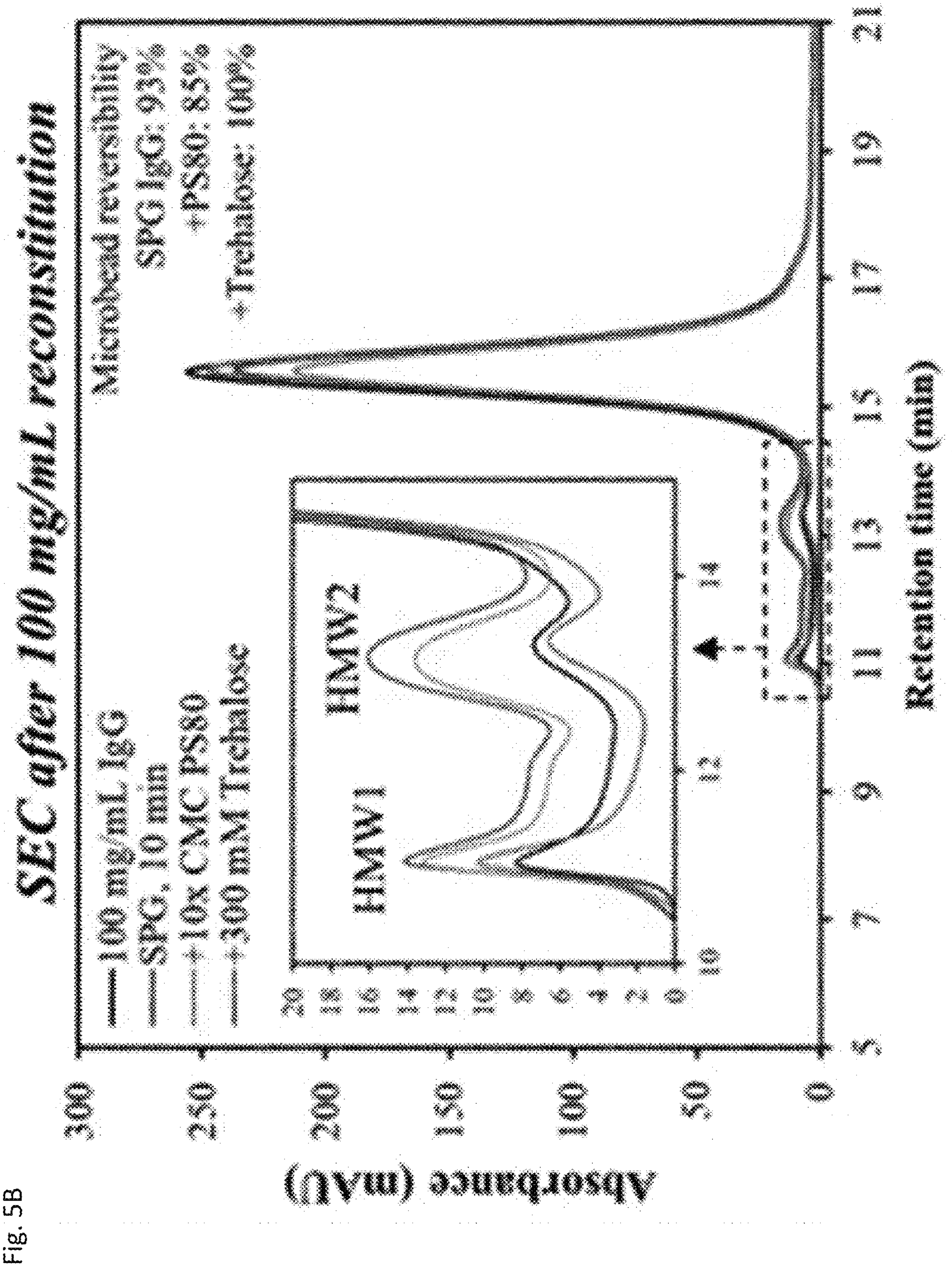
FIG. 5B is a drawing identifying the reversibility of 100 mg/mL IgG microbeads manufactured using PS80 and trehalose according to an embodiment of the present invention.

Also, as shown in FIG. 5B, the monomer reversibility of 100 mg/mL IgG microbeads using PS80 was 85%, showing the highest monomer loss. Surfactants are generally used in diluents to minimize protein aggregation caused by reconstitution. However, pre-mixed PS80 was not beneficial for reversibility when reconstituted at higher protein concentrations in the present invention. This could be due to the low levels of residual peroxides in PS80, which can potentially impact protein stability, especially in dry states.

Figure 5C:
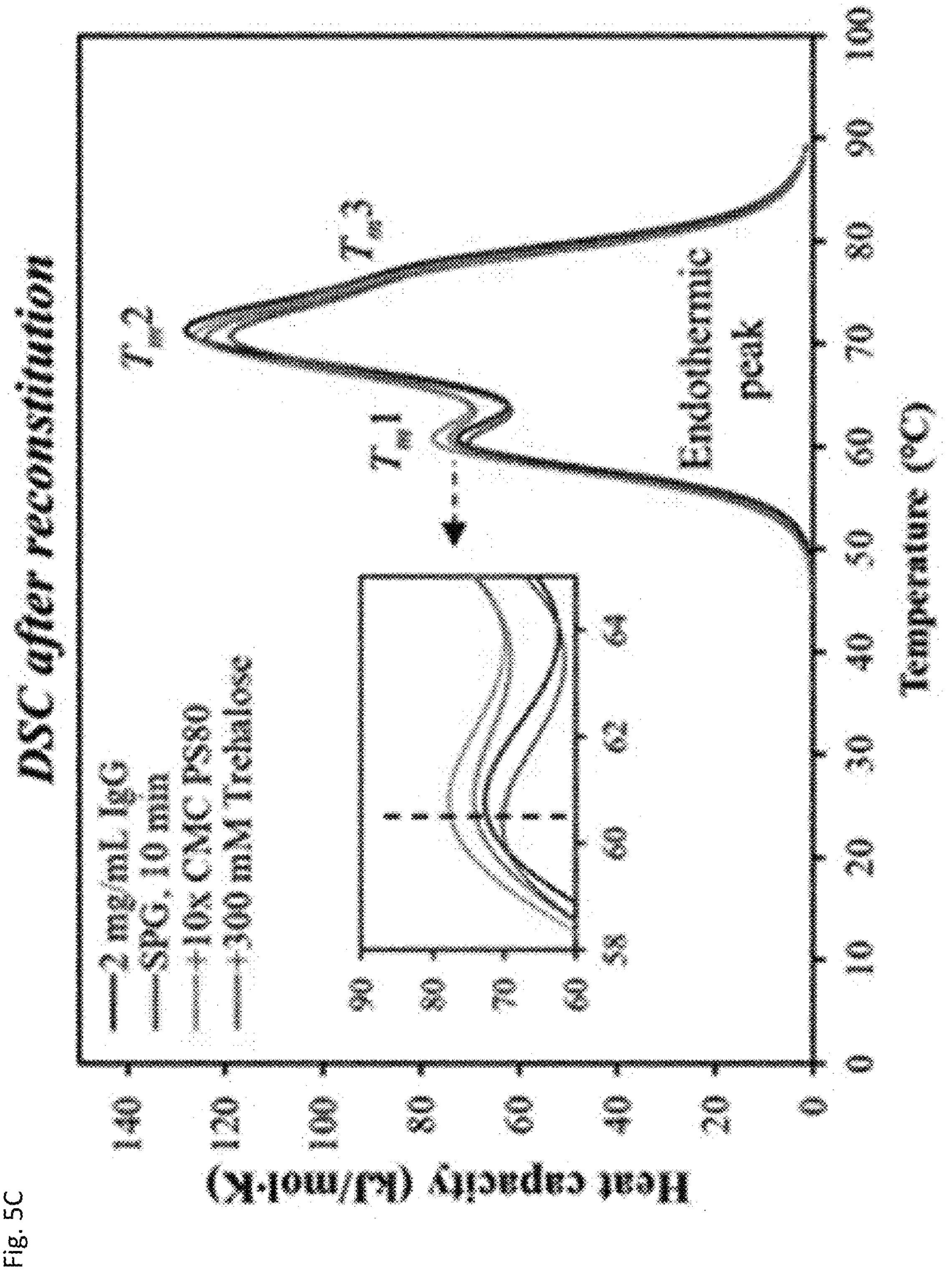
FIG. 5C is a drawing illustrating the DSC temperature recording of IgG microbeads manufactured using PS80 and trehalose according to an embodiment of the present invention.

However, as shown in FIG. 5C, PS80 was not a denaturant of IgG since DSC did not show any significant difference in $T_m$1 (i.e. $\Delta T_m 1 < 1°$ C.) before and after microbead formation. Also, there was a slight shift to lower temperatures for reconstituted IgG microbeads without excipients. The combined results of DSC and SEC were speculated that IgG could have experienced partial protein unfolding during the contact with hydrophobically modified SPG membrane. Additional investigations were carried out to assess the impact of drying conditions.

In contrast, IgG microbeads using trehalose showed about 100% reversibility at both concentrations, with no increase in HMWs (FIGS. 5A and 5B). As mentioned above, the aggregation of IgG microbeads containing trehalose can be concluded as a sticky environment, not an instability factor. Trehalose effectively suppressed the aggregation of IgG during preparation and reconstitution, which can be explained by the mechanism of trehalose forming effective hydrogen bonds with protein when there is no water due to dehydration stress. As a result, trehalose was confirmed to be a better excipient than PS80 in relation to protein stability in microbeadization.

Experimental Example 6. Effect of Drying Conditions and Initial Concentration on IgG Microbead Formation Table 1 below shows the amounts of ethanol and n-octanol present in 50 mg IgG microbeads.

TABLE 1

| Time | 25° C. 57 mTorr | | 35° C. 57 mTorr | | 35° C. 200 mTorr | |
|---|---|---|---|---|---|---|
| (hours) | Ethanol | Octanol | Ethanol | Octanol | Ethanol | Octanol |
| 24 | 22.1 | 507.6 | n/d | n/d | n/d | n/d |
| 48 | 26.3 | 314.8 | LOQ | 44.8 | 24.3 | 17.5 |
| 72 | 31.5 | 239.5 | n/d | n/d | n/d | n/d |
| 120 | 3.6 | 133.5 | LOQ | 39.7 | 2.2 | 16.2 |

n/d: Not determined

All samples were prepared under the latest process conditions, which include an initial IgG concentration of 50 mg/mL, n-octanol at 4° C., a hydrophobic SPG membrane, vortexing for 10 minutes, and rinsing three times with ethanol. The drying time, temperature, and vacuum pressure were prepared under different conditions. When dried for 48 hours at 25° C., approximately 314.8 ppm of n-octanol was retained. This could potentially cause shifts in the $T_m$1 of the IgG after reconstitution, a sudden reversible decrease of PS80, and the adhesive environment caused by trehalose (FIG. 5C).

Furthermore, after 120 hours of drying at 25° C., the ethanol and n-octanol decreased to 3.6 ppm and 133.5 ppm respectively. The reduction in n-octanol persisted when the temperature was increased to 35° C., resulting in 44.8 ppm and 39.7 ppm respectively after 48 hours and 120 hours. Higher temperatures were not considered further due to potential impacts on protein stability. Instead, the vacuum pressure was adjusted to 200 mTorr at 35° C. This value was selected based on several temperature-dependent vapor pressure measurements of n-octanol reported in the literature (K. Nasirzadeh, R. Neueder, W. Kunz, Journal of Chemical & Engineering Data, 51 (2006) 7-10). This was effective as the n-octanol was reduced to 17.5 ppm and 16.2 ppm respectively after 48 hours and 120 hours. Since the difference between the two time points was minimal, a drying period of 48 hours at 200 mTorr at 35° C. was selected for further studies.

Figure 6A:
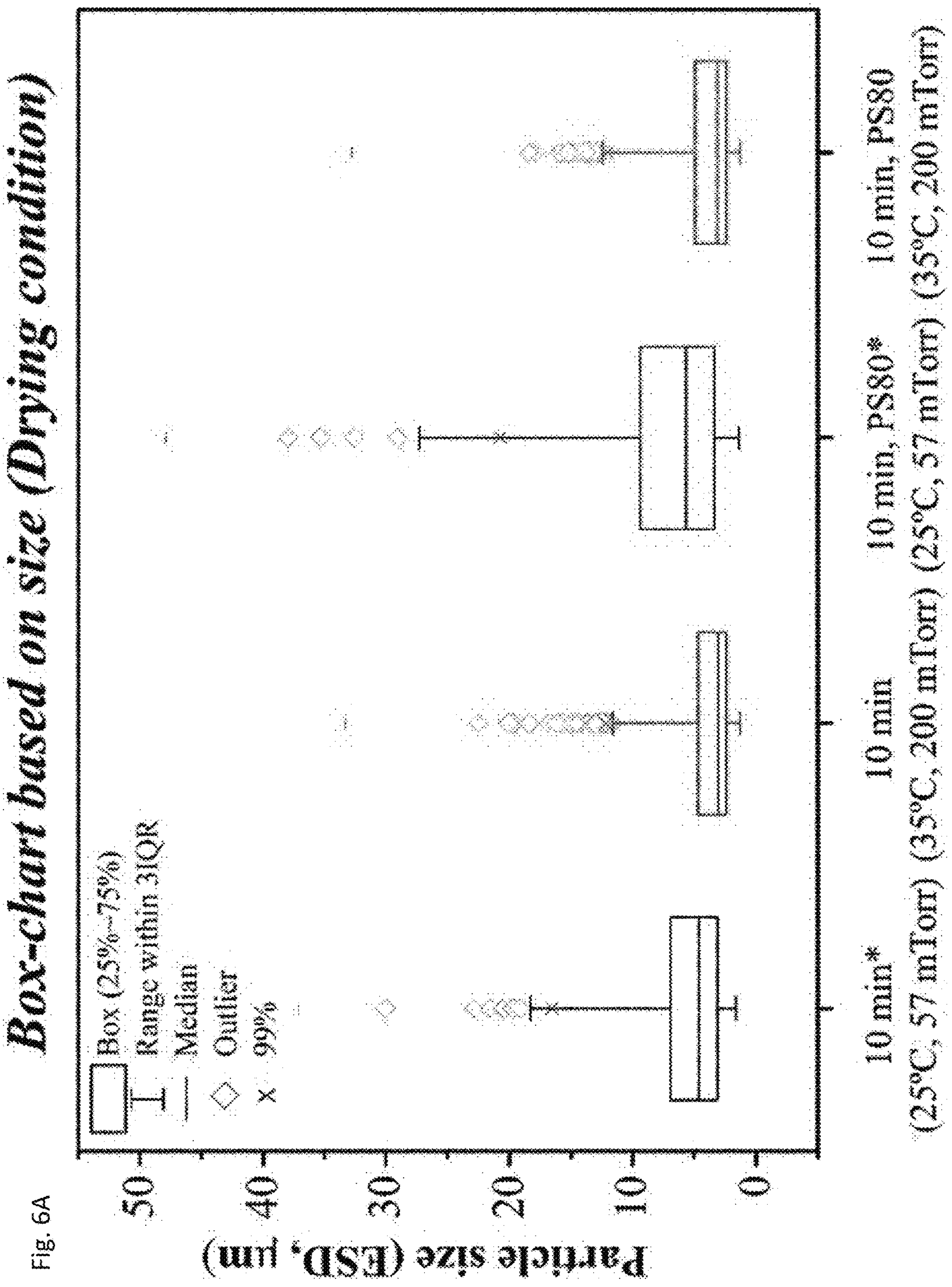
FIG. 6A is a drawing illustrating the box-chart based particle size depending on the drying conditions of IgG microbeads manufactured using PS80 according to an embodiment of the present invention.
Figure 6B:
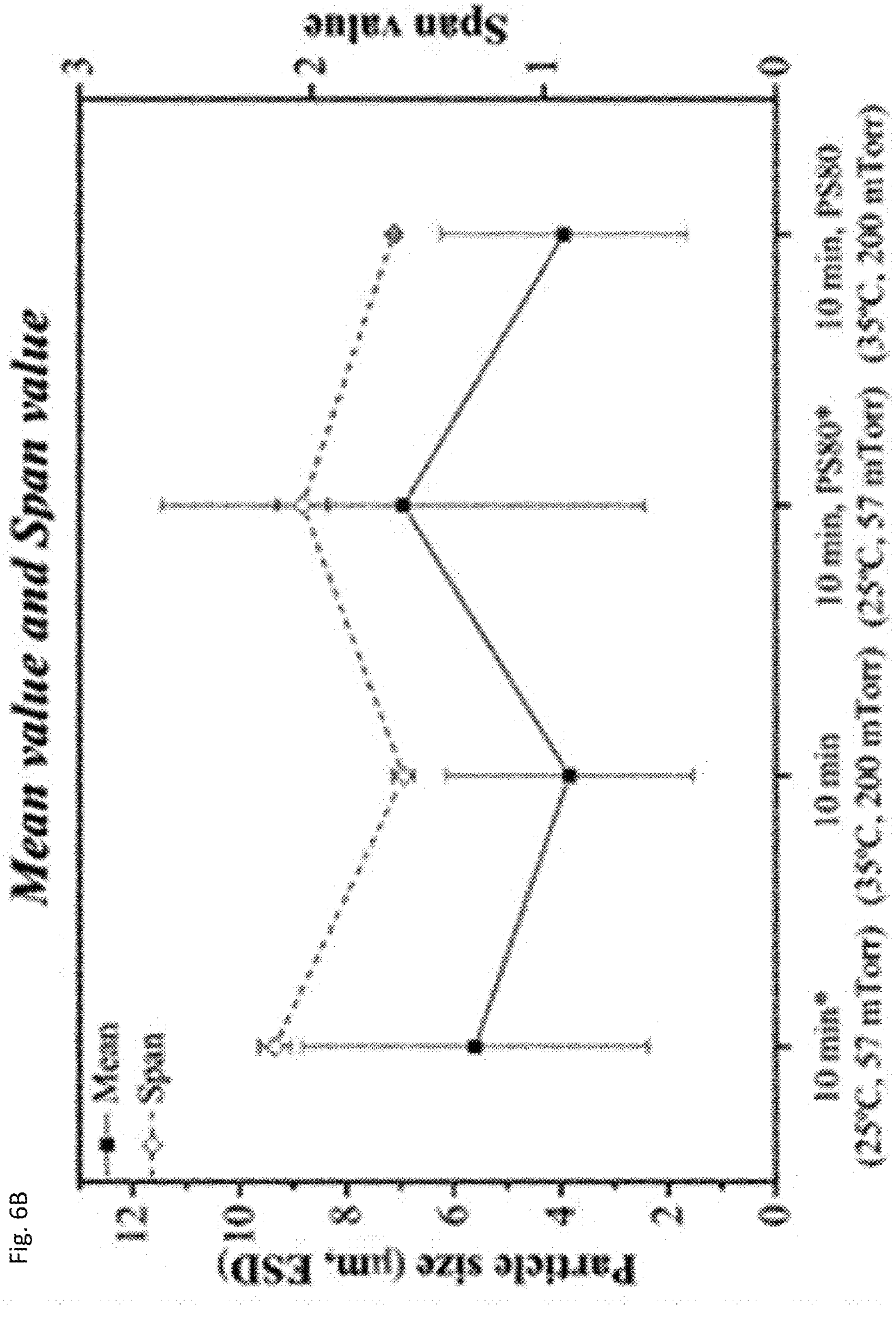
FIG. 6B is a drawing illustrating the average particle size and span values depending on the drying conditions of IgG microbeads manufactured using PS80 according to an embodiment of the present invention.
Figure 6C:
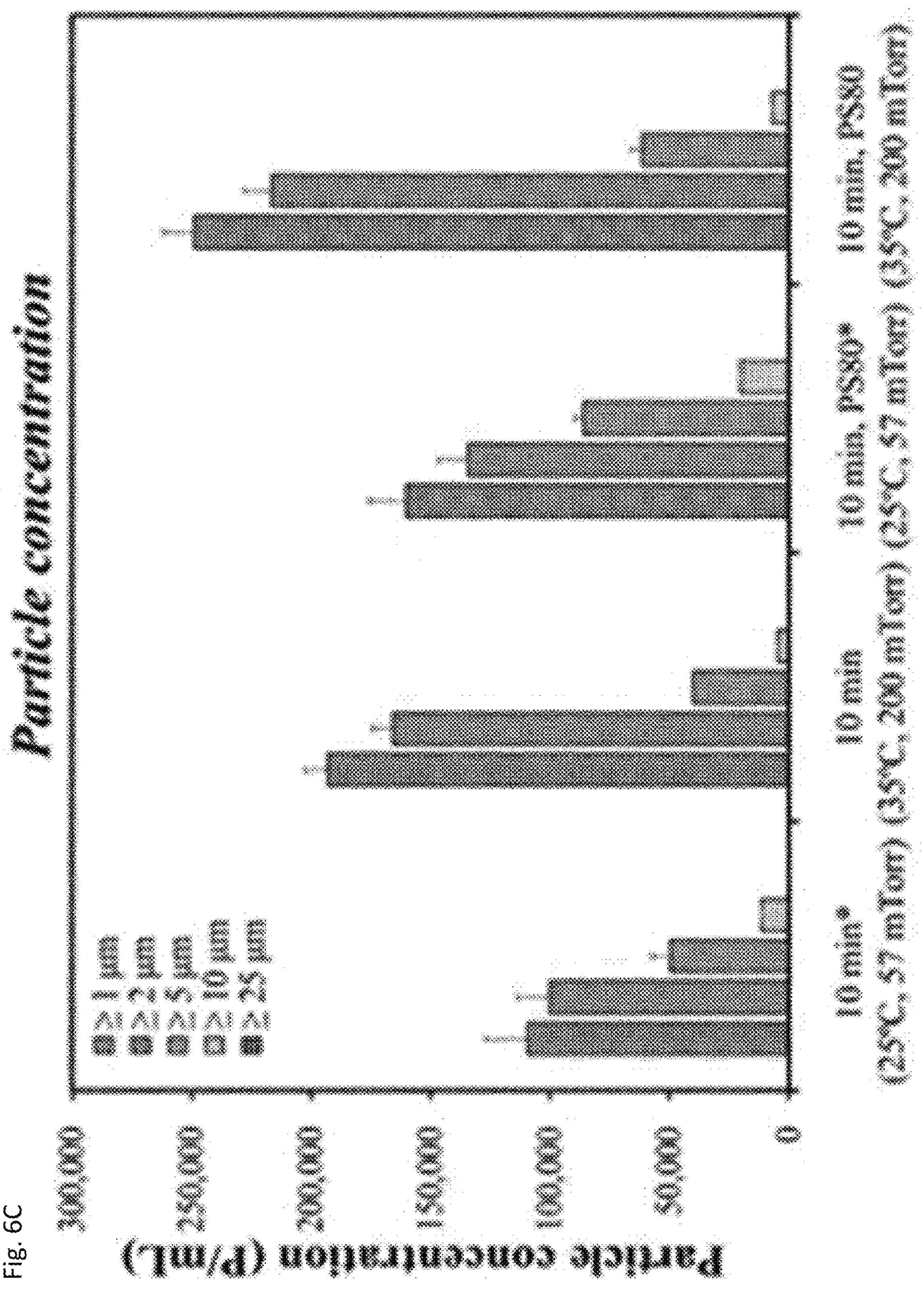
FIG. 6C is a drawing illustrating the particle concentration depending on the drying conditions of IgG microbeads manufactured using PS80 according to an embodiment of the present invention.

FIG. 6A shows a comparison of the size distribution of IgG microbeads before and after the adjusted vacuum drying process. As a result, the IgG microbeads, with or without the use of PS80, showed a relatively narrow size distribution when dried at higher vacuum pressure and temperature. Additionally, as shown in FIG. 6B, the average and span values were also reduced, suggesting that the residual solvent affected the size distribution of the microbeads. Moreover, as shown in FIG. 6C, not only did the particle concentration of the IgG microbeads increase with the adjusted vacuum drying process, but larger particle formation (i.e., >5 μm) was reduced, suggesting lesser aggregation of the microbeads.

Hence, reducing the residual solvent could become yet another key factor in producing stable protein microbeads.

After determining the influence of the residual solvent on the size distribution of the microbeads, an investigation was carried out on one final process modification using the average initial protein concentration of the SPG membrane. Previously, more outliers of greater number and size were detected in the 100 mg/mL IgG microbeads compared to the 50 mg/mL IgG microbeads, indicating the dependence of aggregation on the initial protein concentration. For a better understanding, a comparison was made between the initial IgG concentrations of 10 mg/mL and 50 mg/mL using the adjusted process conditions; n-octanol at 4° C., hydrophobic SPG membrane, vortexing for 30 seconds, rinsing three times with ethanol, and then vacuum drying at 200 mTorr vacuum pressure for 48 hours at 35° C. Here, the dehydration time was changed from 10 minutes to 30 seconds, and it was performed under the optimal time condition confirmed in the Experimental Example 3.

Figure 6D:
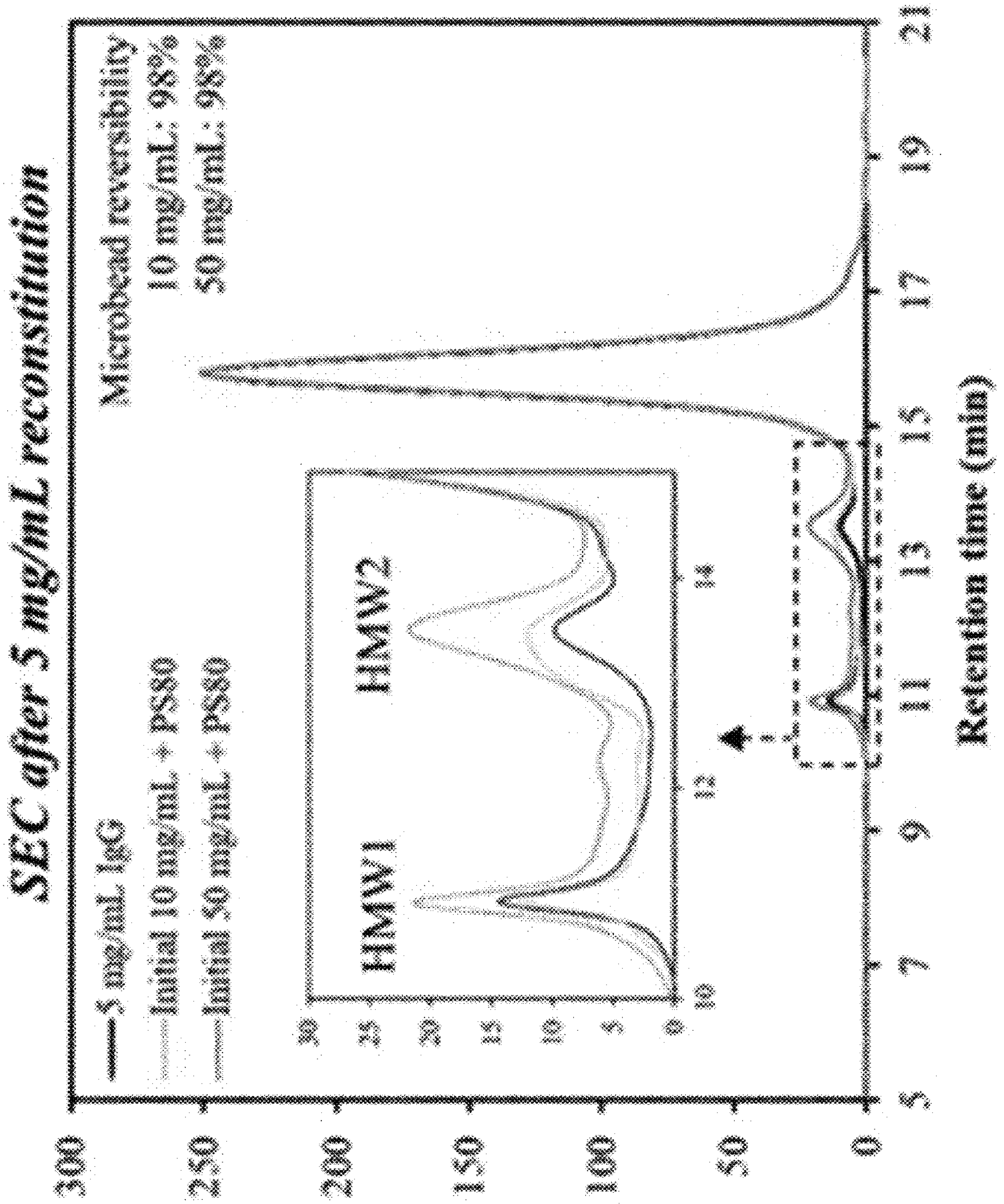
FIG. 6D is a drawing illustrating the monomer reversibility of 5 mg/mL IgG microbeads manufactured using PS80 at two different initial IgG concentrations according to an embodiment of the present invention.
Figure 6E:
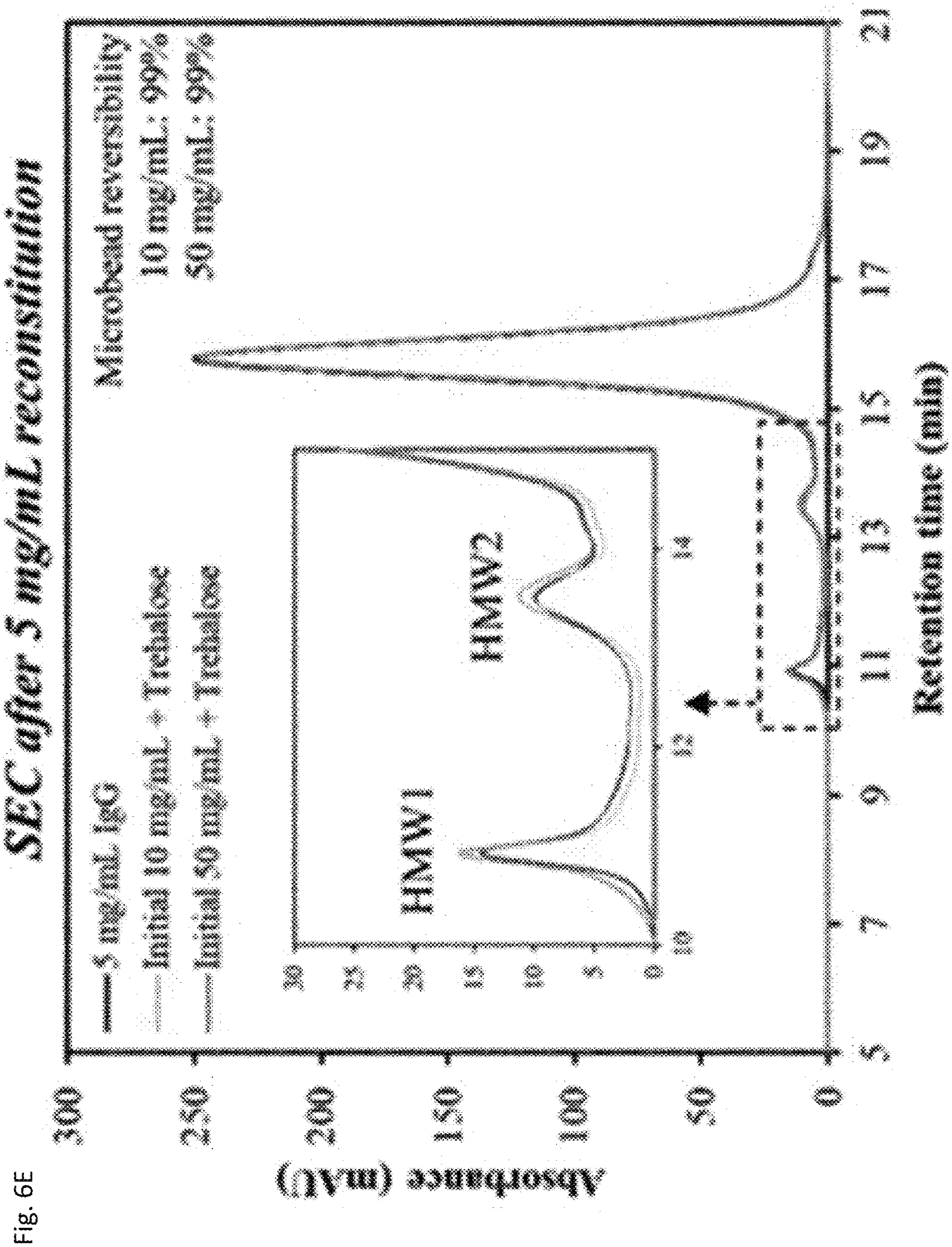
FIG. 6E is a drawing illustrating the monomer reversibility of 5 mg/mL IgG microbeads manufactured using trehalose at two different initial IgG concentrations according to an embodiment of the present invention.
Figure 6F:
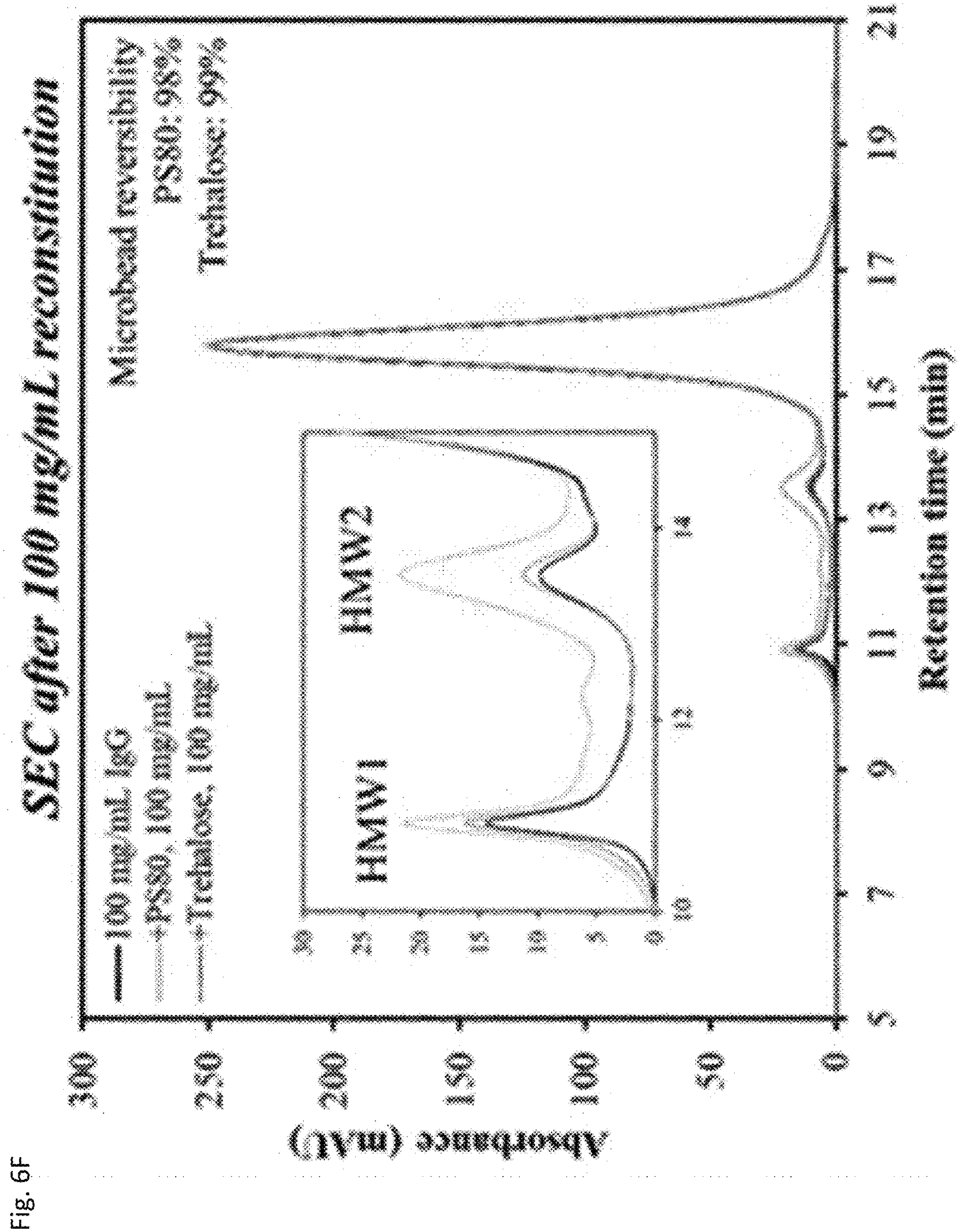
FIG. 6F is a drawing illustrating the monomer reversibility of 100 mg/mL IgG microbeads manufactured using PS80 and trehalose from an initial IgG concentration of 50 mg/mL according to an embodiment of the present invention.

FIGS. 6D and 6E illustrate the monomer reversibility of 5 mg/mL IgG microbeads prepared using PS80 and trehalose from two different initial IgG concentrations. As shown in FIG. 6D, the reversibility of the microbeads prepared using PS80 reached 98% equally at both concentrations. Interestingly, HMW2 relatively decreased when the initial IgG concentration was reduced to 10 mg/mL, verifying that less protein was affected during the microbeadization process at lower concentrations. Reversibility was relatively higher at about 98% than the results confirmed in the Experimental Example 5 and the results of FIG. 6F which illustrates the monomer reversibility of 100 mg/mL IgG microbeads prepared using PS80 and trehalose from an initial IgG concentration of 50 mg/mL. These results could interpret the initial results due to the residual solvent (mainly n-octanol) as the reversibility of 100 mg/mL IgG microbeads containing PS80 did not change with the minimized content of n-octanol.

Figure 6G:
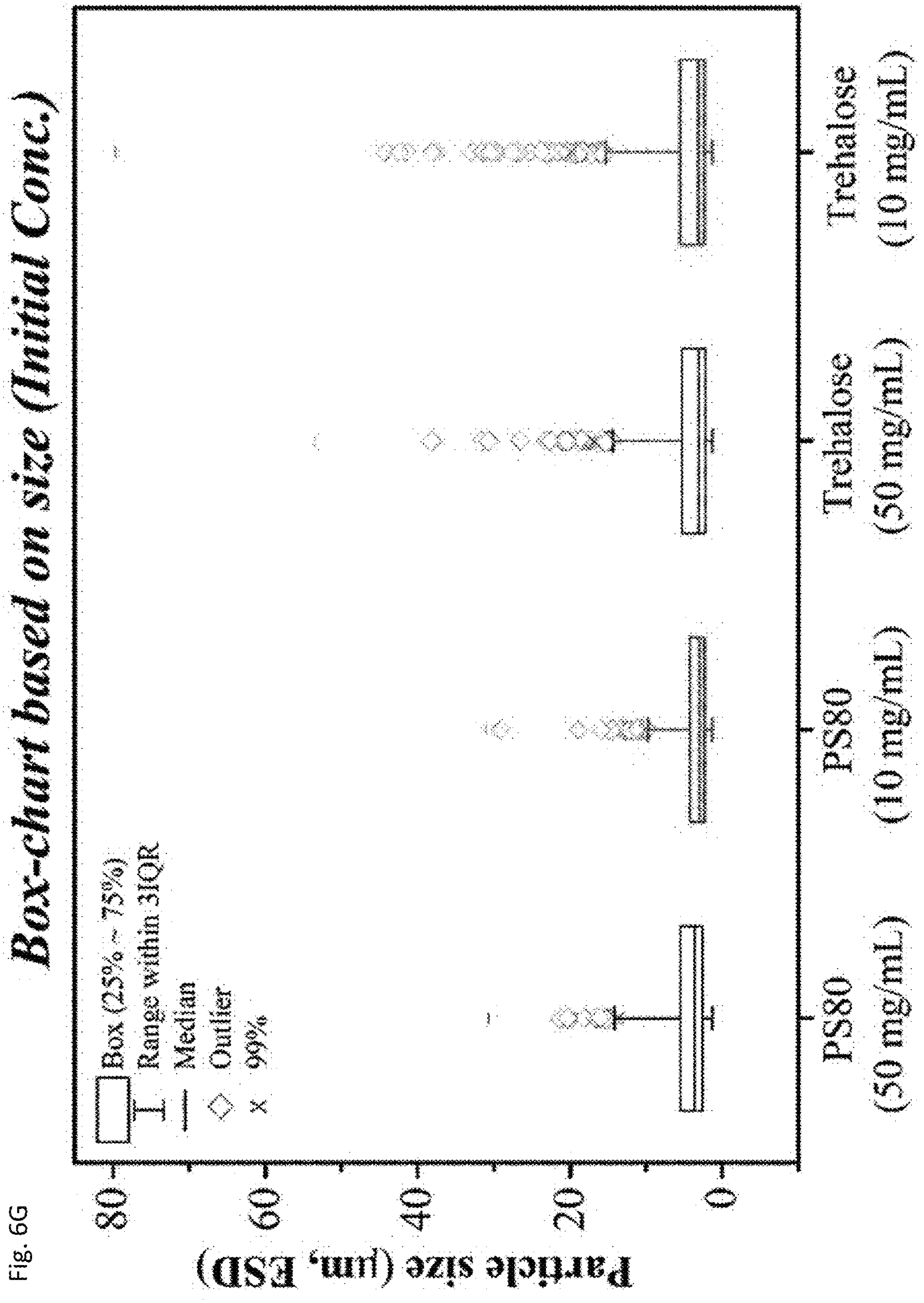
FIG. 6G is a drawing illustrating the box-chart based particle size depending on the initial IgG concentration of IgG microbeads manufactured using PS80 and trehalose according to an embodiment of the present invention.
Figure 6H:
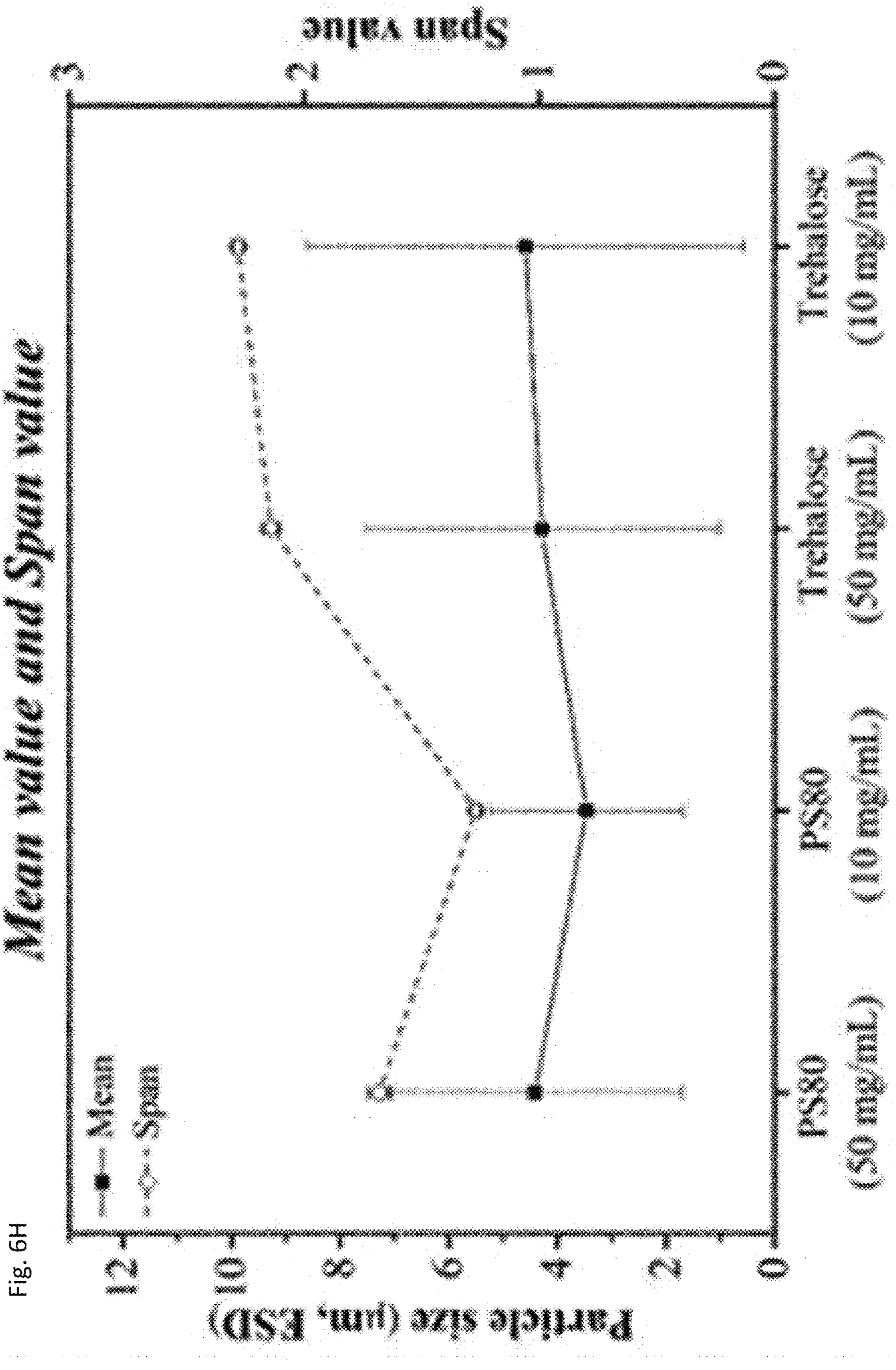
FIG. 6H is a drawing illustrating the average particle size and span values depending on the initial IgG concentration of IgG microbeads manufactured using PS80 and trehalose according to an embodiment of the present invention.

Also, as shown in FIGS. 6G and 6H, a faster dehydration time reduced the size distribution to a minimum average value of 3.47 μm and a minimum span value of 1.27 at a lower initial protein concentration. The results illustrated the effects of process variations that affect the size distribution and reversibility of the protein microbeads.

Figure 6I:
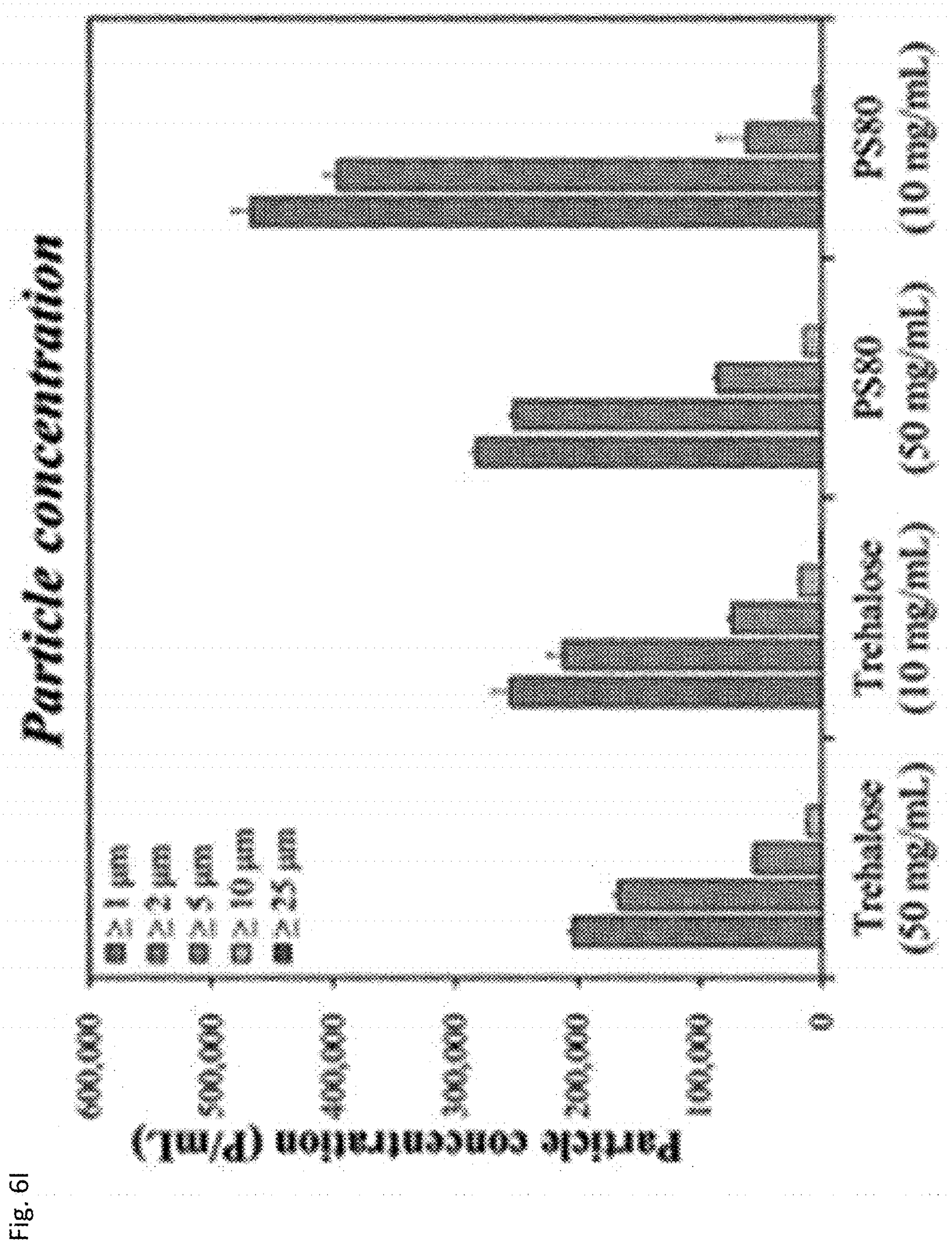
FIG. 6I is a drawing illustrating the particle concentration depending on the initial IgG concentration of IgG microbeads manufactured using PS80 and trehalose according to an embodiment of the present invention.

IgG microbeads containing trehalose demonstrated the highest reversibility after reconstitution without signs of increased protein aggregation at both protein concentrations. However, there was a slight recovery reduction from 100% to 99%, predicted to be due to a loss from increasing drying temperatures. On the other hand, larger outliers were observed at lower initial protein concentrations. Yet, no further investigations were conducted as the aggregation caused by trehalose was determined to be a low risk. Also, the particle concentration of IgG microbeads containing trehalose was not greatly changed by adjusted drying processes or initial protein concentrations as shown in FIG. 6I, suggesting that adhesion occurred due to aqueous moisture, not the residual solvent.

Experimental Example 7. Drop Test and Thermal Exposure for IgG Microbeads

Figure 7A:
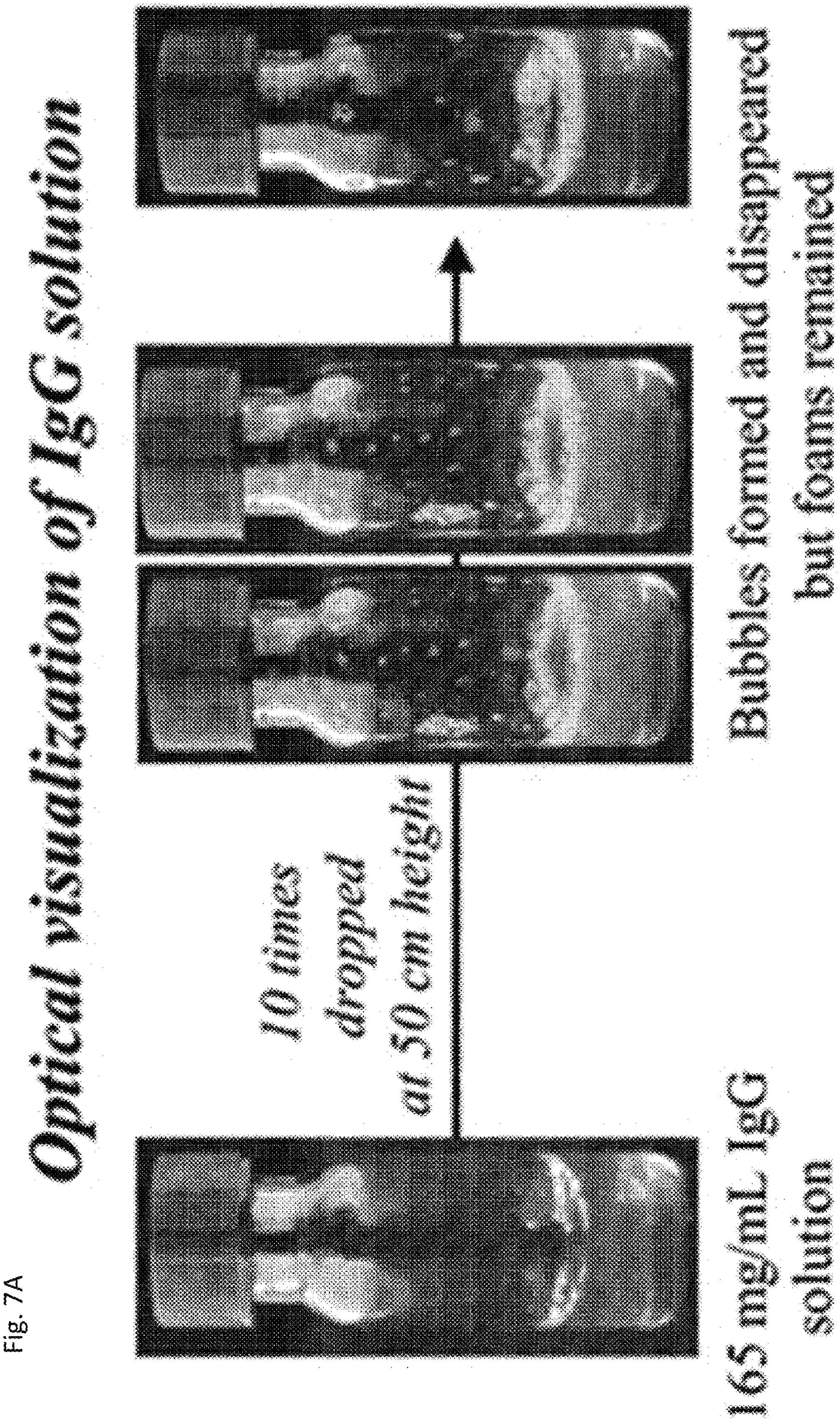
FIG. 7A is a drawing identifying the change when a vial containing a 165 mg/mL IgG solution is dropped from a height of 50 cm according to an embodiment of the present invention.
Figure 7B:
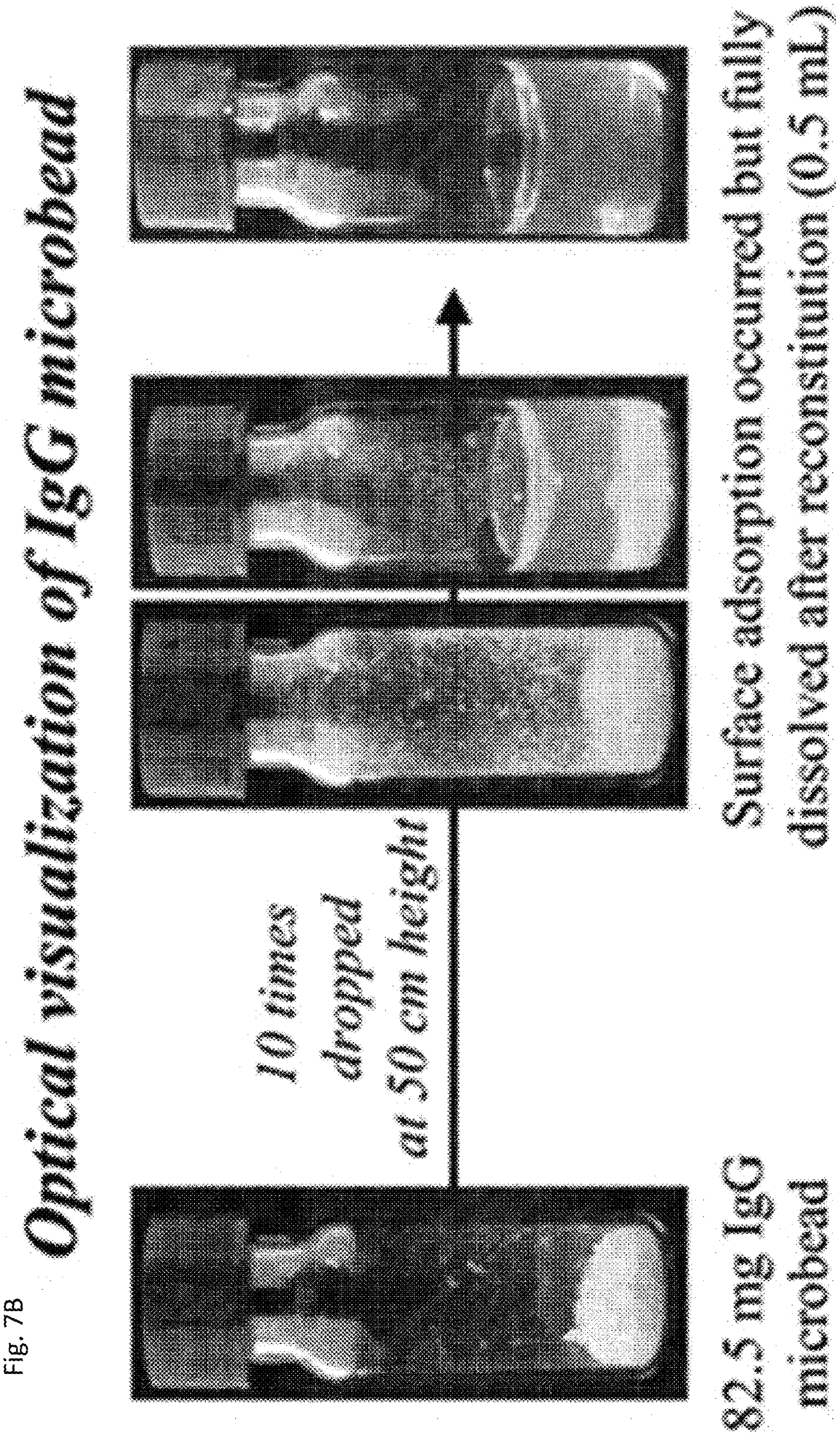
FIG. 7B is a drawing identifying the change when a vial containing 165 mg/mL IgG microbeads is dropped from a height of 50 cm according to an embodiment of the present invention.

FIG. 7A shows the optical difference in the vial before and after dropping it 220 repetitively ten times on a solid bench, with a 165 mg/mL IgG solution (i.e., pH 6.8, 22.5 mg/mL glycine inside). This caused cavitation bubbles and foam to form instantly upon collision, and the bubbles quickly disappeared, leaving only the foam. In contrast, the IgG microbeads shown in FIG. 7B demonstrated surface adhesion in the glass vial after being dropped ten times repetitively and melted during gentle shaking for reconstitution.

Figure 7C:
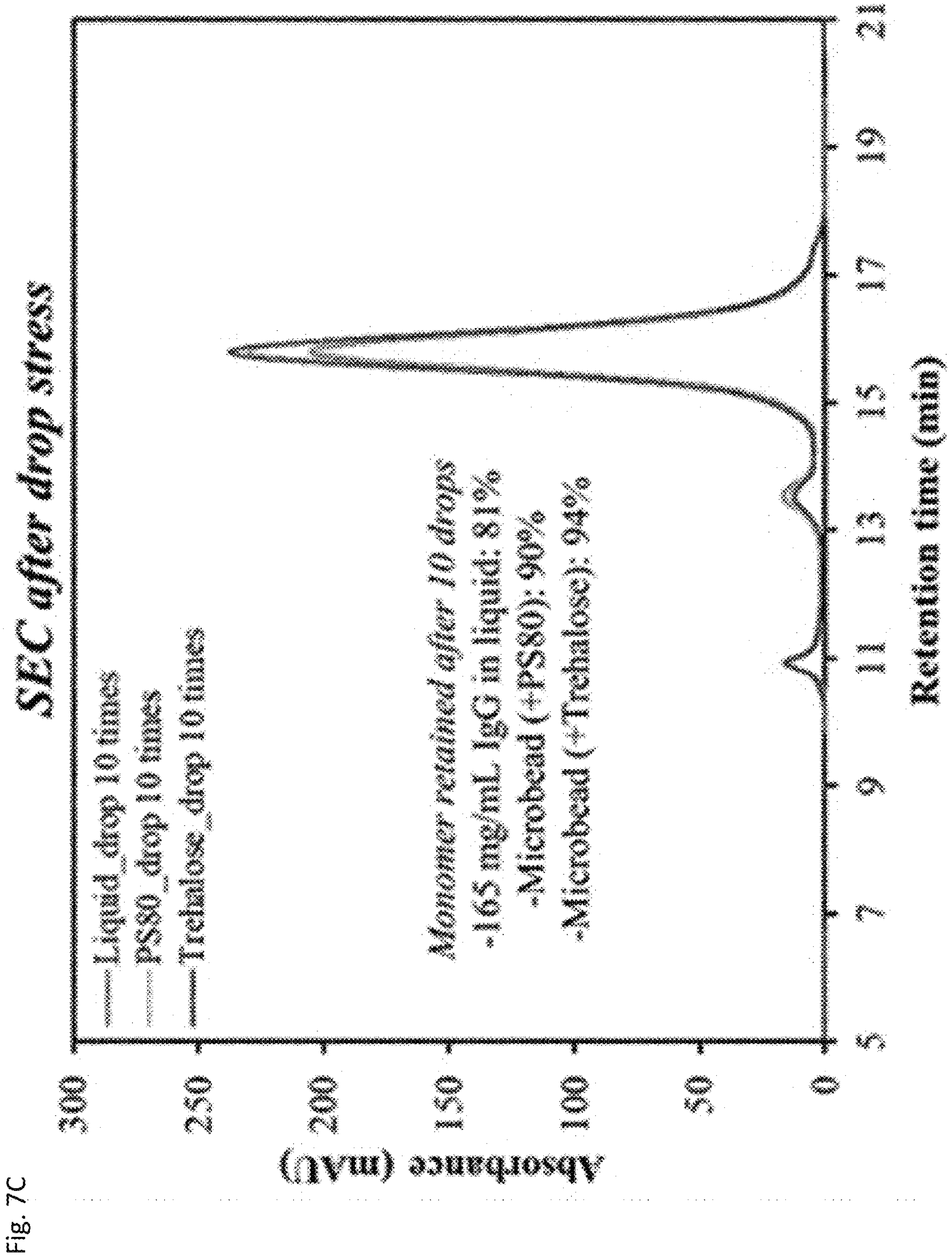
FIG. 7C is a drawing illustrating the monomer reversibility against falling stress of IgG microbeads manufactured using PS80 and trehalose according to an embodiment of the present invention.

Also, as shown in FIG. 7C, the reversibility of IgG in the microbeads prepared using trehalose and PS80 showed approximately 94% and 90% respectively, whereas the monomer left in the solution showed the lowest approximately 81%. As a result, it was confirmed that IgG in the microbeads was more stable under mechanical stress than in the solution.

The careless dropping of vials and syringes almost occurs post-production, particularly during delivery and storage or just prior to administration. Mechanical shock has appeared as a side effect on therapeutic proteins inducing particle formation and protein aggregation. Such effect is not confined to the protein in the solution but causes protein precipitate damage in freeze-dried products, increasing invisible particles and turbidity upon reconstitution. Furthermore, the formation of invisible particles has been accelerated due to the presence of silicone oil in plastic syringes. Harmful effects by drop tests can be explained as due to cavitation and its collapse inducing free radicals, high temperature and secondary shock waves or foam causing interaction of protein molecules adsorbed on the air-liquid layer surface. In fact, high concentration IgG in the solution was more affected by cavitation stress, leading to decrease of monomers and increase of HMW. In contrast, IgG of microbeads was not affected by the stress, maintaining higher monomer content upon reconstitution.

Meanwhile, IgG microbeads containing trehalose showed relatively higher monomer reversibility than PS80 containing IgG microbeads. This suggests that trehalose partially prevented mechanical stress of IgG more than PS80. The result can be speculated because it protects the protein from oxidation or heat due to falling. Previously, trehalose suppressed excessive production of reactive oxygen species in animal models, stabilized proteins during heat shock in yeast cells, and protected micro-encapsulated fish oil from oxidative stress. From the above results, a hypothesis can be established that trehalose plays a role such as stress resistance for proteins and micro particles.

Figure 7D:
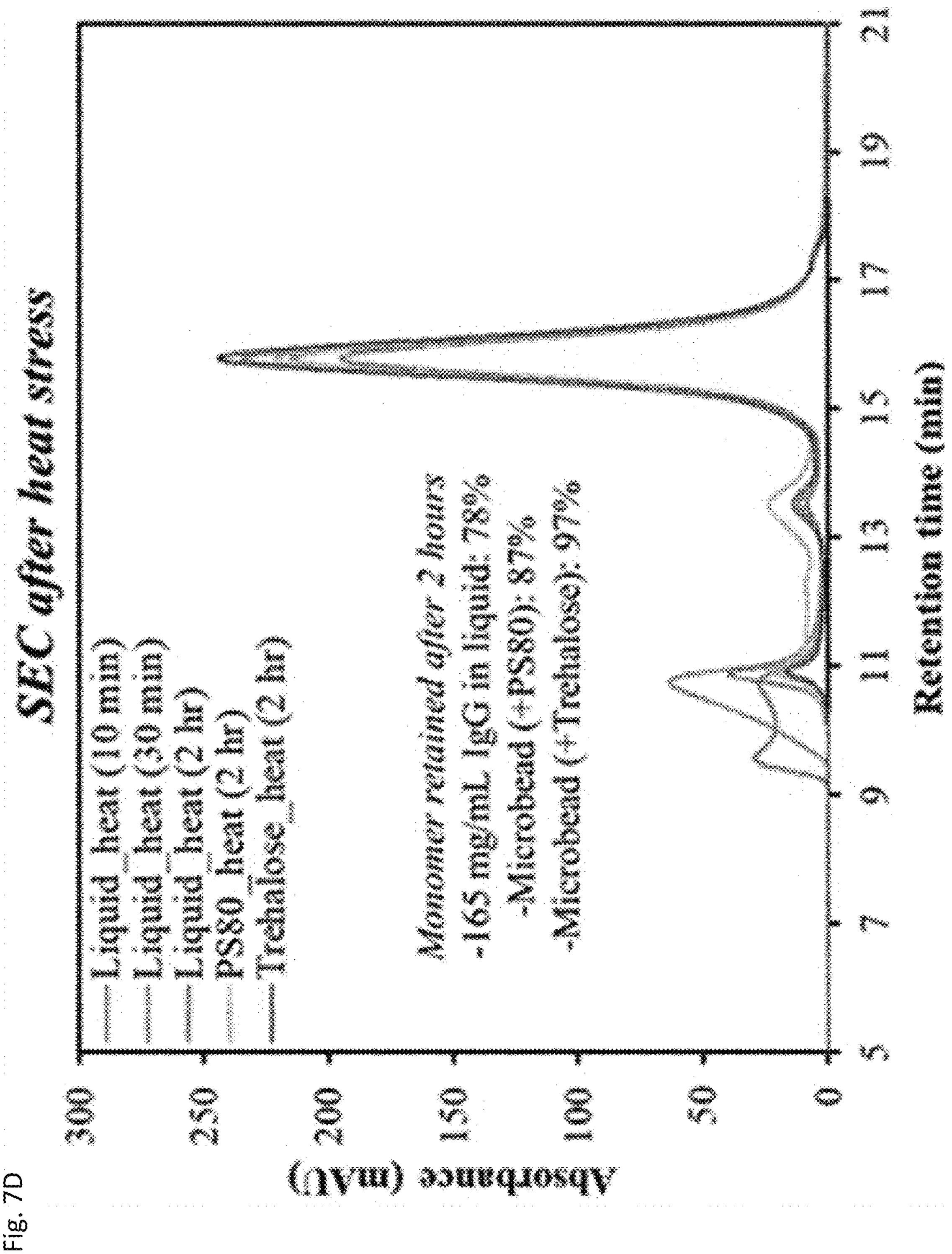
FIG. 7D is a drawing illustrating the monomer reversibility against thermal stress of IgG microbeads manufactured using PS80 and trehalose according to an embodiment of the present invention.

In addition, the newly prepared sample was cultured in vials at high temperature of 55° C. for 2 hours. As a result, as shown in FIG. 7D, the solution IgG 165 mg/mL showed the highest monomer loss of about 78%, while IgG microbeads manufactured using trehalose and PS80 showed about 97% and 87%, respectively. The result consistently shows the stability of IgG in microbeads when adding trehalose. Also, it potentially indicates that the storage period is longer than the solution because the loss of monomer content is slow and protein aggregation formation by high temperature is less.

Experimental Example 8. PK Profile of Reconstituted IgG Microbeads in Rats

IgG microbeads for in vivo studies were prepared based on the previously optimized microbead preparation method; Initial IgG concentration of 25 mg/mL containing 300 mM trehalose pre-mixed in 25 mM acetate buffer at pH 4.0, 4° C. n-octanol, hydrophobic SPG membrane, vortexing for 30 seconds, rinse 3 times with ethanol, then vacuum drying at 200 mTorr vacuum pressure for 48 hours at 35° C.

Table 2 below summarizes the list of pharmacokinetic parameters for IgG in solution and microbeads (i.e., after reconstitution) at two different capacities shown in FIG. 8.

TABLE 2

| Test materials | Dose (mg/kg) | Route | $AUC_{0-28}$ (μg · day/mL) | $C_{max}$ (μg/mL) | $T_{max}$ (day) | $T_{1/2}$ (day) |
|---|---|---|---|---|---|---|
| IgG solution | 25 | IM | 2000 ± 520.4 | 156 ± 22.9 | 3.4 ± 2.1 | 7.9 ± 6.5 |
| IgG microbead (dissolved) | 25 | IM | 1955 ± 340.5 | 169 ± 46.6 | 3.1 ± 2.8 | 9.1 ± 6.3 |
| IgG solution | 50 | IM | 4655 ± 489.7 | 382 ± 32.5 | 3.9 ± 2.6 | 7.2 ± 3.9 |
| IgG microbead (dissolved) | 50 | IM | 4975 ± 1099 | 363 ± 41.1 | 4.4 ± 2.7 | 7.4 ± 2.9 |

Figure 8:
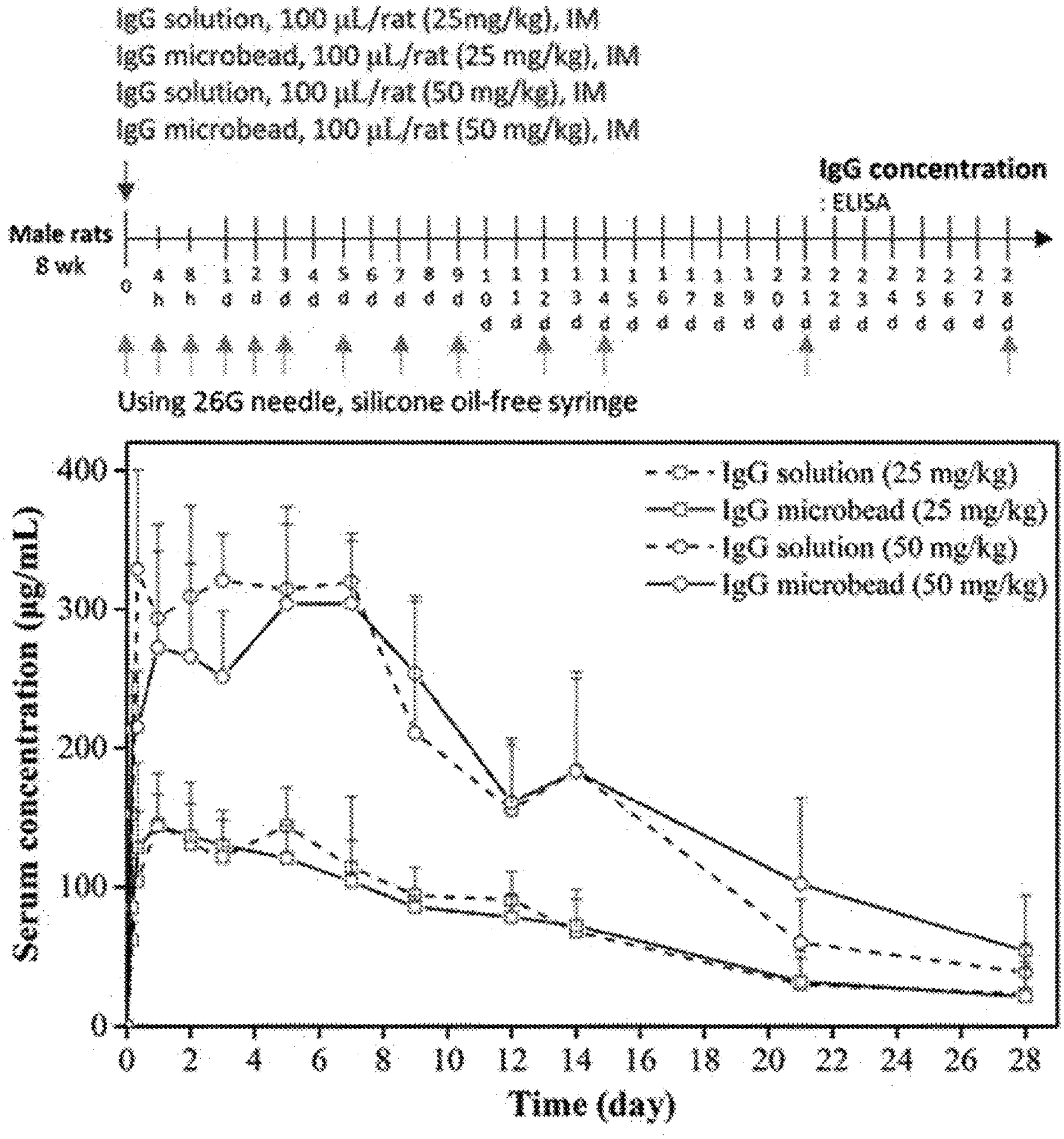
FIG. 8 is a drawing illustrating the average concentration-time profile of IgG in rat serum after a single intramuscular injection of IgG solution and microbeads according to an embodiment of the present invention.

As indicated in Table 2 and FIG. 8, the PK parameters did not demonstrate significant differences when comparing IgG in solutions and microbeads at two different dosages (p-value>0.05). A slight shift in $T_{1/2}$ from 7.9 days to 9.1 days at 25 mg/kg by the IgG microbeads was noted, but it was not statistically significant and thus considered due to outliers. Furthermore, the effects of pH differences (i.e., microbeads at pH 4.0 and solution at pH 6.8) were minimized as initial PK studies on purified monoclonal antibodies with different charge variants had less influence on biological function, and this phenomenon was not observed at high dosage.

In conclusion, all $T_{max}$ and $T_{1/2}$ values for IgG from solution and microbeads after a single IM injection were identical. Similarly, the $AUC_{0-28}$ and $C_{max}$ for IgG in solution were comparable, reaching biological equivalence of more than 97% depending on the dose intensity (i.e., $AUC_{microbeads}/AUC_{solution}$). Overall, IgG microbead after reconstitution behaved almost the same in PK profile as IgG originated from marketed product.

The description of the present invention as stated above is for illustrative purposes only, and a person having ordinary skill in the art to which the present invention pertains will understand that the technical idea or essential characteristics of the present invention can be easily modified into other specific forms without changing them. Therefore, the examples described above should be understood as illustrative in all aspects and not limited.

INDUSTRIAL APPLICABILITY

The method for preparing protein microbeads according to the present invention is expected to be usefully used as a method for improving storage stability by applying the same to the preparation of high-concentration protein pharmaceuticals and the like, thereby demonstrating industrial applicability.

The invention claimed is:

1. A method for preparing protein microbeads, comprising the following steps:

(a) stirring an emulsion prepared by mixing protein with a process stabilizer and an organic solvent and dehydrating the protein, wherein the process stabilizer is trehalose;

(b) removing the supernatant by centrifuging a precipitate formed by stirring the emulsion and dehydrating the protein; and (c) drying after removing the supernatant, and wherein the step (a) further comprises emulsifying the protein through a hydrophobized Shirasu porous glass (SPG) membrane prior to stirring the emulsion.

2. The method of claim 1, wherein the protein is one or more selected from the group consisting of antibodies, aptamers, fusion proteins, Fc fusion proteins, PEGylated proteins, synthetic polypeptides, protein fragments, lipoproteins, enzymes, hormones, immunogenic proteins, structural peptides, and peptide drugs.

3. The method of claim 1, wherein the organic solvent is a non-aqueous organic solvent that does not mix with water and has a water saturation fraction (f) value of 0.5 or less.

4. The method of claim 3, wherein the organic solvent is one or more selected from the group consisting of carbonates, esters, ethers, ketones, alcohols, non-polar solvents, and their isomers.

5. The method of claim 4, wherein the organic solvent is n-octanol.

6. The method of claim 1, wherein the reversibility of the protein microbeads is 90% to 100%.

7. The method of claim 1, wherein the protein microbeads have stability against physical shocks or high temperature stress of 40° C. to 70° C.

8. The method of claim 1, wherein the dehydration in the step (a) is performed for 10 seconds to 20 minutes.

9. The method of claim 1, wherein the drying in the step (c) is performed at 25° C. to 40° C. for 24 to 130 hours under a pressure of 50 mTorr to 300 mTorr.

10. The method of claim 1, wherein the protein microbeads is formulated into one or more form selected from the group consisting of injectables, inhalants, patches, and topical formulations.

* * * * *